(12) United States Patent
Parry et al.

(10) Patent No.: US 11,999,780 B2
(45) Date of Patent: Jun. 4, 2024

(54) HUMANIZED ANTI-COMPLEMENT FACTOR BB ANTIBODIES AND USES THEREOF

(71) Applicant: Genzyme Corporation, Cambridge, MA (US)

(72) Inventors: Graham Parry, Burlington, MA (US); Stephen Moore, Danville, CA (US); Michael Storek, Bridgewater, NJ (US); Nina C. Leksa, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 17/557,318

(22) Filed: Dec. 21, 2021

(65) Prior Publication Data

US 2022/0213179 A1    Jul. 7, 2022

Related U.S. Application Data

(62) Division of application No. 17/234,618, filed on Apr. 19, 2021, now Pat. No. 11,242,382.

(60) Provisional application No. 63/012,590, filed on Apr. 20, 2020.

(51) Int. Cl.
| | | |
|---|---|---|
| *C07K 16/18* | (2006.01) | |
| *A61K 39/00* | (2006.01) | |
| *A61K 47/68* | (2017.01) | |
| *A61P 13/00* | (2006.01) | |

(52) U.S. Cl.
CPC .......... *C07K 16/18* (2013.01); *A61K 47/6843* (2017.08); *C07K 2317/24* (2013.01); *C07K 2317/31* (2013.01); *C07K 2317/52* (2013.01); *C07K 2317/92* (2013.01)

(58) Field of Classification Search
CPC .......................... C07K 16/18; C07K 2317/24; C07K 2317/31; C07K 2317/52; C07K 2317/92; C07K 2317/33; C07K 2317/76; A61K 47/6843
See application file for complete search history.

(56) References Cited

U.S. PATENT DOCUMENTS

| | | | |
|---|---|---|---|
| 6,737,056 B1 | 5/2004 | Presta | |
| 10,934,347 B2 | 3/2021 | Panicker et al. | |
| 11,192,944 B2 | 12/2021 | Panicker et al. | |
| 11,242,382 B2 | 2/2022 | Parry et al. | |
| 2005/0226876 A1* | 10/2005 | Graus et al. ............... | A61P 7/02 536/23.53 |
| 2009/0214538 A1 | 8/2009 | Fung et al. | |
| 2009/0280128 A1 | 11/2009 | Kamogawa et al. | |
| 2013/0136735 A1 | 5/2013 | Truneh et al. | |
| 2014/0286936 A1 | 9/2014 | Chambers et al. | |
| 2015/0239987 A1 | 8/2015 | Liang et al. | |
| 2016/0015828 A1 | 1/2016 | Torgov et al. | |
| 2017/0044259 A1 | 2/2017 | Tipton et al. | |
| 2019/0153079 A1 | 5/2019 | Panicker et al. | |
| 2020/0239556 A1 | 7/2020 | Panicker et al. | |
| 2021/0221877 A1 | 7/2021 | Panicker et al. | |

FOREIGN PATENT DOCUMENTS

| | | | |
|---|---|---|---|
| CN | 101918444 A | 12/2010 | |
| CN | 104220454 A | 12/2014 | |
| CN | 104884088 A | 9/2015 | |
| CN | 106232624 A | 12/2016 | |
| CN | 109563158 A | 4/2019 | |
| JP | 2015-514111 A | 5/2015 | |
| JP | 2020078304 A | 5/2020 | |
| WO | WO 97/34631 A1 | 9/1997 | |
| WO | WO 98/23289 A1 | 6/1998 | |
| WO | WO 02/060919 A2 | 8/2002 | |
| WO | WO 2005/077417 A1 | 8/2005 | |
| WO | WO 2009/029669 A1 | 3/2009 | |
| WO | WO 2009/082624 A2 | 7/2009 | |
| WO | WO 2011/041391 A1 | 4/2011 | |
| WO | WO 2013/126746 A2 | 8/2013 | |
| WO | WO 2013/152020 A1 | 10/2013 | |
| WO | WO 2014/044793 A2 | 3/2014 | |
| WO | WO 2015/051159 A1 | 4/2015 | |
| WO | WO 2015/130826 A1 | 9/2015 | |
| WO | WO 2017/176651 A1 | 10/2017 | |
| WO | WO 2018/071676 A1 | 4/2018 | |
| WO | WO-2018071676 A1 * | 4/2018 | .............. A61P 43/00 |
| WO | WO 2019/075220 A1 | 4/2019 | |

OTHER PUBLICATIONS

International Preliminary Report on Patentability, dated Nov. 3, 2022 for Application No. PCT/US2021/027981.
Daha et al., Stabilization of the amplification convertase of complement by monoclonal antibodies directed against human factor B. J Immunol. May 1984;132(5):2538-42.
Extended European Search Report, dated Dec. 17, 2019 for Application No. EP 17779607.5.
Invitation to Pay Additional Fees, dated Jul. 17, 2017 for Application No. PCT/US2017/025784.
International Search Report and Written Opinion, dated Sep. 7, 2017 for Application No. PCT/US2017/025784.
International Preliminary Report on Patentability, dated Oct. 18, 2018 for Application PCT/US2017/025784.
International Search Report and Written Opinion, dated Jan. 3, 2019 for Application No. PCT/US2018/055444.
International Preliminary Report on Patentability, dated Apr. 23, 2020 for Application No. PCT/US2018/055444.
International Search Report and Written Opinion, dated Aug. 25, 2021 for Application No. PCT/US2021/027981.
Bryson et al., Prediction of immunogenicity of therapeutic proteins: validity of computational tools. BioDrugs. Feb. 1, 2010;24(1):1-8.

(Continued)

*Primary Examiner* — Vanessa L. Ford
*Assistant Examiner* — Danaya L Middleton
(74) *Attorney, Agent, or Firm* — Wolf, Greenfield & Sacks, P.C.

(57) ABSTRACT

Provided herein are humanized anti-factor Bb antibodies, methods of producing the antibodies and methods of using the antibodies.

17 Claims, 22 Drawing Sheets

Specification includes a Sequence Listing.

(56) References Cited

OTHER PUBLICATIONS

Cao et al., Human neutrophil peptides and complement factor Bb in pathogenesis of acquired thrombotic thrombocytopenia purpura. Haematologica. Nov. 2016;101(11):1319-1326. Epub Aug. 4, 2016.

Chen et al., Enhancement and destruction of antibody function by somatic mutation: unequal occurrence is controlled by V gene combinatorial associations. EMBO J. Jun. 15, 1995;14(12):2784-94.

Chothia et al., Canonical structures for the hypervariable regions of immunoglobulins. J Mol Biol. Aug. 20, 1987;196(4):901-17.

Dall'Acqua et al., Properties of human IgG1s engineered for enhanced binding to the neonatal Fc receptor (FcRn). J Biol Chem. Aug. 18, 2006;281(33):23514-24. Epub Jun. 21, 2006.

De Vriese et al., Kidney Disease Caused by Dysregulation of the Complement Alternative Pathway: An Etiologic Approach. J Am Soc Nephrol. Dec. 2015;26(12):2917-29. Epub Jul. 16, 2015.

Gold et al., Variation in factor B (BF) and complement component 2 (C2) genes is associated with age-related macular degeneration. Nat Genet. Apr. 2006;38(4):458-62. Epub Mar. 5, 2006. Author manuscript.

Holers, The spectrum of complement alternative pathway-mediated diseases. Immunol Rev. Jun. 2008;223:300-16.

Holt et al., Domain antibodies: proteins for therapy. Trends Biotechnol. Nov. 2003;21(11):484-90.

Kabat et al., Unusual distributions of amino acids in complementarity-determining (hypervariable) segments of heavy and light chains of immunoglobulins and their possible roles in specificity of antibody-combining sites. J Biol Chem. Oct. 10, 1977;252(19):6609-16.

Kussie et al., A single engineered amino acid substitution changes antibody fine specificity. J Immunol. Jan. 1, 1994;152(1):146-52.

Koenig et al., Mutational landscape of antibody variable domains reveals a switch modulating the interdomain conformational dynamics and antigen binding. Proc Natl Acad Sci U S A. Jan. 24, 2017;114(4):E486-E495. doi: 10.1073/pnas.1613231114. Epub Jan. 5, 2017.

Lefranc et al., IMGT unique numbering for immunoglobulin and T cell receptor variable domains and Ig superfamily V-like domains. Dev Comp Immunol. Jan. 2003;27(1):55-77.

Maccallum et al., Antibody-antigen interactions: contact analysis and binding site topography. J Mol Biol. Oct. 11, 1996;262(5):732-45.

Perry et al., New approaches to prediction of immune responses to therapeutic proteins during preclinical development. Drugs R D. 2008;9(6):385-96.

Pio et al., The Role of Complement in Tumor Growth. Adv Exp Med Biol. 2014;772: 229-262. Author manuscript.

Schubart et al., Small-molecule factor B inhibitor for the treatment of complement-mediated diseases. Proc Natl Acad Sci U S A. Apr. 16, 2019;116(16):7926-7931. Epub Mar. 29, 2019.

Shaner et al., A guide to choosing fluorescent proteins. Nat Methods. Dec. 2005;2(12):905-9.

Shields et al., High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001;276(9):6591-604. Epub Nov. 28, 2000.

Smith et al., Mouse model recapitulating human Fcγ receptor structural and functional diversity. Proc Natl Acad Sci U S A. Apr. 17, 2012;109(16):6181-6. Epub Apr. 2, 2012.

Thurman, Complement in kidney disease: core curriculum 2015. Am J Kidney Dis. Jan. 2015;65(1):156-68. Epub Oct. 18, 2014. Author manuscript.

Thurman et al., Complement Therapeutics in Autoimmune Disease. Front Immunol. Apr. 3, 2019;10:672. 9 pages.

* cited by examiner

HUMANIZED ANTI-COMPLEMENT FACTOR BB ANTIBODIES AND USES THEREOF

RELATED APPLICATION

This application is a division of U.S. application Ser. No. 17/234,618 filed Apr. 19, 2021, which claims priority to U.S. provisional application Ser. No. 63/012,590, filed Apr. 20, 2020, the entire content of each of which is incorporated by reference herein.

REFERENCE TO A SEQUENCE LISTING SUBMITTED AS A TEXT FILE VIA EFS-WEB

The present application contains a Sequence Listing which has been submitted in ASCII format via EFS-Web and is hereby incorporated by reference in its entirety. Said ASCII copy, created on Dec. 21, 2021, is named B155370014US02-SEQ-HJD and is 69,946 bytes in size.

FIELD OF THE INVENTION

The present application relates to humanized anti-factor Bb antibodies and the use of the antibodies.

BACKGROUND

The complement system is part of the innate immune system. Its primary role is to "complement" the ability of antibodies and phagocytic cells to clear harmful pathogens from an organism. The complement system includes three separate upstream activation pathways (the classical pathway, the alternative pathway and the lectin pathway), all converging on a common terminal pathway. Factor B is a component of the alternative pathway of complement and can be cleaved into factor Ba and factor Bb. Factor B also contains a serine protease (SP) domain, and when activated it provides the catalytic activity of the alternative pathway C3 and C5 convertases. Aberrant activation of the complement system can cause damage to host tissue in a wide variety of pathological settings, ranging from autoimmune disease to organ transplantation. There is still a need for treating diseases or disorders associated with complement system. The present invention addresses this need and others.

SUMMARY

The present disclosure provides, in some aspects, humanized anti-factor Bb antibodies, compositions comprising the antibodies, methods of producing the antibodies, and methods of using the antibodies, for example, for treating a complement-mediated disease or disorder. As shown in the data provided herein, the humanized anti-factor Bb antibodies of the present disclosure have a binding affinity within two-fold of that of the parent antibody. Unexpectedly, initial attempts to humanize the parent mouse anti-factor Bb antibody produced a majority of variants lacking an acceptable binding affinity. Thus, to produce humanized versions having suitable binding affinities (e.g., to treat complement-mediated diseases or disorders), multiple rounds of humanization were required. Further, only certain $V_H$ and $V_L$ domains could be combined to produce an antibody that bound to factor Bb with an acceptable binding affinity see, e.g., antibodies tested in Example 1, Table 9.

Some aspects of the present disclosure provide a humanized antibody that binds specifically to human complement factor Bb protein and comprises a heavy chain variable region ($V_H$) comprising the amino acid sequence of SEQ ID NO: 19 and a light chain variable region ($V_L$) comprising the amino acid sequence of SEQ ID NO: 27.

Other aspects of the present disclosure provide a humanized antibody that binds specifically to human complement factor Bb protein and comprises a $V_H$ comprising the amino acid sequence of SEQ ID NO: 17 and a $V_L$ comprising the amino acid sequence of SEQ ID NO: 26.

In some embodiments, the humanized antibody binds specifically to the human complement factor Bb protein with an affinity of $10^{-6}$ to $10^{-9}$ M.

In some embodiments, the humanized antibody inhibits a complement pathway activity. In some embodiments, the complement pathway activity is the alternative pathway (AP) activity.

In some embodiments, the complement AP activity is selected from the group consisting of: AP-mediated terminal membrane attack complex (MAC) deposition, AP-mediated hemolysis, C3 fragment deposition on red blood cells or other cell types, C3b/Bb-mediated cleavage of C3, and C3bBb3b-mediated cleavage of C5.

In some embodiments, the humanized antibody is a bispecific antibody or a multispecific antibody.

In some embodiments, the humanized antibody is selected from the group consisting of an Ig monomer, a Fab fragment, a F(ab')2 fragment, a scFv, a scAb, and a Fv.

In some embodiments, the humanized antibody comprises a heavy chain constant region of the isotype IgG1, IgG2, IgG3, or IgG4.

In some embodiments, the humanized antibody comprises an IgG4 constant region or a variant thereof.

In some embodiments, the heavy chain constant region comprises an amino acid sequence that is at least 90% identical to any one of SEQ ID NOs: 28-30.

In some embodiments, the humanized antibody comprises a heavy chain comprising the amino acid sequence of any one of SEQ ID NOs: 32-34 and a light chain comprising the amino acid sequence of SEQ ID NO: 35.

In some embodiments, the humanized antibody comprises a heavy chain comprising the amino acid sequence of any one of SEQ ID NOs: 36-38 and a light chain comprising the amino acid sequence of SEQ ID NO: 39.

Also provided herein are conjugates comprising a humanized antibody of the present disclosure.

In some embodiments, a humanized anti-factor Bb antibody of a conjugate comprises a $V_H$ comprising the amino acid sequence of SEQ ID NO: 19 and a $V_L$ comprising the amino acid sequence of SEQ ID NO: 27. In some embodiments, a humanized anti-factor Bb antibody of a conjugate comprises a heavy chain comprising the amino acid sequence of SEQ ID NO: 34 and a light chain comprising the amino acid sequence of SEQ ID NO: 35.

In some embodiments, a humanized anti-factor Bb antibody of a conjugate comprises a $V_H$ comprising the amino acid sequence of SEQ ID NO: 17 and a $V_L$ comprising the amino acid sequence of SEQ ID NO: 26. In some embodiments, a humanized anti-factor Bb antibody of a conjugate comprises a heavy chain comprising the amino acid sequence of SEQ ID NO: 38 and a light chain comprising the amino acid sequence of SEQ ID NO: 39.

Further provided herein are pharmaceutical compositions comprising a humanized antibody described herein or a conjugate described herein.

In some embodiments, a pharmaceutical composition comprises a humanized anti-factor Bb antibody that comprises a $V_H$ comprising the amino acid sequence of SEQ ID NO: 19 and a $V_L$ comprising the amino acid sequence of SEQ ID NO: 27. In some embodiments, a pharmaceutical composition comprises a humanized anti-factor Bb antibody that comprises a heavy chain comprising the amino acid sequence of SEQ ID NO: 34 and a light chain comprising the amino acid sequence of SEQ ID NO: 35.

In some embodiments, a pharmaceutical composition comprises a humanized anti-factor Bb antibody that comprises a $V_H$ comprising the amino acid sequence of SEQ ID NO: 17 and a $V_L$ comprising the amino acid sequence of SEQ ID NO: 26. In some embodiments, a pharmaceutical composition comprises a humanized anti-factor Bb antibody that comprises a heavy chain comprising the amino acid sequence of SEQ ID NO: 38 and a light chain comprising the amino acid sequence of SEQ ID NO: 39.

In some embodiments, a pharmaceutical composition comprises a conjugate that comprises a humanized anti-factor Bb antibody that comprises a $V_H$ comprising the amino acid sequence of SEQ ID NO: 19 and a $V_L$ comprising the amino acid sequence of SEQ ID NO: 27. In some embodiments, a pharmaceutical composition comprises a conjugate that comprises a humanized anti-factor Bb antibody that comprises a heavy chain comprising the amino acid sequence of SEQ ID NO: 34 and a light chain comprising the amino acid sequence of SEQ ID NO: 35.

In some embodiments, a pharmaceutical composition comprises a conjugate that comprises a humanized anti-factor Bb antibody that comprises a $V_H$ comprising the amino acid sequence of SEQ ID NO: 17 and a $V_L$ comprising the amino acid sequence of SEQ ID NO: 26. In some embodiments, a pharmaceutical composition comprises a conjugate that comprises a humanized anti-factor Bb antibody that comprises a heavy chain comprising the amino acid sequence of SEQ ID NO: 38 and a light chain comprising the amino acid sequence of SEQ ID NO: 39.

In some embodiments, a pharmaceutical composition further comprises a pharmaceutically acceptable excipient.

Also provided herein are devices comprising a humanized antibody described herein, a conjugate described herein, or a pharmaceutical composition described herein.

In some embodiments, a device comprises a humanized anti-factor Bb antibody that comprises a $V_H$ comprising the amino acid sequence of SEQ ID NO: 19 and a $V_L$ comprising the amino acid sequence of SEQ ID NO: 27. In some embodiments, a device comprises a humanized anti-factor Bb antibody that comprises a heavy chain comprising the amino acid sequence of SEQ ID NO: 34 and a light chain comprising the amino acid sequence of SEQ ID NO: 35.

In some embodiments, a device comprises a humanized anti-factor Bb antibody that comprises a $V_H$ comprising the amino acid sequence of SEQ ID NO: 17 and a $V_L$ comprising the amino acid sequence of SEQ ID NO: 26. In some embodiments, a device comprises a humanized anti-factor Bb antibody that comprises a heavy chain comprising the amino acid sequence of SEQ ID NO: 38 and a light chain comprising the amino acid sequence of SEQ ID NO: 39.

In some embodiments, a device comprises a conjugate that comprises a humanized anti-factor Bb antibody that comprises a $V_H$ comprising the amino acid sequence of SEQ ID NO: 19 and a $V_L$ comprising the amino acid sequence of SEQ ID NO: 27. In some embodiments, a device comprises a conjugate that comprises a humanized anti-factor Bb antibody that comprises a heavy chain comprising the amino acid sequence of SEQ ID NO: 34 and a light chain comprising the amino acid sequence of SEQ ID NO: 35.

In some embodiments, a device comprises a conjugate that comprises a humanized anti-factor Bb antibody that comprises a $V_H$ comprising the amino acid sequence of SEQ ID NO: 17 and a $V_L$ comprising the amino acid sequence of SEQ ID NO: 26. In some embodiments, a device comprises a conjugate that comprises a humanized anti-factor Bb antibody that comprises a heavy chain comprising the amino acid sequence of SEQ ID NO: 38 and a light chain comprising the amino acid sequence of SEQ ID NO: 39.

In some embodiments, a device comprises a pharmaceutical composition that comprises a humanized anti-factor Bb antibody that comprises a $V_H$ comprising the amino acid sequence of SEQ ID NO: 19 and a $V_L$ comprising the amino acid sequence of SEQ ID NO: 27. In some embodiments, a device comprises a pharmaceutical composition that comprises a humanized anti-factor Bb antibody that comprises a heavy chain comprising the amino acid sequence of SEQ ID NO: 34 and a light chain comprising the amino acid sequence of SEQ ID NO: 35.

In some embodiments, a device comprises a pharmaceutical composition that comprises a humanized anti-factor Bb antibody that comprises a $V_H$ comprising the amino acid sequence of SEQ ID NO: 17 and a $V_L$ comprising the amino acid sequence of SEQ ID NO: 26. In some embodiments, a device comprises a pharmaceutical composition that comprises a humanized anti-factor Bb antibody that comprises a heavy chain comprising the amino acid sequence of SEQ ID NO: 38 and a light chain comprising the amino acid sequence of SEQ ID NO: 39.

In some embodiments, the device is an injectable device, for example, a syringe, a pen, or an electronic injection device (e-Device).

Yet other aspects of the present disclosure provide methods of treating a subject having a complement-mediated disease or disorder, the methods comprising administering to the subject an effective amount of a humanized antibody described herein, a conjugate described herein, or a pharmaceutical composition described herein to treat the complement-mediated disease or disorder.

In some embodiments, a method of treating a subject having a complement-mediated disease or disorder comprises administering to the subject an effective amount of a humanized anti-factor Bb antibody that comprises a $V_H$ comprising the amino acid sequence of SEQ ID NO: 19 and a $V_L$ comprising the amino acid sequence of SEQ ID NO: 27, to treat the complement-mediated disease or disorder. In some embodiments, a method of treating a subject having a complement-mediated disease or disorder comprises administering to the subject an effective amount of a humanized anti-factor Bb antibody that comprises a heavy chain comprising the amino acid sequence of SEQ ID NO: 34 and a light chain comprising the amino acid sequence of SEQ ID NO: 35, to treat the complement-mediated disease or disorder.

In some embodiments, a method of treating a subject having a complement-mediated disease or disorder comprises administering to the subject an effective amount of a humanized anti-factor Bb antibody that comprises a $V_H$ comprising the amino acid sequence of SEQ ID NO: 17 and a $V_L$ comprising the amino acid sequence of SEQ ID NO: 26, to treat the complement-mediated disease or disorder. In some embodiments, a method of treating a subject having a complement-mediated disease or disorder comprises administering to the subject an effective amount of a humanized anti-factor Bb antibody that comprises a heavy chain comprising the amino acid sequence of SEQ ID NO: 38 and a light chain comprising the amino acid sequence of SEQ ID NO: 39, to treat the complement-mediated disease or disorder.

In some embodiments, a method of treating a subject having a complement-mediated disease or disorder comprises administering to the subject an effective amount of a conjugate that comprises a humanized anti-factor Bb antibody that comprises a $V_H$ comprising the amino acid sequence of SEQ ID NO: 19 and a $V_L$ comprising the amino acid sequence of SEQ ID NO: 27, to treat the complement-mediated disease or disorder. In some embodiments, a method of treating a subject having a complement-mediated disease or disorder comprises administering to the subject an effective amount of a conjugate that comprises a heavy chain comprising the amino acid sequence of SEQ ID NO: 34 and a light chain comprising the amino acid sequence of SEQ ID NO: 35, to treat the complement-mediated disease or disorder.

In some embodiments, a method of treating a subject having a complement-mediated disease or disorder comprises administering to the subject an effective amount of a conjugate that comprises a $V_H$ comprising the amino acid sequence of SEQ ID NO: 17 and a $V_L$ comprising the amino acid sequence of SEQ ID NO: 26, to treat the complement-mediated disease or disorder. In some embodiments, a method of treating a subject having a complement-mediated disease or disorder comprises administering to the subject an effective amount of a conjugate that comprises a heavy chain comprising the amino acid sequence of SEQ ID NO: 38 and a light chain comprising the amino acid sequence of SEQ ID NO: 39, to treat the complement-mediated disease or disorder.

In some embodiments, a method of treating a subject having a complement-mediated disease or disorder comprises administering to the subject an effective amount of a pharmaceutical composition that comprises a humanized anti-factor Bb antibody that comprises a $V_H$ comprising the amino acid sequence of SEQ ID NO: 19 and a $V_L$ comprising the amino acid sequence of SEQ ID NO: 27, to treat the complement-mediated disease or disorder. In some embodiments, a method of treating a subject having a complement-mediated disease or disorder comprises administering to the subject an effective amount of a pharmaceutical composition that comprises a heavy chain comprising the amino acid sequence of SEQ ID NO: 34 and a light chain comprising the amino acid sequence of SEQ ID NO: 35, to treat the complement-mediated disease or disorder.

In some embodiments, a method of treating a subject having a complement-mediated disease or disorder comprises administering to the subject an effective amount of a pharmaceutical composition that comprises a $V_H$ comprising the amino acid sequence of SEQ ID NO: 17 and a $V_L$ comprising the amino acid sequence of SEQ ID NO: 26, to treat the complement-mediated disease or disorder. In some embodiments, a method of treating a subject having a complement-mediated disease or disorder comprises administering to the subject an effective amount of a pharmaceutical composition that comprises a heavy chain comprising the amino acid sequence of SEQ ID NO: 38 and a light chain comprising the amino acid sequence of SEQ ID NO: 39, to treat the complement-mediated disease or disorder.

In some embodiments, the complement-mediated disease is selected from the group consisting of: IgA nephropathy (Berger's disease), atypical hemolytic uremic syndrome (aHUS), paroxysmal nocturnal hemoglobinuria (PNH), idiopathic thrombocytopenic purpura (ITP), thrombotic thrombocytopenic purpura (TTP), lupus nephritis, ANCA vasculitis, membranous nephropathy, C3 glomerulonephritis (C3GN), focal segmental glomerulosclerosis (FSGS), multiple sclerosis, macular degeneration, age-related macular degeneration (AMD), rheumatoid arthritis, antiphospholipid antibody syndrome, asthma, ischemia-reperfusion injury, Type II membranoproliferative glomerulonephritis (GN), spontaneous fetal loss, Pauci-immune vasculitis, epidermolysis bullosa, recurrent fetal loss, and traumatic brain injury.

Still other aspects of the present disclosure provide methods of inhibiting a complement pathway activity in a subject. In some embodiments, the complement pathway activity is an alternative pathway (AP) activity. In some embodiments, a method of inhibiting a complement pathway activity (e.g., AP activity) in a subject comprises administering to the subject an effective amount of a humanized anti-factor Bb antibody, a conjugate comprising a humanized anti-factor Bb antibody, or a pharmaceutical composition comprising a humanized anti-factor Bb antibody, to inhibit the complement pathway activity.

In some embodiments, a method of inhibiting a complement pathway activity (e.g., AP activity) in a subject comprises administering to the subject an effective amount of a humanized anti-factor Bb antibody that comprises a $V_H$ comprising the amino acid sequence of SEQ ID NO: 19 and a $V_L$ comprising the amino acid sequence of SEQ ID NO: 27, to inhibit the complement pathway activity. In some embodiments, a method of inhibiting a complement pathway activity (e.g., AP activity) in a subject comprises administering to the subject an effective amount of a humanized anti-factor Bb antibody that comprises a heavy chain comprising the amino acid sequence of SEQ ID NO: 34 and a light chain comprising the amino acid sequence of SEQ ID NO: 35, to inhibit the complement pathway activity.

In some embodiments, a method of inhibiting a complement pathway activity (e.g., AP activity) in a subject comprises administering to the subject an effective amount of a humanized anti-factor Bb antibody that comprises a $V_H$ comprising the amino acid sequence of SEQ ID NO: 17 and a $V_L$ comprising the amino acid sequence of SEQ ID NO: 26, to inhibit the complement pathway activity. In some embodiments, a method of inhibiting a complement pathway activity (e.g., AP activity) in a subject comprises administering to the subject an effective amount of a humanized anti-factor Bb antibody that comprises a heavy chain comprising the amino acid sequence of SEQ ID NO: 38 and a light chain comprising the amino acid sequence of SEQ ID NO: 39, to inhibit the complement pathway activity.

In some embodiments, a method of inhibiting a complement pathway activity (e.g., AP activity) in a subject comprises administering to the subject an effective amount of a conjugate that comprises a humanized anti-factor Bb antibody that comprises a $V_H$ comprising the amino acid sequence of SEQ ID NO: 19 and a $V_L$ comprising the amino acid sequence of SEQ ID NO: 27, to inhibit the complement pathway activity. In some embodiments, a method of inhibiting a complement pathway activity (e.g., AP activity) in a subject comprises administering to the subject an effective amount of a conjugate that comprises a humanized anti-factor Bb antibody that comprises a heavy chain comprising the amino acid sequence of SEQ ID NO: 34 and a light chain comprising the amino acid sequence of SEQ ID NO: 35, to inhibit the complement pathway activity.

In some embodiments, a method of inhibiting a complement pathway activity (e.g., AP activity) in a subject comprises administering to the subject an effective amount of a conjugate that comprises a humanized anti-factor Bb antibody that comprises a $V_H$ comprising the amino acid sequence of SEQ ID NO: 17 and a $V_L$ comprising the amino acid sequence of SEQ ID NO: 26, to inhibit the complement pathway activity. In some embodiments, a method of inhibiting a complement pathway activity (e.g., AP activity) in a subject comprises administering to the subject an effective amount of a conjugate that comprises a humanized anti-factor Bb antibody that comprises a heavy chain comprising the amino acid sequence of SEQ ID NO: 38 and a light chain comprising the amino acid sequence of SEQ ID NO: 39, to inhibit the complement pathway activity.

In some embodiments, a method of inhibiting a complement pathway activity (e.g., AP activity) in a subject comprises administering to the subject an effective amount of a pharmaceutical composition that comprises a humanized anti-factor Bb antibody that comprises a $V_H$ comprising the amino acid sequence of SEQ ID NO: 19 and a $V_L$ comprising the amino acid sequence of SEQ ID NO: 27, to inhibit the complement pathway activity. In some embodiments, a method of inhibiting a complement pathway activity (e.g., AP activity) in a subject comprises administering to the subject an effective amount of a pharmaceutical composition that comprises a humanized anti-factor Bb antibody that comprises a heavy chain comprising the amino acid sequence of SEQ ID NO: 34 and a light chain comprising the amino acid sequence of SEQ ID NO: 35, to inhibit the complement pathway activity.

In some embodiments, a method of inhibiting a complement pathway activity (e.g., AP activity) in a subject comprises administering to the subject an effective amount of a pharmaceutical composition that comprises a humanized anti-factor Bb antibody that comprises a $V_H$ comprising the amino acid sequence of SEQ ID NO: 17 and a $V_L$ comprising the amino acid sequence of SEQ ID NO: 26, to inhibit the complement pathway activity. In some embodiments, a method of inhibiting a complement pathway activity (e.g., AP activity) in a subject comprises administering to the subject an effective amount of a pharmaceutical composition that comprises a humanized anti-factor Bb antibody that comprises a heavy chain comprising the amino acid sequence of SEQ ID NO: 38 and a light chain comprising the amino acid sequence of SEQ ID NO: 39, to inhibit the complement pathway activity.

In some embodiments, the complement AP activity is selected from the group consisting of: AP-mediated terminal membrane attack complex (MAC) deposition, AP-mediated hemolysis, C3 fragment deposition on red blood cells or other cell types, C3b/Bb-mediated cleavage of C3, and C3bBb3b-mediated cleavage of C5. In some embodiments, the subject has a complement-mediated disease or disorder.

In some embodiments, a method further comprises administering to the subject a therapeutic agent.

In some embodiments, administering is intravenous, subcutaneous, or intramuscular.

Also provided herein are humanized anti-factor Bb antibodies for use in a method for treating a complement-mediated disease or disorder. Further provided herein are conjugates comprising a humanized anti-factor Bb antibody for use in a method for treating a complement-mediated disease or disorder. Further still provided herein are pharmaceutical compositions comprising a humanized anti-factor Bb antibody for use in a method for treating a complement-mediated disease or disorder. Still further provided herein are devices comprising a humanized anti-factor Bb antibody for use in a method for treating a complement-mediated disease or disorder.

In some embodiments, a humanized anti-factor Bb antibody for use in a method for treating a complement-mediated disease or disorder comprises a $V_H$ comprising the amino acid sequence of SEQ ID NO: 19 and a $V_L$ comprising the amino acid sequence of SEQ ID NO: 27. In some embodiments, a humanized anti-factor Bb antibody for use in a method for treating a complement-mediated disease or disorder comprises a heavy chain comprising the amino acid sequence of SEQ ID NO: 34 and a light chain comprising the amino acid sequence of SEQ ID NO: 35.

In some embodiments, a humanized anti-factor Bb antibody for use in a method for treating a complement-mediated disease or disorder comprises a $V_H$ comprising the amino acid sequence of SEQ ID NO: 17 and a $V_L$ comprising the amino acid sequence of SEQ ID NO: 26. In some embodiments, a humanized anti-factor Bb antibody for use in a method for treating a complement-mediated disease or disorder comprises a heavy chain comprising the amino acid sequence of SEQ ID NO: 38 and a light chain comprising the amino acid sequence of SEQ ID NO: 39.

In some embodiments, a conjugate for use in a method for treating a complement-mediated disease or disorder comprises a humanized anti-factor Bb antibody comprising a $V_H$ comprising the amino acid sequence of SEQ ID NO: 19 and a $V_L$ comprising the amino acid sequence of SEQ ID NO: 27. In some embodiments, a conjugate for use in a method for treating a complement-mediated disease or disorder comprises a humanized anti-factor Bb antibody comprising a heavy chain comprising the amino acid sequence of SEQ ID NO: 34 and a light chain comprising the amino acid sequence of SEQ ID NO: 35.

In some embodiments, a conjugate for use in a method for treating a complement-mediated disease or disorder comprises a humanized anti-factor Bb antibody comprising a $V_H$ comprising the amino acid sequence of SEQ ID NO: 17 and a $V_L$ comprising the amino acid sequence of SEQ ID NO: 26. In some embodiments, a conjugate for use in a method for treating a complement-mediated disease or disorder comprises a humanized anti-factor Bb antibody comprising a heavy chain comprising the amino acid sequence of SEQ ID NO: 38 and a light chain comprising the amino acid sequence of SEQ ID NO: 39.

In some embodiments, a pharmaceutical composition for use in a method for treating a complement-mediated disease or disorder comprises a humanized anti-factor Bb antibody comprising a $V_H$ comprising the amino acid sequence of SEQ ID NO: 19 and a $V_L$ comprising the amino acid sequence of SEQ ID NO: 27. In some embodiments, a pharmaceutical composition for use in a method for treating a complement-mediated disease or disorder comprises a humanized anti-factor Bb antibody comprising a heavy chain comprising the amino acid sequence of SEQ ID NO: 34 and a light chain comprising the amino acid sequence of SEQ ID NO: 35.

In some embodiments, a pharmaceutical composition for use in a method for treating a complement-mediated disease or disorder comprises a humanized anti-factor Bb antibody comprising a $V_H$ comprising the amino acid sequence of SEQ ID NO: 17 and a $V_L$ comprising the amino acid sequence of SEQ ID NO: 26. In some embodiments, a pharmaceutical composition for use in a method for treating a complement-mediated disease or disorder comprises a humanized anti-factor Bb antibody comprising a heavy chain comprising the amino acid sequence of SEQ ID NO: 38 and a light chain comprising the amino acid sequence of SEQ ID NO: 39.

In some embodiments, a device for use in a method for treating a complement-mediated disease or disorder comprises a humanized anti-factor Bb antibody comprising a $V_H$ comprising the amino acid sequence of SEQ ID NO: 19 and a $V_L$ comprising the amino acid sequence of SEQ ID NO: 27. In some embodiments, a device for use in a method for treating a complement-mediated disease or disorder comprises a humanized anti-factor Bb antibody comprising a heavy chain comprising the amino acid sequence of SEQ ID NO: 34 and a light chain comprising the amino acid sequence of SEQ ID NO: 35.

In some embodiments, a device for use in a method for treating a complement-mediated disease or disorder comprises a humanized anti-factor Bb antibody comprising a $V_H$ comprising the amino acid sequence of SEQ ID NO: 17 and a $V_L$ comprising the amino acid sequence of SEQ ID NO: 26 In some embodiments, a device for use in a method for treating a complement-mediated disease or disorder comprises a humanized anti-factor Bb antibody comprising a heavy chain comprising the amino acid sequence of SEQ ID NO: 38 and a light chain comprising the amino acid sequence of SEQ ID NO: 39.

In some embodiments, the complement-mediated disease is selected from the group consisting of: IgA nephropathy (Berger's disease), atypical hemolytic uremic syndrome (aHUS), paroxysmal nocturnal hemoglobinuria (PNH), idiopathic thrombocytopenic purpura (ITP), thrombotic thrombocytopenic purpura (TTP), lupus nephritis, ANCA vasculitis, membranous nephropathy, C3 glomerulonephritis (C3GN), focal segmental glomerulosclerosis (FSGS), multiple sclerosis, macular degeneration, age-related macular degeneration (AMD), rheumatoid arthritis, antiphospholipid antibody syndrome, asthma, ischemia-reperfusion injury, Type II membranoproliferative GN, spontaneous fetal loss, Pauci-immune vasculitis, epidermolysis bullosa, recurrent fetal loss, and traumatic brain injury.

Also provided herein are humanized anti-factor Bb antibodies for use in a method for inhibiting a complement pathway activity (e.g., AP activity). Further provided herein are conjugates comprising a humanized anti-factor Bb antibody for use in a method for inhibiting a complement pathway activity (e.g., AP activity). Further still provided herein are pharmaceutical compositions comprising a humanized anti-factor Bb antibody for use in a method for inhibiting a complement pathway activity (e.g., AP activity). Still further provided herein are devices comprising a humanized anti-factor Bb antibody for use in a method for inhibiting a complement pathway activity (e.g., AP activity).

In some embodiments, a humanized anti-factor Bb antibody for use in a method for inhibiting a complement pathway activity (e.g., AP activity) comprises a $V_H$ comprising the amino acid sequence of SEQ ID NO: 19 and a $V_L$ comprising the amino acid sequence of SEQ ID NO: 27. In some embodiments, a humanized anti-factor Bb antibody for use in a method for inhibiting a complement pathway activity (e.g., AP activity) comprises a heavy chain comprising the amino acid sequence of SEQ ID NO: 34 and a light chain comprising the amino acid sequence of SEQ ID NO: 35.

In some embodiments, a humanized anti-factor Bb antibody for use in a method for inhibiting a complement pathway activity (e.g., AP activity) comprises a $V_H$ comprising the amino acid sequence of SEQ ID NO: 17 and a $V_L$ comprising the amino acid sequence of SEQ ID NO: 26. In some embodiments, a humanized anti-factor Bb antibody for use in a method for inhibiting a complement pathway activity (e.g., AP activity) comprises a heavy chain comprising the amino acid sequence of SEQ ID NO: 38 and a light chain comprising the amino acid sequence of SEQ ID NO: 39.

In some embodiments, a conjugate for use in a method for inhibiting a complement pathway activity (e.g., AP activity) comprises a humanized anti-factor Bb antibody comprising a $V_H$ comprising the amino acid sequence of SEQ ID NO: 19 and a $V_L$ comprising the amino acid sequence of SEQ ID NO: 27. In some embodiments, a conjugate for use in a method for inhibiting a complement pathway activity (e.g., AP activity) comprises a humanized anti-factor Bb antibody comprising a heavy chain comprising the amino acid sequence of SEQ ID NO: 34 and a light chain comprising the amino acid sequence of SEQ ID NO: 35.

In some embodiments, a conjugate for use in a method for inhibiting a complement pathway activity (e.g., AP activity) comprises a humanized anti-factor Bb antibody comprising a $V_H$ comprising the amino acid sequence of SEQ ID NO: 17 and a $V_L$ comprising the amino acid sequence of SEQ ID NO: 26. In some embodiments, a conjugate for use in a method for inhibiting a complement pathway activity (e.g., AP activity) comprises a humanized anti-factor Bb antibody comprising a heavy chain comprising the amino acid sequence of SEQ ID NO: 38 and a light chain comprising the amino acid sequence of SEQ ID NO: 39.

In some embodiments, a pharmaceutical composition for use in a method for inhibiting a complement pathway activity (e.g., AP activity) comprises a humanized anti-factor Bb antibody comprising a $V_H$ comprising the amino acid sequence of SEQ ID NO: 19 and a $V_L$ comprising the amino acid sequence of SEQ ID NO: 27. In some embodiments, a pharmaceutical composition for use in a method for inhibiting a complement pathway activity (e.g., AP activity) comprises a humanized anti-factor Bb antibody comprising a heavy chain comprising the amino acid sequence of SEQ ID NO: 34 and a light chain comprising the amino acid sequence of SEQ ID NO: 35.

In some embodiments, a pharmaceutical composition for use in a method for inhibiting a complement pathway activity (e.g., AP activity) comprises a humanized anti-factor Bb antibody comprising a $V_H$ comprising the amino acid sequence of SEQ ID NO: 17 and a $V_L$ comprising the amino acid sequence of SEQ ID NO: 26. In some embodiments, a pharmaceutical composition for use in a method for inhibiting a complement pathway activity (e.g., AP activity) comprises a humanized anti-factor Bb antibody comprising a heavy chain comprising the amino acid sequence of SEQ ID NO: 38 and a light chain comprising the amino acid sequence of SEQ ID NO: 39.

In some embodiments, a pharmaceutical composition for use in a method for inhibiting a complement pathway activity (e.g., AP activity) comprises a humanized anti-factor Bb antibody comprising a $V_H$ comprising the amino acid sequence of SEQ ID NO: 19 and a $V_L$ comprising the amino acid sequence of SEQ ID NO: 27. In some embodiments, a pharmaceutical composition for use in a method for inhibiting a complement pathway activity (e.g., AP activity) comprises a humanized anti-factor Bb antibody comprising a heavy chain comprising the amino acid sequence of SEQ ID NO: 34 and a light chain comprising the amino acid sequence of SEQ ID NO: 35.

In some embodiments, a pharmaceutical composition for use in a method for inhibiting a complement pathway activity (e.g., AP activity) comprises a humanized anti-factor Bb antibody comprising a $V_H$ comprising the amino acid sequence of SEQ ID NO: 17 and a $V_L$ comprising the amino acid sequence of SEQ ID NO: 26. In some embodiments, a pharmaceutical composition for use in a method for inhibiting a complement pathway activity (e.g., AP activity) comprises a humanized anti-factor Bb antibody comprising a heavy chain comprising the amino acid sequence of SEQ ID NO: 38 and a light chain comprising the amino acid sequence of SEQ ID NO: 39.

Also provided herein are nucleic acids or nucleic acid sets encoding or collectively encoding a humanized antibody described herein; vectors or vector sets comprising a nucleic acid or nucleic acid set described herein; cells expressing a humanized antibody, a nucleic acid or nucleic acid set, or a vector or vector set as described herein.

In some embodiments, a nucleic acid or nucleic acid set encodes or collectively encodes a humanized anti-factor Bb antibody that comprises a $V_H$ comprising the amino acid sequence of SEQ ID NO: 19 and a $V_L$ comprising the amino acid sequence of SEQ ID NO: 27. In some embodiments, a nucleic acid or nucleic acid set encodes or collectively encodes a humanized anti-factor Bb antibody that comprises a heavy chain comprising the amino acid sequence of SEQ ID NO: 34 and a light chain comprising the amino acid sequence of SEQ ID NO: 35.

In some embodiments, a nucleic acid or nucleic acid set encodes or collectively encodes a humanized anti-factor Bb antibody that comprises a $V_H$ comprising the amino acid sequence of SEQ ID NO: 17 and a $V_L$ comprising the amino acid sequence of SEQ ID NO: 26. In some embodiments, a nucleic acid or nucleic acid set encodes or collectively encodes a humanized anti-factor Bb antibody that comprises a heavy chain comprising the amino acid sequence of SEQ ID NO: 38 and a light chain comprising the amino acid sequence of SEQ ID NO: 39.

In some embodiments, a vector or vector set comprises a nucleic acid or nucleic acid set that encodes or collectively encodes a humanized anti-factor Bb antibody that comprises a $V_H$ comprising the amino acid sequence of SEQ ID NO: 19 and a $V_L$ comprising the amino acid sequence of SEQ ID NO: 27. In some embodiments, a vector or vector set comprises a nucleic acid or nucleic acid set that encodes or collectively encodes a humanized anti-factor Bb antibody that comprises a heavy chain comprising the amino acid sequence of SEQ ID NO: 34 and a light chain comprising the amino acid sequence of SEQ ID NO: 35.

In some embodiments, a vector or vector set comprises a nucleic acid or nucleic acid set that encodes or collectively encodes a humanized anti-factor Bb antibody that comprises a $V_H$ comprising the amino acid sequence of SEQ ID NO: 17 and a $V_L$ comprising the amino acid sequence of SEQ ID NO: 26. In some embodiments, a vector or vector set comprises a nucleic acid or nucleic acid set that encodes or collectively encodes a humanized anti-factor Bb antibody that comprises a heavy chain comprising the amino acid sequence of SEQ ID NO: 38 and a light chain comprising the amino acid sequence of SEQ ID NO: 39.

In some embodiments, a cell comprises a humanized anti-factor Bb antibody that comprises a $V_H$ comprising the amino acid sequence of SEQ ID NO: 19 and a $V_L$ comprising the amino acid sequence of SEQ ID NO: 27. In some embodiments, a cell comprises a humanized anti-factor Bb antibody that comprises a heavy chain comprising the amino acid sequence of SEQ ID NO: 34 and a light chain comprising the amino acid sequence of SEQ ID NO: 35.

In some embodiments, a cell comprises a humanized anti-factor Bb antibody that comprises a $V_H$ comprising the amino acid sequence of SEQ ID NO: 17 and a $V_L$ comprising the amino acid sequence of SEQ ID NO: 26. In some embodiments, a cell comprises a humanized anti-factor Bb antibody that comprises a heavy chain comprising the amino acid sequence of SEQ ID NO: 38 and a light chain comprising the amino acid sequence of SEQ ID NO: 39.

In some embodiments, a cell comprises a nucleic acid or nucleic acid set that encodes or collectively encodes a humanized anti-factor Bb antibody that comprises a $V_H$ comprising the amino acid sequence of SEQ ID NO: 19 and a $V_L$ comprising the amino acid sequence of SEQ ID NO: 27. In some embodiments, a cell comprises a nucleic acid or nucleic acid set that encodes or collectively encodes a humanized anti-factor Bb antibody that comprises a heavy chain comprising the amino acid sequence of SEQ ID NO: 34 and a light chain comprising the amino acid sequence of SEQ ID NO: 35.

In some embodiments, a cell comprises a nucleic acid or nucleic acid set that encodes or collectively encodes a humanized anti-factor Bb antibody that comprises a $V_H$ comprising the amino acid sequence of SEQ ID NO: 17 and a $V_L$ comprising the amino acid sequence of SEQ ID NO: 26. In some embodiments, a cell comprises a nucleic acid or nucleic acid set that encodes or collectively encodes a humanized anti-factor Bb antibody that comprises a heavy chain comprising the amino acid sequence of SEQ ID NO: 38 and a light chain comprising the amino acid sequence of SEQ ID NO: 39.

In some embodiments, a cell comprises a vector or vector set that comprises a nucleic acid or nucleic acid set that encodes or collectively encodes a humanized anti-factor Bb antibody that comprises a $V_H$ comprising the amino acid sequence of SEQ ID NO: 19 and a $V_L$ comprising the amino acid sequence of SEQ ID NO: 27. In some embodiments, a cell comprises a vector or vector set that comprises a nucleic acid or nucleic acid set that encodes or collectively encodes a humanized anti-factor Bb antibody that comprises a heavy chain comprising the amino acid sequence of SEQ ID NO: 34 and a light chain comprising the amino acid sequence of SEQ ID NO: 35.

In some embodiments, a cell comprises a vector or vector set that comprises a nucleic acid or nucleic acid set that encodes or collectively encodes a humanized anti-factor Bb antibody that comprises a $V_H$ comprising the amino acid sequence of SEQ ID NO: 17 and a $V_L$ comprising the amino acid sequence of SEQ ID NO: 26. In some embodiments, a cell comprises a vector or vector set that comprises a nucleic acid or nucleic acid set that encodes or collectively encodes a humanized anti-factor Bb antibody that comprises a heavy chain comprising the amino acid sequence of SEQ ID NO: 38 and a light chain comprising the amino acid sequence of SEQ ID NO: 39.

In some embodiments, a cell is a mammalian cell, for example, selected from the group consisting of human embryonic kidney (HEK) cells, Chinese hamster ovary (CHO) cells, NS0 myeloma cells, SP2 cells, COS cells, and mammary epithelial cells.

Other aspects of the present disclosure provide methods of producing a humanized antibody described herein, the methods comprising culturing a cell described herein to produce the humanized antibody. In some embodiments, a method further comprises isolating the humanized antibody.

In some embodiments, a method of producing a humanized anti-factor Bb antibody comprises culturing a cell that comprises a nucleic acid that encodes or nucleic acid set that collectively encodes a humanized anti-factor Bb antibody that comprises a $V_H$ comprising the amino acid sequence of SEQ ID NO: 19 and a $V_L$ comprising the amino acid sequence of SEQ ID NO: 27 to produce the humanized anti-factor Bb antibody. In some embodiments, a method of producing a humanized anti-factor Bb antibody comprises culturing a cell that comprises a nucleic acid that encodes or nucleic acid set that collectively encodes humanized anti-factor Bb antibody that comprises a heavy chain comprising the amino acid sequence of SEQ ID NO: 34 and a light chain comprising the amino acid sequence of SEQ ID NO: 35.

In some embodiments, a method of producing a humanized anti-factor Bb antibody comprises culturing a cell that comprises a nucleic acid that encodes or nucleic acid set that collectively encodes a humanized anti-factor Bb antibody that comprises a $V_H$ comprising the amino acid sequence of SEQ ID NO: 17 and a $V_L$ comprising the amino acid sequence of SEQ ID NO: 16 to produce the humanized anti-factor Bb antibody. In some embodiments, a method of producing a humanized anti-factor Bb antibody comprises culturing a cell that comprises a nucleic acid that encodes or nucleic acid set that collectively encodes humanized anti-factor Bb antibody that comprises a heavy chain comprising the amino acid sequence of SEQ ID NO: 28 and a light chain comprising the amino acid sequence of SEQ ID NO: 39.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

(FIG. 4A: Chimeric VH0/Vκ0, VH4/Vκ6; FIG. 4B: VH4/Vκ7, VH6/Vκ6; FIG. 4C: VH6/Vκ7, VH7/Vκ7.

DETAILED DESCRIPTION

Figure 1A:
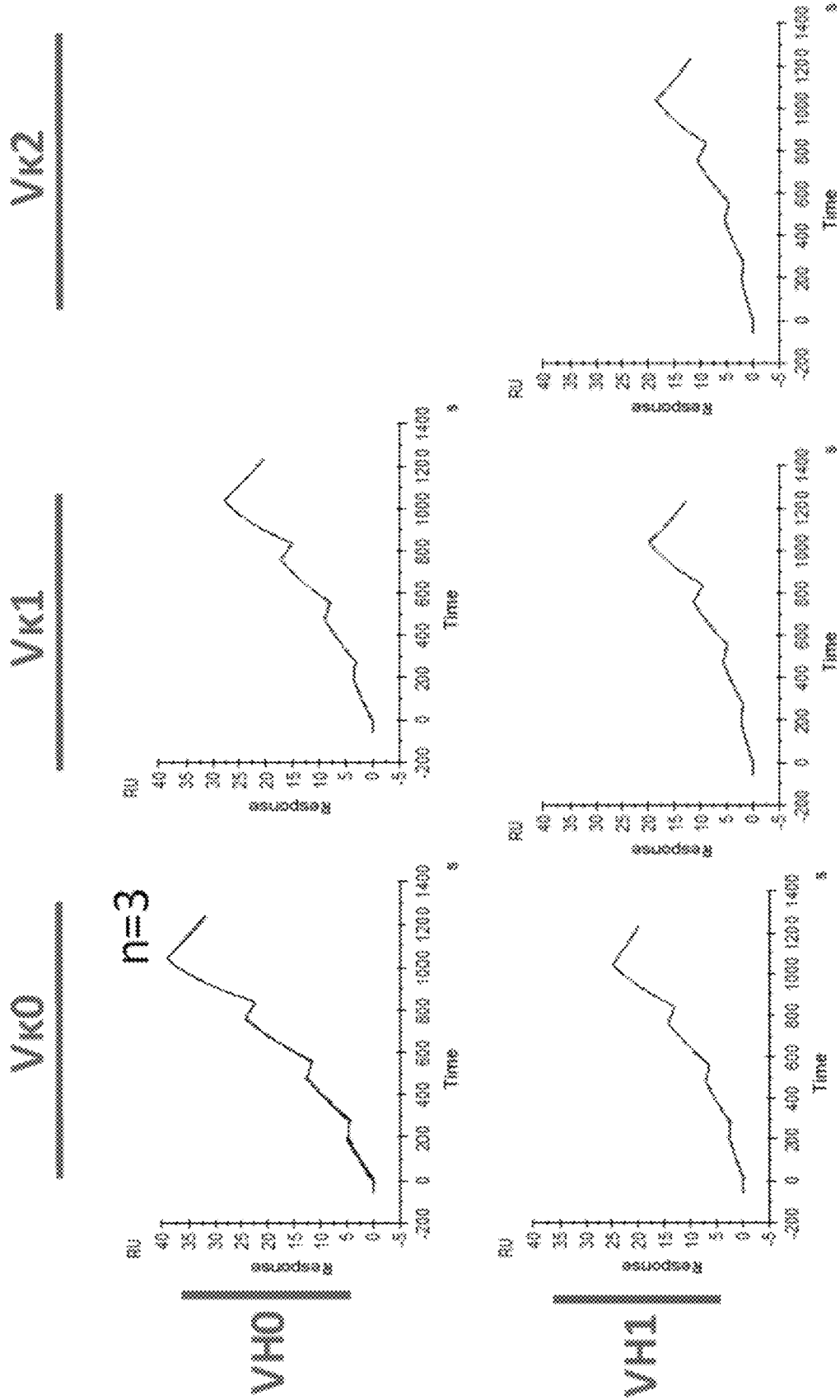
FIGS. 1A-1D show binding of humanized antibody variants (Group 1) to complement factor Bb (factor Bb) using single cycle kinetics. Raw sensorgrams and fitted curves (1:1 binding model) are shown for humanized variants and control antibodies binding to factor Bb. Kinetic analysis was carried out on a BIACORE™ T200. Each antibody was captured on a Protein A CM5 chip before increasing concentrations of factor Bb were injected and a single off-rate was determined. *Scales are identical for each section, and x is from −200 to 1400 and y from −5 to 40.
Figure 1B:
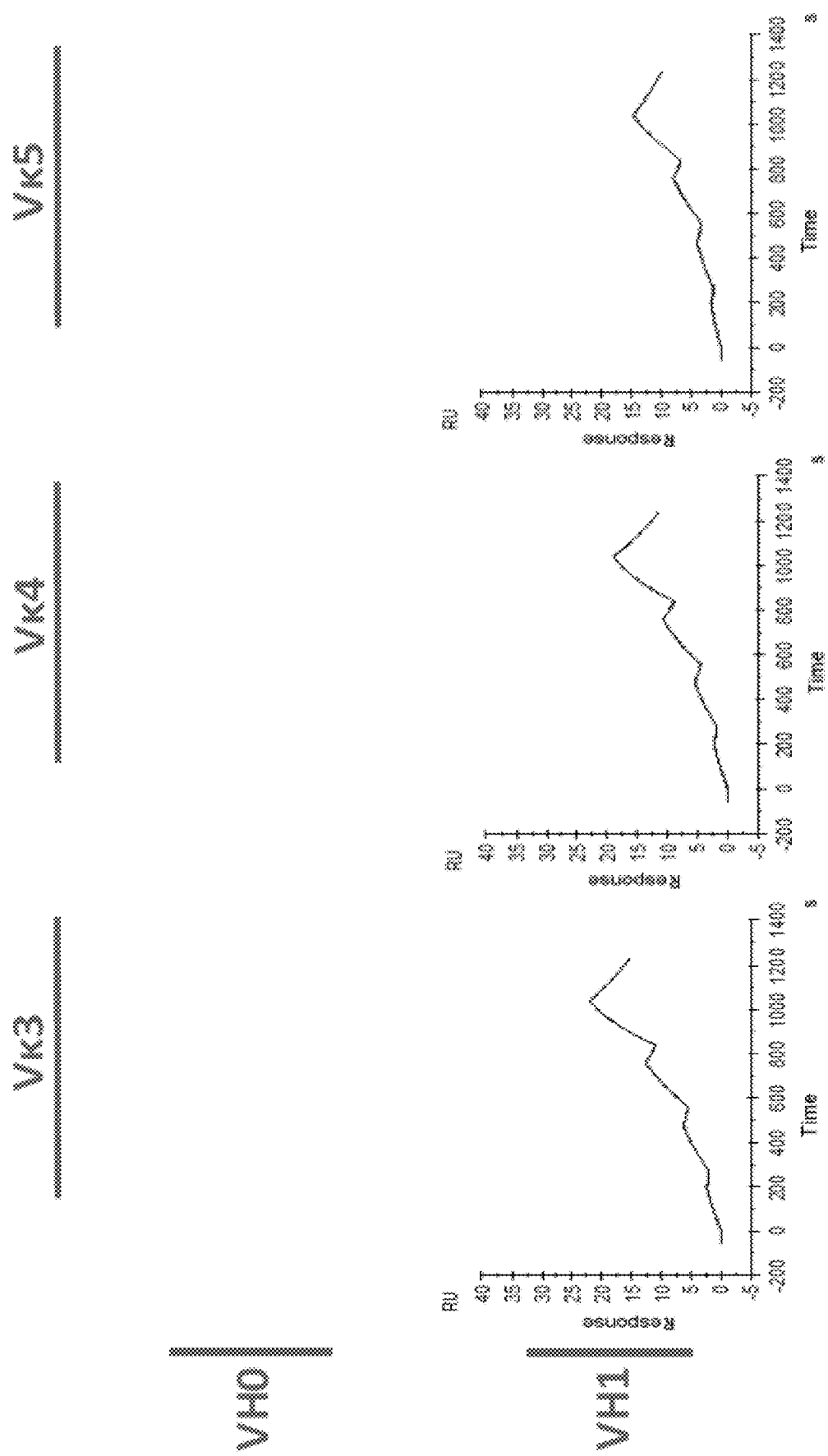
Figure 1C:
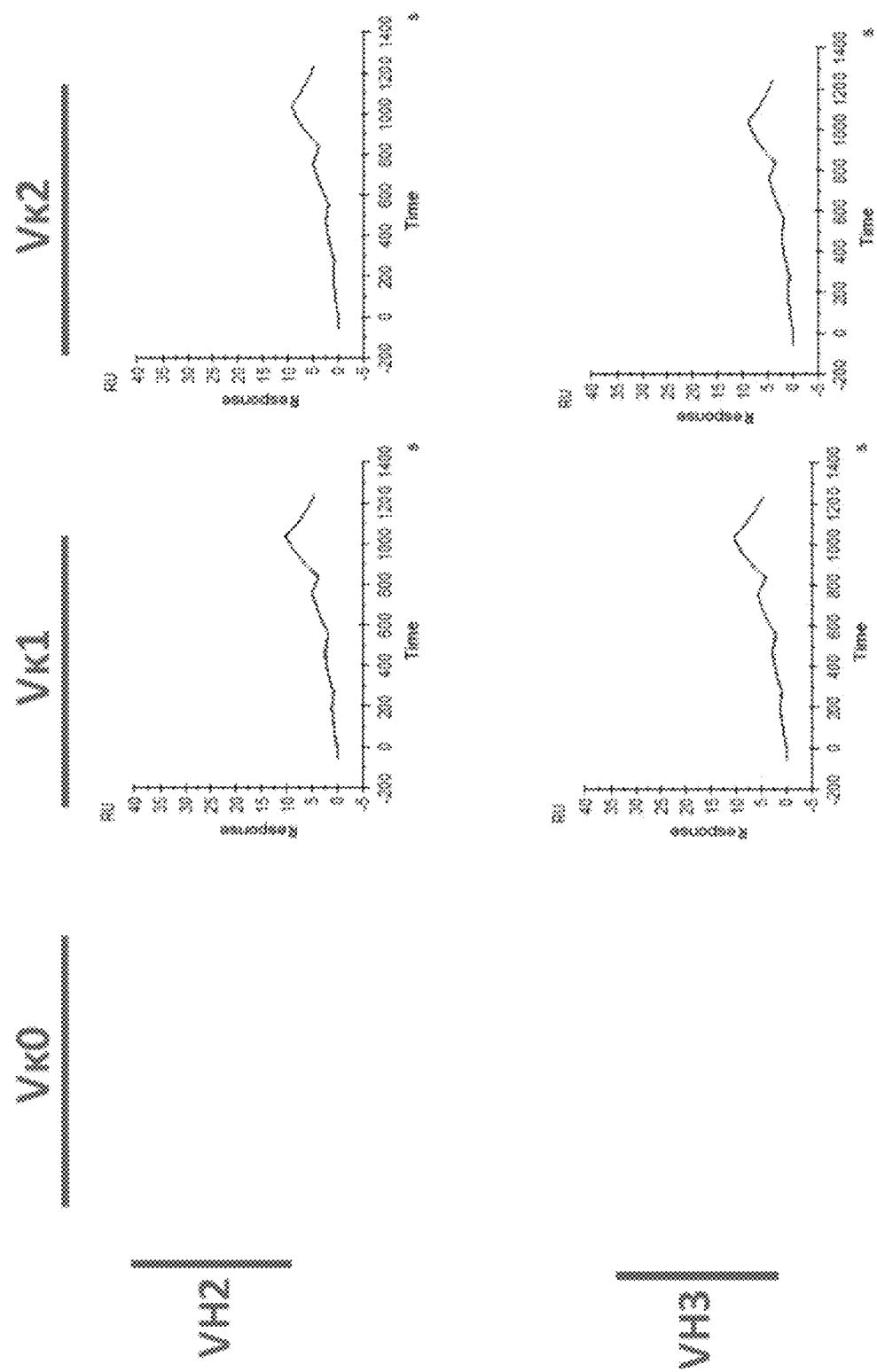
Figure 1D:
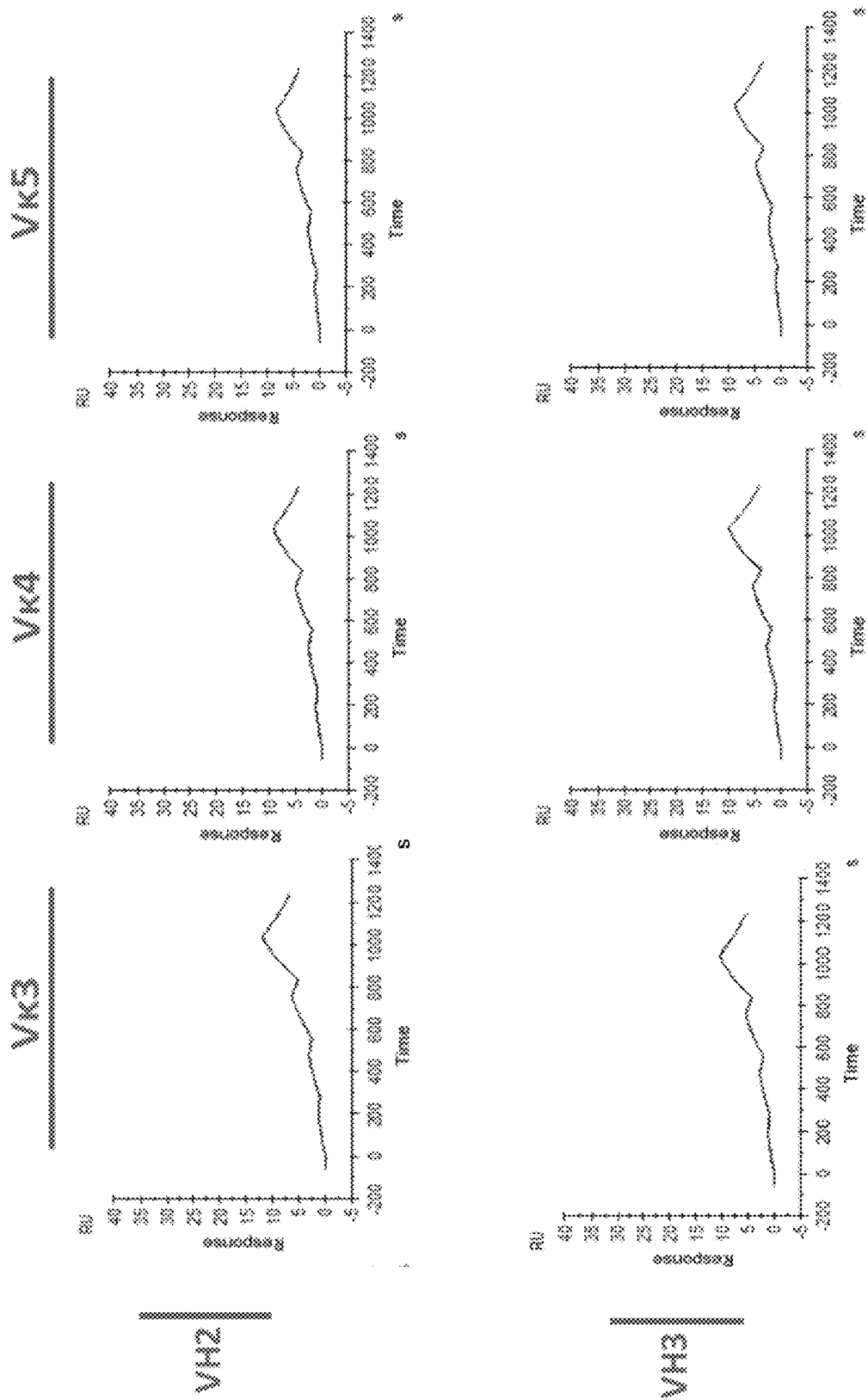

The present disclosure provides humanized antibodies that bind complement factor Bb protein. These antibodies are referred to herein as "humanized anti-factor Bb antibodies." The present disclosure also provides nucleic acids encoding humanized anti-factor Bb antibodies, compositions comprising the antibodies, methods of producing the antibodies (e.g., recombinant production methods), and methods of using the antibodies, such as methods of treating a (at least one) complement-mediated disease or disorder.

"Antibody" encompasses antibodies or immunoglobulins of any isotype, including but not limited to humanized antibodies and chimeric antibodies. An antibody may be a single-chain antibody (scAb) or a single domain antibody (dAb) (e.g., a single domain heavy chain antibody or a single domain light chain antibody; see Holt et al. (2003) *Trends Biotechnol.* 21:484). The term "antibody" also encompasses fragments of antibodies (antibody fragments) that retain specific binding to an antigen. "Antibody" further includes single-chain variable fragments (scFvs), which are fusion proteins of the variable regions of the heavy ($V_H$) and light chains ($V_L$) of antibodies, connected with a short linker peptide, and diabodies, which are noncovalent dimers of scFv fragments that include the $V_H$ and $V_L$ connected by a small peptide linker (Zapata et al., *Protein Eng.* 8(10): 1057-1062 (1995)). Other fusion proteins that comprise an antigen-binding portion of an antibody and a non-antibody protein are also encompassed by the term "antibody."

"Antibody fragments" comprise a portion of an intact antibody, for example, the antigen binding or variable region of the intact antibody. Examples of antibody fragments include an antigen-binding fragment (Fab), Fab', F(ab')2, a variable domain Fv fragment (Fv), an Fd fragment, and an antigen binding fragment of a chimeric antigen receptor.

Papain digestion of antibodies produces two identical antigen-binding fragments, referred to as "Fab" fragments, each with a single antigen-binding site, and a residual "Fc"

fragment, a designation reflecting the ability to crystallize readily. Pepsin treatment yields an F(ab')2 fragment that has two antigen combining sites and is still capable of cross-linking antigen.

"Fv" is the minimum antibody fragment that contains a complete antigen-recognition and -binding site. This region includes a dimer of one heavy-chain variable domain and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Fab" fragments contain the constant domain of the light chain and the first constant domain ($CH_1$) of the heavy chain. Fab fragments differ from Fab' fragments by the addition of a few residues at the carboxyl terminus of the heavy chain $CH_1$ domain including at least one cysteine from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"scFv" antibody fragments comprise the $V_H$ and $V_L$ of an antibody, wherein these regions are present in a single polypeptide chain. In some cases, the Fv polypeptide further comprises a polypeptide linker between the $V_H$ and $V_L$ regions, which enables the scFv to form the desired structure for antigen binding. For a review of scFv, see Pluckthun in *The Pharmacology of Monoclonal Antibodies*, vol. 113, Rosenburg and Moore eds., Springer-Verlag, New York, pp. 269-315 (1994).

"Diabody" refers to a small antibody fragment with two antigen-binding sites, which fragments comprise a $V_H$ connected to a $V_L$ in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, Hollinger et al. *Proc. Natl. Acad. Sci. USA* 90: 6444-6448 (1993).

An antibody can be monovalent or bivalent. An antibody can be an Ig monomer, which is a "Y-shaped" molecule that consists of four polypeptide chains: two heavy chains and two light chains connected by disulfide bonds.

Antibodies can be detectably labeled, e.g., with a radio-isotope, an enzyme that generates a detectable product, and/or a fluorescent protein. Antibodies can be further conjugated to other moieties, such as members of specific binding pairs, e.g., biotin member of biotin-avidin specific binding pair. Antibodies can also be bound to a solid support, including, but not limited to, polystyrene plates and/or beads.

An "isolated" antibody is one that has been identified and separated and/or recovered from a component of its natural environment (i.e., is not naturally occurring). Contaminant components of its natural environment are materials that would interfere with uses (e.g., diagnostic or therapeutic uses) of the antibody, and can include enzymes, hormones, and other proteinaceous or nonproteinaceous solutes. In some cases, an antibody is purified (1) to greater than 90%, greater than 95%, or greater than 98% by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or non-reducing conditions using Coomassie blue or silver stain. Isolated antibodies encompass antibodies in situ within recombinant cells, as at least one component of the antibody's natural environment will not be present. In some embodiments, an isolated antibody is prepared by at least one purification step.

A "monoclonal antibody" is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries).

A "complementarity determining region (CDR)" is the non-contiguous antigen combining sites found within the variable region of both heavy and light chain polypeptides. CDRs have been described by Lefranc et al. (2003) *Developmental and Comparative Immunology* 27:55; Kabat et al., *J. Biol. Chem.* 252:6609-6616 (1977); Kabat et al., U. S. Dept. of Health and Human Services, "*Sequences of proteins of immunological interest*" (1991); by Chothia et al., *J. Mol. Biol.* 196:901-917 (1987); and MacCallum et al., *J. Mol. Biol.* 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein.

As used herein, the terms "CDR-L1," "CDR-L2," and "CDR-L3" refer, respectively, to the first, second, and third CDRs in a light chain variable region. As used herein, the terms "CDR-H1", "CDR-H2", and "CDR-H3" refer, respectively, to the first, second, and third CDRs in a heavy chain variable region. As used herein, the terms "CDR-1", "CDR-2", and "CDR-3" refer, respectively, to the first, second and third CDRs of either chain's variable region.

A "framework" when used in reference to an antibody variable region includes all amino acid residues outside the CDR regions within the variable region of an antibody. A variable region framework is generally a discontinuous amino acid sequence that includes only those amino acids outside of the CDRs. A "framework region" includes each domain of the framework that is separated by the CDRs.

A "humanized antibody" is an antibody comprising portions of antibodies of different origin, wherein at least one portion comprises amino acid sequences of human origin. For example, the humanized antibody can comprise portions derived from an antibody of nonhuman origin with the requisite specificity, such as a mouse, and from antibody sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized antibody is an antibody containing at least one chain comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120, 694 B1; Neuberger, M. S. et al., WO 86/01533; Neuberger, M. S. et al., European Patent No. 0,194,276 B 1; Winter, U.S. Pat. No. 5,225,539; Winter, European Patent No. 0,239, 400 B 1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

In some embodiments, a humanized antibody is produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., *Nucl. Acids Res.*, 17: 5404 (1989)); Sato, K., et al., *Cancer Research*, 53: 851-856 (1993); Daugherty, B. L. et al., *Nucleic Acids Res.*, 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Humanized Anti-factor Bb Antibodies

The amino acid sequences of the mouse monoclonal anti-factor Bb antibody from which the humanized anti-factor Bb antibodies described herein are derived are provided in Table 1. In some embodiments, a humanized anti-factor Bb antibody comprises a framework region of the heavy chain variable region and/or the light chain variable region that include sequences derived from a human immunoglobulin framework.

TABLE 1

Mouse Monoclonal Anti-Factor Bb Antibody

| Ab | CDRs (Kabat) | CDRs (IMGT) | Variable regions (Kabat CDRs bolded, IMGT CDRs underlined) |
|---|---|---|---|
| Anti-factor Bb mouse monoclonal antibody | CDR-H1: NYAMS (SEQ ID NO: 1) CDR-H2: TISNRGSYTY YPDSVKG (SEQ ID NO: 2) CDR-H3: ERPMDY (SEQ ID NO: 3) | CDR-H1: GFTFSNYA (SEQ ID NO: 7) CDR-H2: ISNRGSYT (SEQ ID NO: 8) CDR-H3: ARERPMDY (SEQ ID NO: 9) | V$_H$ (also referred to as "VH0" herein): EVQLVESGGALVKPG GSLKLSCAASGFTFSN YAMSWVRQTPEKRLE WVATISNRGSYTYYP DSVKGRFTISRDNAK NTLYLQMSSLRSEDT ALYYCARERPMDYW GQGTSVTVSS (SEQ ID NO: 12) |
| | CDR-L1: KASQDVGTAVA (SEQ ID NO: 4) | CDR-L1: QDVGTA (SEQ ID NO: 10) | V$_L$ (also referred to as "Vκ0" herein): DIVMTQSHKFMSTSV GDRVSITCKASQDVG |

TABLE 1-continued

Mouse Monoclonal Anti-Factor Bb Antibody

| Ab | CDRs (Kabat) | CDRs (IMGT) | Variable regions (Kabat CDRs bolded, IMGT CDRs underlined) |
|---|---|---|---|
| | CDR-L2: WASTRHT (SEQ ID NO: 5) CDR-L3: HQHSSNPLT (SEQ ID NO: 6) | CDR-L2: WAS (SEQ ID NO: 11) CDR-L3: HQHSSNPLT (SEQ ID NO: 6) | TAVAWYQQKPGQSP KLLIYWASTRHTGVP DRFTGSGSGTDFTLTI TNVQSEDLAVYFCHQ HSSNPLTFGAGTKLE LK (SEQ ID NO: 13) |

In some embodiments, a humanized anti-factor Bb antibody described herein comprises a heavy chain complementarity determining region 1 (CDR-H1), a heavy chain complementarity determining region 2 (CDR-H2), and a heavy chain complementarity determining region 3 (CDR-H3) of a heavy chain variable region comprising the amino acid sequence of SEQ ID NO: 12. In some embodiments, a humanized anti-factor Bb antibody described herein comprises a light chain complementarity determining region 1 (CDR-L1), a light chain complementarity determining region 2 (CDR-L2), and a light chain complementarity determining region 3 (CDR-L3) of a light chain variable region comprising the amino acid sequence of SEQ ID NO: 13. In some embodiments, a humanized anti-factor Bb antibody further comprises a humanized heavy chain framework region and/or a humanized light chain framework region.

In some embodiments, according to the Kabat definition, a humanized anti-factor Bb antibody described herein comprises a CDR-H1 comprising the amino acid sequence of SEQ ID NO: 1, a CDR-H2 comprising the amino acid sequence of SEQ ID NO: 2, and a CDR-H3 comprising the amino acid sequence of SEQ ID NO: 3. In some embodiments, according to the Kabat definition, a humanized anti-factor Bb antibody described herein comprises a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6. In some embodiments, a humanized anti-factor Bb antibody further comprises a humanized heavy chain framework region and/or a humanized light chain framework region. In some embodiments, according to the IMGT definition, a humanized anti-factor Bb antibody described herein comprises a CDR-H1 comprising the amino acid sequence of SEQ ID NO: 7, a CDR-H2 comprising the amino acid sequence of SEQ ID NO: 8, and a CDR-H3 comprising the amino acid sequence of SEQ ID NO: 9. In some embodiments, according to the IMGT definition, a humanized anti-factor Bb antibody described herein comprises a CDR-L1 comprising the amino acid sequence of SEQ ID NO: 10, a CDR-L2 comprising the amino acid sequence of SEQ ID NO: 11, and a CDR-L3 comprising the amino acid sequence of SEQ ID NO: 6. In some embodiments, a humanized anti-factor Bb antibody further comprises a humanized heavy chain framework region and/or a humanized light chain framework region.

In some embodiments, a humanized anti-factor Bb antibody of the present disclosure comprises a V$_H$ containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the $V_H$ set forth in SEQ ID NO: 12. In some embodiments, the anti-factor Bb antibody of the present disclosure comprises a $V_L$ containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the $V_L$ set forth in SEQ ID NO: 13.

In some embodiments, a humanized anti-factor Bb antibody of the present disclosure comprises a $V_H$ comprising an amino acid sequence that is at least 80% (e.g., 80%, 85%, 90%, 95%, 98%, or 99%) identical to the $V_H$ as set forth in SEQ ID NO: 12. In some embodiments, the humanized anti-factor Bb of the present disclosure comprises a $V_L$ comprising an amino acid sequence that is at least 80% (e.g., 80%, 85%, 90%, 95%, 98%, or 99%) identical to the $V_L$ as set forth in SEQ ID NO: 13.

In some embodiments, a humanized anti-factor Bb antibody of the present disclosure comprises a humanized $V_H$ comprising a CDR-H1 having the amino acid sequence of SEQ ID NO: 1 (according to the Kabat definition system), a CDR-H2 having the amino acid sequence of SEQ ID NO: 2 (according to the Kabat definition system), a CDR-H3 having the amino acid sequence of SEQ ID NO: 3 (according to the Kabat definition system), and containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) in the framework regions as compared with the $V_H$ as set forth in SEQ ID NO: 12. In some embodiments, a humanized anti-factor Bb antibody of the present disclosure comprises a humanized $V_L$ comprising a CDR-L1 having the amino acid sequence of SEQ ID NO: 4 (according to the Kabat definition system), a CDR-L2 having the amino acid sequence of SEQ ID NO: 5 (according to the Kabat definition system), and a CDR-L3 having the amino acid sequence of SEQ ID NO: 6 (according to the Kabat definition system), and containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) in the framework regions as compared with the $V_L$ as set forth in SEQ ID NO: 13.

In some embodiments, a humanized anti-factor Bb antibody of the present disclosure comprises a humanized $V_H$ comprising a CDR-H1 having the amino acid sequence of SEQ ID NO: 1 (according to the Kabat definition system), a CDR-H2 having the amino acid sequence of SEQ ID NO: 2 (according to the Kabat definition system), a CDR-H3 having the amino acid sequence of SEQ ID NO: 3 (according to the Kabat definition system), wherein the framework regions of the $V_H$ are collectively at least 80% (e.g., 80%, 85%, 90%, 95%, 98%, or 99%) identical to the framework regions of the $V_H$ as set forth in SEQ ID NO: 12. In some embodiments, a humanized anti-factor Bb antibody of the present disclosure comprises a humanized $V_L$ comprising a CDR-L1 having the amino acid sequence of SEQ ID NO: 4 (according to the Kabat definition system), a CDR-L2 having the amino acid sequence of SEQ ID NO: 5 (according to the Kabat definition system), and a CDR-L3 having the amino acid sequence of SEQ ID NO: 6 (according to the Kabat definition system), wherein the framework regions of the $V_L$ are collectively at least 80% (e.g., 80%, 85%, 90%, 95%, 98%, or 99%) identical to the frame work regions of the $V_L$ as set forth in any one of SEQ ID NO: 13.

In some embodiments, a humanized anti-factor Bb antibody of the present disclosure comprises a humanized $V_H$ comprising a CDR-H1 having the amino acid sequence of SEQ ID NO: 7 (according to the IMGT definition system), a CDR-H2 having the amino acid sequence of SEQ ID NO: 8 (according to the IMGT definition system), a CDR-H3 having the amino acid sequence of SEQ ID NO: 9 (according to the IMGT definition system), and containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) in the framework regions as compared with the $V_H$ as set forth in SEQ ID NO: 12. In some embodiments, a humanized anti-factor Bb antibody of the present disclosure comprises a humanized $V_L$ comprising a CDR-L1 having the amino acid sequence of SEQ ID NO: 10 (according to the IMGT definition system), a CDR-L2 having the amino acid sequence of SEQ ID NO: 11 (according to the IMGT definition system), and a CDR-L3 having the amino acid sequence of SEQ ID NO: 6 (according to the IMGT definition system), and containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) in the framework regions as compared with the $V_L$ as set forth in SEQ ID NO: 13.

In some embodiments, a humanized anti-factor Bb antibody of the present disclosure comprises a humanized $V_H$ comprising a CDR-H1 having the amino acid sequence of SEQ ID NO: 7 (according to the IMGT definition system), a CDR-H2 having the amino acid sequence of SEQ ID NO: 8 (according to the IMGT definition system), a CDR-H3 having the amino acid sequence of SEQ ID NO: 9 (according to the IMGT definition system), wherein the framework regions of the $V_H$ collectively are at least 80% (e.g., 80%, 85%, 90%, 95%, 98%, or 99%) identical to the framework regions of the $V_H$ as set forth in SEQ ID NO: 12. In some embodiments, a humanized anti-factor Bb antibody of the present disclosure comprises a humanized $V_L$ comprising a CDR-L1 having the amino acid sequence of SEQ ID NO: 10 (according to the IMGT definition system), a CDR-L2 having the amino acid sequence of SEQ ID NO: 11 (according to the IMGT definition system), and a CDR-L3 having the amino acid sequence of SEQ ID NO: 6 (according to the IMGT definition system), wherein the framework region of the $V_L$ collectively are at least 80% (e.g., 80%, 85%, 90%, 95%, 98%, or 99%) identical to the framework regions of the $V_L$ as set forth in any one of SEQ ID NO: 13.

Examples of the amino acid sequences and DNA coding sequences of the humanized heavy chain variable regions of the humanized anti-factor Bb antibodies described herein are provided in Table 2. Examples of the amino acid sequences and DNA coding sequences of the humanized light chain variable regions of the humanized anti-factor Bb antibodies described herein are provided in Table 3.

TABLE 2

Examples of Humanized Heavy Chain Variable Regions

| Humanized VH | Amino Acid Sequence | DNA Sequence |
|---|---|---|
| $V_H1$ | EVQLVESGGGLVKP GGSLRLSCAASGFTF | GAGGTGCAGCTGGTGGAGTCTGGGGGAGGCCTGGTCAAG CCTGGGGGGTCCCTGAGACTCTCCTGTGCAGCCTCTGGAT |

TABLE 2-continued

Examples of Humanized Heavy Chain Variable Regions

| Humanized VH | Amino Acid Sequence | DNA Sequence |
|---|---|---|
| | SNYAMSWVRQAPG KGLEWVATISNRGS YTYYPDSVKGRFTI SRDNAKNSLYLQMS SLRSEDTALYYCAR ERPMDYWGQGTSV TVSS (SEQ ID NO: 14) | TCACCTTCAGTAACTATGCCATGTCTTGGGTCCGCCAGG CTCCAGGGAAGGGGCTGGAGTGGGTCGCAACCATTAGT AATCGTGGTAGTTACACCTACTACCCAGACTCAGTGA AGGGCCGATTCACCATCTCCAGAGACAACGCCAAGAACT CACTGTATCTGCAAATGAGCAGCCTGAGATCTGAGGACA CGGCTTTGTATTACTGTGCGAGAGAGAGGCCTATGGAC TACTGGGGCCAAGGAACCCTCAGTCACCGTCTCCTCA (SEQ ID NO: 41) |
| V$_H$2 | EVQLVESGGGLVKP GGSLRLSCAASGFTF SNYAMSWVRQAPG KGLEWVATISNRGS YTYYPDSVKGRFTI SRDNAKNSLYLQMN SLRAEDTALYYCAR ERPMDYWGQGTLV TVSS (SEQ ID NO: 15) | GAGGTGCAGCTGGTGGAGTCTGGGGGAGGCCTGGTCAAG CCTGGGGGGTCCCTGAGACTCTCCTGTGCAGCCTCTGGAT TCACCTTCAGTAACTATGCCATGTCTTGGGTCCGCCAGG CTCCAGGGAAGGGGCTGGAGTGGGTCGCAACCATTAGT AATCGTGGTAGTTACACCTACTACCCAGACTCAGTGA AGGGCCGATTCACCATCTCCAGAGACAACGCCAAGAACT CACTGTATCTGCAAATGAACAGCCTGAGAGCCGAGGACA CGGCTTTGTATTACTGTGCGAGAGAGAGGCCTATGGAC TACTGGGGCCAAGGAACCCTGGTCACCGTCTCCTCA (SEQ ID NO: 42) |
| V$_H$3 | EVQLVESGGGLVKP GGSLRLSCAASGFTF SNYAMSWVRQAPG KGLEWVATISNRGS YTYYADSVKGRFTI SRDNAKNSLYLQMN SLRAEDTALYYCAR ERPMDYWGQGTLV TVSS (SEQ ID NO: 16) | GAGGTGCAGCTGGTGGAGTCTGGGGGAGGCCTGGTCAAG CCTGGGGGGTCCCTGAGACTCTCCTGTGCAGCCTCTGGAT TCACCTTCAGTAACTATGCCATGTCTTGGGTCCGCCAGG CTCCAGGGAAGGGGCTGGAGTGGGTCGCAACCATTAGT AATCGTGGTAGTTACACCTACTACGCAGACTCAGTGA AGGGCCGATTCACCATCTCCAGAGACAACGCCAAGAACT CACTGTATCTGCAAATGAACAGCCTGAGAGCCGAGGACA CGGCTTTGTATTACTGTGCGAGAGAGAGGCCTATGGAC TACTGGGGCCAAGGAACCCTGGTCACCGTCTCCTCA (SEQ ID NO: 43) |
| V$_H$4 | EVQLVESGGGLVKP GGSLRLSCAASGFTF SNYAMSWVRQAPG KRLEWVATISNRGS YTYYPDSVKGRFTI SRDNAKNSLYLQMS SLRSEDTALYYCAR ERPMDYWGQGTSV TVSS (SEQ ID NO: 17) | GAGGTGCAGCTGGTGGAGTCTGGGGGAGGCCTGGTCAAG CCTGGGGGGTCCCTGAGACTCTCCTGTGCAGCCTCTGGAT TCACCTTCAGTAACTATGCCATGTCTTGGGTCCGCCAGG CTCCAGGGAAGAGGCTGGAGTGGGTCGCAACCATTAGT AATCGTGGTAGTTACACCTACTACCCAGACTCAGTGA AGGGCCGATTCACCATCTCCAGAGACAACGCCAAGAACT CACTGTATCTGCAAATGAGCAGCCTGAGATCTGAGGACA CGGCTTTGTATTACTGTGCGAGAGAGAGGCCTATGGAC TACTGGGGCCAAGGAACCCTCAGTCACCGTCTCCTCA (SEQ ID NO: 44) |
| V$_H$5 | EVQLVESGGGLVKP GGSLRLSCAASGFTF SNYAMSWVRQTPE KRLEWVATISNRGS YTYYPDSVKGRFTI SRDNAKNSLYLQMS SLRSEDTALYYCAR ERPMDYWGQGTSV TVSS (SEQ ID NO: 18) | GAGGTGCAGCTGGTGGAGTCTGGGGGAGGCCTGGTCAAG CCTGGGGGGTCCCTGAGACTCTCCTGTGCAGCCTCTGGAT TCACCTTCAGTAACTATGCCATGTCTTGGGTCCGCCAGA CTCCAGAGAAGAGGCTGGAGTGGGTCGCAACCATTAGT AATCGTGGTAGTTACACCTACTACCCAGACTCAGTGA AGGGCCGATTCACCATCTCCAGAGACAACGCCAAGAACT CACTGTATCTGCAAATGAGCAGCCTGAGATCTGAGGACA CGGCTTTGTATTACTGTGCGAGAGAGAGGCCTATGGAC TACTGGGGCCAAGGAACCCTCAGTCACCGTCTCCTCA (SEQ ID NO: 45) |
| V$_H$6 | EVQLVESGGGLVKP GGSLRLSCAASGFTF SNYAMSWVRQAPG KRLEWVATISNRGS YTYYPDSVKGRFTI SRDNAKNSLYLQMN SLRAEDTALYYCAR ERPMDYWGQGTLV TVSS (SEQ ID NO: 19) | GAGGTGCAGCTGGTGGAGTCTGGGGGAGGCCTGGTCAAG CCTGGGGGGTCCCTGAGACTCTCCTGTGCAGCCTCTGGAT TCACCTTCAGTAACTATGCCATGTCTTGGGTCCGCCAGG CTCCAGGGAAGAGGCTGGAGTGGGTCGCAACCATTAGT AATCGTGGTAGTTACACCTACTACCCAGACTCAGTGA AGGGCCGATTCACCATCTCCAGAGACAACGCCAAGAACT CACTGTATCTGCAAATGAACAGCCTGAGAGCCGAGGACA CGGCTTTGTATTACTGTGCGAGAGAGAGGCCTATGGAC TACTGGGGCCAAGGAACCCTGGTCACCGTCTCCTCA (SEQ ID NO: 46) |

TABLE 2-continued

Examples of Humanized Heavy Chain Variable Regions

| Humanized VH | Amino Acid Sequence | DNA Sequence |
| --- | --- | --- |
| V<sub>H</sub>7 | EVQLVESGGGLVKP GGSLRLSCAASGFT FSNYAMSWVRQTPE KRLEWVATISNRGS YTYYPDSVKGRFTI SRDNAKNSLYLQMN SLRAEDTALYYCAR ERPMDYWGQGTLV TVSS (SEQ ID NO: 20) | GAGGTGCAGCTGGTGGAGTCTGGGGGAGGCCTGGTCAAG CCTGGGGGGTCCCTGAGACTCTCCTGTGCAGCCTCTGGAT TCACCTTCAGTAACTATGCCATGTCTTGGGTCCGCCAGA CTCCAGAGAAGAGGCTGGAGTGGGTCGCAACCATTAGT AATCGTGGTAGTTACACCTACTACCCAGACTCAGTGA AGGGCCGATTCACCATCTCCAGAGACAACGCCAAGAACT CACTGTATCTGCAAATGAACAGCCTGAGAGCCGAGGACA CGGCTTTGTATTACTGTGCGAGAGAGAGGCCTATGGAC TACTGGGGCCAAGGAACCCTGGTCACCGTCTCCTCA (SEQ ID NO: 47) |

CDRs according to the Kabat definition are bolded in the amino acid and DNA sequences

TABLE 3

Examples of humanized light chain variable regions

| Humanized V<sub>L</sub> (Vκ) | Amino Acid Sequence | DNA Sequence |
| --- | --- | --- |
| Vκ1 | DIVMTQSPSFLSAS VGDRVTITCKASQ DVGTAVAWYQQK PGQPPKLLIYWAST RHTGVPDRFTGSG SGTDFTLTISSLQSE DFAVYFCHQHSSN PLTFGQGTKLEIK (SEQ ID NO: 21) | GACATCGTGATGACCCAGTCTCCATCCTTCCTGTCTGCATC TGTAGGAGACAGAGTCACCATCACTTGCAAGGCCAGTCA GGATGTGGGTACTGCTGTAGCCTGGTATCAGCAAAAAC CAGGGCAACCTCCTAAGCTCCTGATCTATTGGGCATCCAC TCGGCACACTGGGGTCCCAGATAGGTTCACAGGCAGTGG ATCTGGGACAGATTTCACTCTCACAATCAGCAGCCTGCAG TCTGAAGATTTTGCAGTTTATTTCTGTCACCAACATAGCA GCAATCCTCTCACGTTTGGCCAGGGGACCAAGCTGGAGA TCAAA (SEQ ID NO: 48) |
| Vκ2 | DIVMTQSPSTLSAS VGDRVTITCKASQ DVGTAVAWYQQK PGQPPKLLIYWAST RHTGVPDRFTGSG SGTDFTLTISSLQAE DFAVYFCHQHSSN PLTFGQGTKLEIK (SEQ ID NO: 22) | GACATCGTGATGACCCAGTCTCCATCCACCCTGTCTGCATC TGTAGGAGACAGAGTCACCATCACTTGCAAGGCCAGTCA GGATGTGGGTACTGCTGTAGCCTGGTATCAGCAAAAAC CAGGGCAACCTCCTAAGCTCCTGATCTATTGGGCATCCAC TCGGCACACTGGGGTCCCAGATAGGTTCACAGGCAGTGG ATCTGGGACAGATTTCACTCTCACAATCAGCAGCCTGCAG GCTGAAGATTTTGCAGTTTATTTCTGTCACCAACATAGCA GCAATCCTCTCACGTTTGGCCAGGGGACCAAGCTGGAGA TCAAA (SEQ ID NO: 49) |
| Vκ3 | DIQMTQSPSTLSAS VGDRVTITCKASQ DVGTAVAWYQQK PGQPPKLLIYWAST RHTGVPDRFSGSGS GTDFTLTISSLQAE DFAVYFCHQHSSN PLTFGQGTKLEIK (SEQ ID NO: 23) | GACATCCAGATGACCCAGTCTCCATCCACCCTGTCTGCAT CTGTAGGAGACAGAGTCACCATCACTTGCAAGGCCAGTC AGGATGTGGGTACTGCTGTAGCCTGGTATCAGCAAAAA CCAGGGCAACCTCCTAAGCTCCTGATCTATTGGGCATCCA CTCGGCACACTGGGGTCCCAGATAGGTTCAGCGGCAGTG GATCTGGGACAGATTTCACTCTCACAATCAGCAGCCTGCA GGCTGAAGATTTTGCAGTTTATTTCTGTCACCAACATAGC AGCAATCCTCTCACGTTTGGCCAGGGGACCAAGCTGGAG ATCAAA (SEQ ID NO: 50) |
| Vκ4 | DIQMTQSPSTLSAS VGDRVTITCRASQ DVGTAVAWYQQK PGQPPKLLIYWAST RHTGVPDRFSGSGS GTDFTLTISSLQAE DFAVYYCHQHSSN PLTFGQGTKLEIK (SEQ ID NO: 24) | GACATCCAGATGACCCAGTCTCCATCCACCCTGTCTGCAT CTGTAGGAGACAGAGTCACCATCACTTGCCGGGCCAGTC AGGATGTGGGTACTGCTGTAGCCTGGTATCAGCAAAAA CCAGGGCAACCTCCTAAGCTCCTGATCTATTGGGCATCCA CTCGGCACACTGGGGTCCCAGATAGGTTCAGCGGCAGTG GATCTGGGACAGATTTCACTCTCACAATCAGCAGCCTGCA GGCTGAAGATTTTGCAGTTTATTACTGTCACCAACATAGC AGCAATCCTCTCACGTTTGGCCAGGGGACCAAGCTGGAG ATCAAA (SEQ ID NO: 51) |
| Vκ5 | DIQMTQSPSTLSAS VGDRVTITCRASQ DVGTAVAWYQQK PGQPPKLLIYWAST RHTGVPDRFSGSGS GTDFTLTISSLQAE DFATYYCHQHSSN PLTFGQGTKLEIK (SEQ ID NO: 25) | GACATCCAGATGACCCAGTCTCCATCCACCCTGTCTGCAT CTGTAGGAGACAGAGTCACCATCACTTGCCGGGCCAGTC AGGATGTGGGTACTGCTGTAGCCTGGTATCAGCAAAAA CCAGGGCAACCTCCTAAGCTCCTGATCTATTGGGCATCCA CTCGGCACACTGGGGTCCCAGATAGGTTCAGCGGCAGTG GATCTGGGACAGATTTCACTCTCACAATCAGCAGCCTGCA GGCTGAAGATTTTGCAACTTATTACTGTCACCAACATAGC AGCAATCCTCTCACGTTTGGCCAGGGGACCAAGCTGGAG ATCAAA (SEQ ID NO: 52) |

TABLE 3-continued

Examples of humanized light chain variable regions

| Humanized $V_L$ (Vκ) | Amino Acid Sequence | DNA Sequence |
|---|---|---|
| Vκ6 | DIVMTQSPSFLSAS VGDRVTITCKASQ DVGTAVAWYQQK PGKAPKLL1YWAST RHTGVPDRFTGSG SGTDFTLTISSLQSE DFAVYFCHQHSSN PLTFGQGTKLEIK (SEQ ID NO: 26) | GACATCGTGATGACCCAGTCTCCATCCTTCCTGTCTGCATC TGTAGGAGACAGAGTCACCATCACTTGCAAGGCCAGTCA GGATGTGGGTACTGCTGTAGCCTGGTATCAGCAAAAAC CAGGGAAAGCCCCTAAGCTCCTGATCTATTGGGCATCCA CTCGGCACACTGGGGTCCCAGATAGGTTCACAGGCAGTG GATCATGGGACAGATTTCACTCTCACAATCAGCAGCCTGC AGTCTGAAGATTTTGCAGTTTATTTCTGTCACCAACATAG CAGCAATCCTCTCACGTTTGGCCAGGGGACCAAGCTGGA GATCAAA (SEQ ID NO: 53) |
| Vκ7 | DIQMTQSPSTLSAS VGDRVTITCKASQ DVGTAVAWYQQK PGKAPKLLIYWAST RHTGVPDRFSGSGS GTDFTLTISSLQAE DFAVYFCHQHSSN PLTFGQGTKLEIK (SEQ ID NO: 27) | GACATCCAGATGACCCAGTCTCCATCCACCCTGTCTGCAT CTGTAGGAGACAGAGTCACCATCACTTGCAAGGCCAGTC AGGATGTGGGTACTGCTGTAGCCTGGTATCAGCAAAAA CCAGGGAAAGCCCCTAAGCTCCTGATCTATTGGGCATCC ACTCGGCACACTGGGGTCCCAGATAGGTTCAGCGGCAGT GGATCTGGGACAGATTTCACTCTCACAATCAGCAGCCTGC AGGCTGAAGATTTTGCAGTTTATTTCTGTCACCAACATAG CAGCAATCCTCTCACGTTTGGCCAGGGGACCAAGCTGGA GATCAAA (SEQ ID NO: 54) |

CDRs according to the Kabat definition are bolded in the amino acid and DNA sequences In some embodiments, a humanized anti-factor Bb antibody of the present disclosure comprises a humanized $V_H$ comprising a CDR-H1 having the amino acid sequence of SEQ ID NO: 1 (according to the Kabat definition system), a CDR-H2 having the amino acid sequence of SEQ ID NO: 2 (according to the Kabat definition system), a CDR-H3 having the amino acid sequence of SEQ ID NO: 3 (according to the Kabat definition system), and containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) in the framework regions as compared with the $V_H$ as set forth in any one of SEQ ID NOs: 14-20. In some embodiments, a humanized anti-factor Bb antibody of the present disclosure comprises a humanized $V_L$ comprising a CDR-L1 having the amino acid sequence of SEQ ID NO: 4 (according to the Kabat definition system), a CDR-L2 having the amino acid sequence of SEQ ID NO: 5 (according to the Kabat definition system), and a CDR-L3 having the amino acid sequence of SEQ ID NO: 6 (according to the Kabat definition system), and containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) in the framework regions as compared with the $V_L$ as set forth in any one of SEQ ID NOs: 21-27.

In some embodiments, a humanized anti-factor Bb antibody of the present disclosure comprises a humanized $V_H$ comprising a CDR-H1 having the amino acid sequence of SEQ ID NO: 1 (according to the Kabat definition system), a CDR-H2 having the amino acid sequence of SEQ ID NO: 2 (according to the Kabat definition system), a CDR-H3 having the amino acid sequence of SEQ ID NO: 3 (according to the Kabat definition system), wherein the framework regions of the $V_H$ are collectively at least 80% (e.g., 80%, 85%, 90%, 95%, 98%, or 99%) identical to the framework regions of the $V_H$ as set forth in any one of SEQ ID NOs: 14-20. In some embodiments, a humanized anti-factor Bb antibody of the present disclosure comprises a humanized $V_L$ comprising a CDR-L1 having the amino acid sequence of SEQ ID NO: 4 (according to the Kabat definition system), a CDR-L2 having the amino acid sequence of SEQ ID NO: 5 (according to the Kabat definition system), and a CDR-L3 having the amino acid sequence of SEQ ID NO: 6 (according to the Kabat definition system), wherein the framework regions of the $V_L$ are collectively at least 80% (e.g., 80%, 85%, 90%, 95%, 98%, or 99%) identical to the framework regions of the $V_L$ as set forth in any one of SEQ ID NOs: 21-27.

In some embodiments, a humanized anti-factor Bb antibody of the present disclosure comprises a humanized $V_H$ comprising a CDR-H1 having the amino acid sequence of SEQ ID NO: 7 (according to the IMGT definition system), a CDR-H2 having the amino acid sequence of SEQ ID NO: 8 (according to the IMGT definition system), a CDR-H3 having the amino acid sequence of SEQ ID NO: 9 (according to the IMGT definition system), and containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) in the framework region as compared with the $V_H$ as set forth in any one of SEQ ID NOs: 14-20. In some embodiments, a humanized anti-factor Bb antibody of the present disclosure comprises a humanized $V_L$ comprising a CDR-L1 having the amino acid sequence of SEQ ID NO: 10 (according to the IMGT definition system), a CDR-L2 having the amino acid sequence of SEQ ID NO: 11 (according to the IMGT definition system), and a CDR-L3 having the amino acid sequence of SEQ ID NO: 6 (according to the IMGT definition system), and containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) in the framework region as compared with the $V_L$ as set forth in any one of SEQ ID NOs: 21-27.

In some embodiments, a humanized anti-factor Bb antibody of the present disclosure comprises a humanized $V_H$ comprising a CDR-H1 having the amino acid sequence of SEQ ID NO: 7 (according to the IMGT definition system), a CDR-H2 having the amino acid sequence of SEQ ID NO: 8 (according to the IMGT definition system), a CDR-H3 having the amino acid sequence of SEQ ID NO: 9 (according to the IMGT definition system), wherein the framework region of the $V_H$ is at least 80% (e.g., 80%, 85%, 90%, 95%, 98%, or 99%) identical to the framework regions of the $V_H$ as set forth in any one of SEQ ID NOs: 14-20. In some embodiments, a humanized anti-factor Bb antibody of the present disclosure comprises a humanized $V_L$ comprising a CDR-L1 having the amino acid sequence of SEQ ID NO: 10 (according to the IMGT definition system), a CDR-L2 having the amino acid sequence of SEQ ID NO: 11 (according to the IMGT definition system), and a CDR-L3 having the amino acid sequence of SEQ ID NO: 6 (according to the IMGT definition system), wherein the framework region of the $V_L$ are collectively at least 80% (e.g., 80%, 85%, 90%, 95%, 98%, or 99%) identical to the framework regions of the $V_L$ as set forth in any one of SEQ ID NOs: 21-27.

In some embodiments, a humanized anti-factor Bb antibody of the present disclosure comprises a humanized $V_H$ as set forth in any one of SEQ ID NOs: 14-20. In some embodiments, a humanized anti-factor Bb antibody of the present disclosure comprises a humanized $V_L$ as set forth in any one of SEQ ID NOs: 21-27. Table 4 provides examples of humanized anti-factor Bb antibodies comprising one of the humanized $V_H$ s provided in Table 2 and one of the humanized $V_L$s provided in Table 3.

TABLE 4

Examples of Variable Regions of Humanized Anti-factor Bb Antibodies

| Antibody | Variably Region Amino Acid Sequence |
|---|---|
| $V_H6/V\kappa7$ | $V_H$:<br>EVQLVESGGGLVKPGGSLRLSCAASGFTFSNYAMSWVRQAPGKRLEWVATISNRGSYT YYPDSVKGRFTISRDNAKNSLYLQMNSLRAEDTALYYCARERPMDYWGQGTLVTVSS (SEQ ID NO: 19)<br><br>$V_L$:<br>DIQMTQSPSTLSASVGDRVTITCKASQDVGTAVAWYQQKPGKAPKLUYWASTRHTGV PDRFSGSGSGTDITLTISSLQAEDFAVYFCHQHSSNPLTFGQGTKLEIK (SEQ ID NO: 27) |
| $V_H4/V\kappa6$ | $V_H$:<br>EVQLVESGGGLVKPGGSLRLSCAASGFTESNYAMSWVRQAPGKRLEWVATISNRGSYT YYPDSVKGRITISRDNAKNSLYLQMSSLRSEDTALYYCARERPMDYWGQGTSVTVSS (SEQ ID NO: 17)<br><br>$V_L$:<br>DIVMTQSPSFLSASVGDRVTITCKASQDVGTAVAWYQQKPGKAPKLLIYWASTRHTGV PDRFTGSGSGTDFTLTISSLQSEDFAVYFCHQHSSNPLTFGQGTKLEIK (SEQ ID NO: 26) |
| $V_H6/V\kappa6$ | $V_H$:<br>EVQLVESGGGLVKPGGSLRLSCAASGFTFSNYAMSWVRQAPGKRLEWVATISNRGSYT YYPDSVKGRFTISRDNAKNSLYLQMNSLRAEDTALYYCARERPMDYWGQGTLVTVSS (SEQ ID NO: 19)<br><br>$V_L$:<br>DIVMTQSPSFLSASVGDRVTITCKASQDVGTAVAWYQQKPGKAPKLLIYWASTRHTGV PDRFTGSGSGTDFTLTISSLQSEDFAVYFCHQHSSNPLTFGQGTKLEIK (SEQ ID NO: 26) |
| $V_H4/V\kappa7$ | $V_H$:<br>EVQLVESGGGLVKPGGSLRLSCAASGFTFSNYAMSWVRQAPGKRLEWVATISNRGSYT YYPDSVKGRFTISRDNAKNSLYLQMSSLRSEDTALYYCARERPMDYWGQGTSVTVSS (SEQ ID NO: 17)<br><br>$V_L$:<br>DIQ.MTQSPSTLSASVGDRVTITCKASQDVGTAVAWYQQKPGKAPKLLIYWASTRHTGV PDRFSGSGSGTDFTLTISSLQAEDFAVYFCHQHSSNPLTFGQGTKLEIK (SEQ ID NO: 27) |
| $V_H7/V\kappa7$ | $V_H$:<br>EVQLVESGGGLVKPGGSLRLSCAASGFTFSNYAMSWVRQTPEKRLEWVATISNRGSYT YYPDSVKGRFTISRDNAKNSLYLQMNSLRAEDTALYYCARERPMDYWGQGTLVTVSS (SEQ ID NO: 20)<br><br>$V_L$:<br>DIQMTQSPSTLSASVGDRVTITCKASQDVGTAVAWYQQKPGKAPKLLIYWASTRHTGV PDRFSGSGSGTDITLTISSLQAEDFAVYFCHQHSSNPETFGQGTKLEIK (SEQ ID NO: 27) |
| $V_H1/V\kappa1$ | $V_H$:<br>EVQLVESGGGLVKPGGSLRLSCAASGFTFSNYAMSWVRQAPGKGLEWVATISNRGSYT YYPDSVKGRITISRDNAKNSLYLQMSSLRSEDTALYYCARERPMDYWGQGTSVTVSS (SEQ ID NO: 14)<br><br>$V_L$:<br>DIVMTQSPSFLSASVGDRVTITCKASQDVGTAVAWYQQKPGQPPKLLIYWASTRHTGVP DRFTGSGSGTDFTLTISSLQSEDFAVYFCHQHSSNPLTFGQGTKLEIK (SEQ ID NO: 21) |
| $V_H1/V\kappa2$ | $V_H$:<br>EVQLVESGGGLVKPGGSLRLSCAASGFTFSNYAMSWVRQAPGKGLEWVATISNRGSYT YYPDSVKGRFTISRDNAKNSLYLQMSSLRSEDTALYYCARERPMDYWGQGTSVTVSS (SEQ ID NO: 14)<br><br>$V_L$:<br>DIVMTQSPSTLSASVGDRVTITCKASQDVGTAVAWYQQKPGQPPKLLIYWASTRHTGV PDRFTGSGSGTDFTLTISSLQAEDFAVYFCHQHSSNPLTFGQGTKLEIK (SEQ ID NO: 22) |

TABLE 4-continued

Examples of Variable Regions of Humanized Anti-factor Bb Antibodies

| Antibody | Variably Region Amino Acid Sequence |
|---|---|
| $V_H1/V\kappa3$ | $V_H$:<br>EVQLVESGGGLVKPGGSLRLSCAASGFTFSNYAMSWVRQAPGKGLEWVATISNRGSYT YYPDSVKGRFTISRDNAKNSLYLQMSSLRSEDTALYYCARERPMDYWGQGTSVTVSS<br>(SEQ ID NO: 14)<br><br>$V_L$:<br>DIQMTQSPSTLSASVGDRVTITCKASQDVGTAVAWYQQKPGQPPKLLIYWASTRHTGV PDRFSGSGSGTDFTLTISSLQAEDFAVYFCHQHSSNPLTFGQGTKLEIK (SEQ ID NO: 23) |
| $V_H1/V\kappa4$ | $V_H$:<br>EVQLVESGGGLVKPGGSLRLSCAASGFTFSNYAMSWVRQAPGKGLEWVATISNRGSYT YYPDSVKGRITISRDNAKNSLYLQMSSLRSEDTALYYCARERPMDYWGQGTSVTVSS<br>(SEQ ID NO: 14)<br><br>$V_L$:<br>DIQMTQSPSTLSASVGDRVTITCRASQDVGTAVAWYQQKPGQPPKLLIYWASTRHTGVP DRFSGSGSGTDFTLTISSLQAEDFAVYYCHQHSSNPLTFGQGTKLEIK (SEQ ID NO: 24) |
| $V_H1/V\kappa5$ | $V_H$:<br>EVQLVESGGGLVKPGGSLRLSCAASGFTFSNYAMSWVRQAPGKGLEWVATISNRGSYT YYPDSVKGRITISRDNAKNSLYLQMSSLRSEDTALYYCARERPMDYWGQGTSVTVSS<br>(SEQ ID NO: 14)<br><br>$V_L$:<br>DIQMTQSPSTLSASVGDRVTITCRASQDVGTAVAWYQQKPGQPPKLLIYWASTRHTGVP DRFSGSGSGTDFTLTISSLQAEDFATYYCHQHSSNPLTFGQGTKLEIK (SEQ ID NO: 25) |

CDRs according to the Kabat definition are bolded in the amino acid sequences

In some embodiments, a humanized anti-factor Bb antibody of the present disclosure comprises a humanized $V_H$ comprising the amino acid sequence of SEQ ID NO: 19 and a humanized $V_L$ comprising the amino acid sequence of SEQ ID NO: 27.

In some embodiments, a humanized anti-factor Bb antibody of the present disclosure comprises a humanized $V_H$ comprising the amino acid sequence of SEQ ID NO: 17 and a humanized $V_L$ comprising the amino acid sequence of SEQ ID NO: 26.

In some embodiments, a humanized anti-factor Bb antibody of the present disclosure comprises a humanized $V_H$ comprising the amino acid sequence of SEQ ID NO: 19 and a humanized $V_L$ comprising the amino acid sequence of SEQ ID NO: 26.

In some embodiments, a humanized anti-factor Bb antibody of the present disclosure comprises a humanized $V_H$ comprising the amino acid sequence of SEQ ID NO: 17 and a humanized $V_L$ comprising the amino acid sequence of SEQ ID NO: 27.

In some embodiments, a humanized anti-factor Bb antibody of the present disclosure comprises a humanized $V_H$ comprising the amino acid sequence of SEQ ID NO: 20 and a humanized $V_L$ comprising the amino acid sequence of SEQ ID NO: 27.

In some embodiments, a humanized anti-factor Bb antibody of the present disclosure comprises a humanized $V_H$ comprising the amino acid sequence of SEQ ID NO: 14 and a humanized $V_L$ comprising the amino acid sequence of any one of SEQ ID NOs: 21.

In some embodiments, a humanized anti-factor Bb antibody of the present disclosure comprises a humanized $V_H$ comprising the amino acid sequence of SEQ ID NO: 14 and a humanized $V_L$ comprising the amino acid sequence of any one of SEQ ID NOs: 22.

In some embodiments, a humanized anti-factor Bb antibody of the present disclosure comprises a humanized $V_H$ comprising the amino acid sequence of SEQ ID NO: 14 and a humanized $V_L$ comprising the amino acid sequence of any one of SEQ ID NOs: 23.

In some embodiments, a humanized anti-factor Bb antibody of the present disclosure comprises a humanized $V_H$ comprising the amino acid sequence of SEQ ID NO: 14 and a humanized $V_L$ comprising the amino acid sequence of any one of SEQ ID NOs: 24.

In some embodiments, a humanized anti-factor Bb antibody of the present disclosure comprises a humanized $V_H$ comprising the amino acid sequence of SEQ ID NO: 14 and a humanized $V_L$ comprising the amino acid sequence of any one of SEQ ID NOs: 25.

In some embodiments, a humanized anti-factor Bb antibody described herein is a full-length IgG, an Ig monomer, a Fab fragment, a F(ab')2 fragment, a scFv, a scAb, or a Fv. In some embodiments, a humanized anti-factor Bb antibody described herein is a full-length IgG. In some embodiments, the heavy chain of any of the humanized anti-factor Bb antibodies as described herein comprises a heavy chain constant region (CH) or a portion thereof (e.g., CH1, CH2, CH3, or a combination thereof). The heavy chain constant region can of any suitable origin, e.g., human, mouse, rat, or rabbit. In some embodiments, the heavy chain constant region is from a human IgG (a gamma heavy chain), e.g., IgG1, IgG2, or IgG4.

In some embodiments, mutations can be introduced into the heavy chain constant region of any one of the humanized anti-factor Bb antibodies described herein. In some embodiments, one, two or more mutations (e.g., amino acid substitutions) are introduced into the heavy chain constant region (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) *PNAS* 109: 6181-6186, U.S. Pat. No. 6,737,056, and International Publication Nos. WO 02/060919; WO 98/23289; and WO 97/34631, which are incorporated herein by reference.

In some embodiments, one, two or more mutations (e.g., amino acid substitutions) are introduced into the hinge region of the heavy chain constant region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more amino acid mutations (i.e., substitutions, insertions or deletions) are introduced into an IgG constant domain, or FcRn-binding fragment thereof to alter (e.g., decrease or increase) half-life of the antibody in vivo. In some embodiments, the one or more mutations are introduced into an Fc or hinge-Fc domain fragment. See, e.g., International Publication Nos. WO 02/060919; WO 98/23289; and WO 97/34631; and U.S. Pat. Nos. 5,869,046; 6,121,022; 6,277,375; and 6,165,745 for examples of mutations that will alter (e.g., decrease or increase) the half-life of an antibody in vivo.

In some embodiments, the constant region antibody described herein is an IgG1 constant region and comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) *J Biol Chem* 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat. Additional mutations that may be introduced to the heavy chain constant region that would increase the half-life of the antibody are known in the art, e.g., the M428L/N434S (EU numbering; M459L/N466S Kabat numbering) mutations as described in Zalevsky et al., *Nat Biotechnol.* 2010 February; 28(2): 157-159.

In some embodiments, one, two or more amino acid substitutions are introduced into an IgG constant domain Fc region to alter the effector function(s) of the antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, at least one amino acid substitutions may be introduced into the Fc region of an antibody described herein to remove potential glycosylation sites on Fc region, which may reduce Fc receptor binding (see, e.g., Shields R L et al., (2001) *J Biol Chem* 276: 6591-604).

In some embodiments, at least one amino acid in the constant region can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.). In some embodiments, at least one amino acid residue in the N-terminal region of the CH2 domain of an antibody described herein is altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or to increase the affinity of the antibody for an Fcγ receptor. This approach is described further in International Publication No. WO 00/42072.

In some embodiments, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," *Mol Immunol* 30, 105-108; 1993), where serine 228 (EU numbering; residue 241 Kabat numbering) is converted to proline resulting in an IgG1-like hinge sequence. In some embodiments, to reduce residual antibody-dependent cellular cytotoxicity, a L235E (EU numbering, corresponding to L248E in Kabat numbering) mutation is introduced to the heavy chain constant region, e.g., as described in Benhnia et al., *JOURNAL OF VIROLOGY*, Dec. 2009, p. 12355-12367.

In some embodiments, the heavy chain constant region in any one of the humanized anti-factor Bb antibodies described herein is an IgG4 constant region, or a variant there of. Examples of IgG4 constant regions and variants are provided in Table 5.

TABLE 5

Examples of Heavy Chain Constant Regions

| Heavy Chain Constant Region | Amino Acid Sequence |
|---|---|
| IgG4 constant region WT (also referred to herein as "IgG4wt") | ASTKGPSVFPLAPCSRSTSE STAALGCLVKDYFPEPVTVS WNSGALTSGVHTFPAVLQSS GLYSLSSVVTVPSSSLGTKT YTCNVDHKPSNTKVDKRVES KYGPPCPSCPAPEFLGGPSV FLFPPKPKDTLMISRTPEVT CVVVDVSQEDPEVQFNWYVD GVEVHNAKTKPREEQFNSTY RVVSVLTVLHQDWLNGKEYK CKVSNKGLPSSIEKTISKAK GQPREPQVYTLPPSQEEMTK NQVSLTCLVKGFYPSDIAVE WESNGQPENNYKTTPPVLDS DGSFFLYSRLTVDKSRWQEG NVFSCSVMHEALHNHYTQKS LSLSLGK (SEQ ID NO: 28) |

TABLE 5-continued

Examples of Heavy Chain Constant Regions

| Heavy Chain Constant | Amino Acid Sequence |
|---|---|
| IgG4 constant region variant 1 (also referred to herein as "IgG4v1") | ASTKGPSVFPLAPCSRSTSE STAALGCLVKDYFPEPVTVS WNSGALTSGVHTFPAVLQSS GLYSLSSVVTVPSSSLGTKT YTCNVDHKPSNTKVDKRVES KYGPPCPPCPAPEFEGGPSV FLFPPKPKDTLMISRTPEVT CVVVDVSQEDPEVQFNWYVD GVEVHNAKTKPREEQFNSTY RVVSVLTVLHQDWLNGKEYK CKVSNKGLPSSIEKTISKAK GQPREPQVYTLPPSQEEMTK NQVSLTCLVKGFYPSDIAVE WESNGQPENNYKTTPPVLDS DGSFFLYSRLTVDKSRWQEG NVFSCSVMHEALHNHYTQKS LSLSLGK (SEQ ID NO: 29) |
| IgG4 constant region variant 2 (also referred to herein as "IgG4v2") | ASTKGPSVFPLAPCSRSISE STAALGCLVKDYFPEPVTVS WNSGALISGVHTFPAVLQSS GLYSLSSVVTVPSSSLGTKT YTCNVDHKPSNTKVDKRVES KYGPPCPPCPAPEFEGGPSV FLFPPKPKDTLMISRTPEVT CVVVDVSQEDPEVQFNWYVD GVEVHNAKTKPREEQFNSTY RVVSVLTVLHQDWLNGKEYK CKVSNKGLPSSIEKTISKAK GQPREPQVYTLPPSQEEMTK NQVSLTCLVKGFYPSDIAVE WESNGQPENNYKTTPPVLDS DGSFFLYSRLTVDKSRWQEG NVFSCSVLHEALHSHYTQKS LSLSLGK (SEQ ID NO: 30) |

In some embodiments, the light chain of any of the humanized anti-factor Bb antibodies described herein may further comprise a light chain constant region ($C_L$). In some examples, the $C_L$ is a kappa light chain. In other examples, the $C_L$ is a lambda light chain. In some embodiments, the $C_L$ is a kappa light chain, the sequence of which is provided below:

(SEQ ID NO: 31)
RTVAAPSVFIFPPSDEQLKSGTASVVCLLNNFYPREAKVQWKVD

NALQSGNSQESVTEQDSKDSTYSLSSTLTLSKADYEKHKVYACE

VTHQGLSSPVTKSFNRGEC

Other antibody heavy and light chain constant regions are well known in the art, e.g., those provided in the IMMUNOGENETICS INFORMATION SYSTEM® (IMGT®) database or VBASE2 database, both of which are incorporated by reference herein.

In some embodiments, a humanized anti-factor Bb antibody described herein comprises a heavy chain comprising any one of the $V_H$ as listed in Table 2 or any variants thereof and a heavy chain constant region that is at least 80%, at least 85%, at least 90%, at least 95%, or at least 99% identical to any one of SEQ ID NOs: 28-30. In some embodiments, a humanized anti-factor Bb antibody described herein comprises a heavy chain comprising any one of the $V_H$ as listed in Table 2 or any variants thereof and a heavy chain constant region that contains no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with any one of SEQ ID NOs: 28-30. In some embodiments, a humanized anti-factor Bb antibody described herein comprises a heavy chain comprising any one of the $V_H$ as listed in Table 2 or any variants thereof and a heavy chain constant region comprising the amino acid sequence of any one of SEQ ID NOs: 28-30.

In some embodiments, a humanized anti-factor Bb antibody described herein comprises a light chain comprising any one of the $V_L$ as listed in Table 3 or any variants thereof and a light chain constant region that is at least 80%, at least 85%, at least 90%, at least 95%, or at least 99% identical to SEQ ID NO: 31. In some embodiments, a humanized anti-factor Bb antibody described herein comprises a light chain comprising any one of the $V_L$ as listed in Table 3 or any variants thereof and a light chain constant region that contains no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with SEQ ID NO: 31. In some embodiments, a humanized anti-factor Bb antibody described herein comprises a light chain comprising any one of the $V_L$ as listed in Table 3 or any variants thereof and a light chain constant region comprising the amino acid sequence of SEQ ID NO: 31.

Examples of the amino acid sequences of the heavy chain and light chain of the humanized anti-factor Bb antibodies described herein are provided in Table 6.

TABLE 6

Examples of the heavy chain and light chain of the humanized anti-factor Bb antibodies

| Antibody | Amino Acid Sequence |
|---|---|
| $V_H$6/Vκ7-IgG4wt | Heavy chain<br>EVQLVESGGGLVKPGGSLRLSCAASGFTFSNYAMSWVRQAPGKRLEWVATISNRGSYTYYPD SVKGRFTISRDNAKNSLYLQMNSLRAEDTALYYCARERPMDYWGQGTLVTVSSASTKGPSVFP LAPCSRSTSESTAALGCLVKDYFPEPVTVSWNSGALTSGVHTFPAVLQSSGLYSLSSVVT VPSSSLGTKTYTCNVDHKPSNTKVDKRVESKYGPPCPSCPAPEFLGGPSVFLFPPKPKDTL MISRTPEVTCVVVDVSQEDPEVQFNWYVDGVEVHNAKTKPREEQFNSTYRVVSVLTVL HQDWLNGKEYKCKVSNKGLPSSIEKTISKAKGQPREPQVYTLPPSQEEMTKNQVSLTCLV KGFYPSDIAVEWESNGQPENNYKTTPPVLDSDGSFFLYSRLTVDKSRWQEGNVFSCSVM HEALHNHYTQKSLSLSLGK (SEQ ID NO: 32)<br>Light Chain<br>DIQMTQSPSTLSASVGDRVTITCKASQDVGTAVAWYQQKPGKAPKLLIYWASTRHTGVPDRF SGSGSGTDFTLTISSLQAEDFAVYFCHQHSSNPLTFGQGTKLEIKRTVAAPSVFIFPPSDEQLK SGTASVVCLLNNFYPREAKVQWKVDNALQSGNSQESVTEQDSKDSTYSLSSTLTLSKAD YEKHKVYACEVTHQGLSSPVTKSFNRGEC (SEQ ID NO: 35) |

TABLE 6-continued

Examples of the heavy chain and light chain of the humanized anti-factor Bb antibodies

| Antibody | Amino Acid Sequence |
|---|---|
| V$_H$6/Vκ7-IgG4v1 | EVQLVESGGGLVKPGGSLRLSCAASGFTFSNYAMSWVRQAPGKRLEWVATISNRGSYTYYPD SVKGRFTISRDNAKNSLYLQMNSLRAEDTALYYCARERPMDYWGQGTLVTVSSASTKGPSVFP LAPCSRSTSESTAALGCLVKDYFPEPVTVSWNSGALTSGVHTFPAVLQSSGLYSLSSVVT VPSSSLGTKTYTCNVDHKPSNTKVDKRVESKYGPPCPPCPAPEFEGGPSVFLFPPKPKDTL MISRTPEVTCVVVDVSQEDPEVQFNWYVDGVEVHNAKTKPREEQFNSTYRVVSVLTVL HQDWLNGKEYKCKVSNKGLPSSIEKTISKAKGQPREPQVYTLPPSQEEMTKNQVSLTCLV KGFYPSDIAVEWESNGQPENNYKTTPPVLDSDGSFFLYSRLTVDKSRWQEGNVFSCSVM HEALHNHYTQKSLSLSLGK (SEQ ID NO: 33)<br>Light Chain<br>DIQMTQSPSTLSASVGDRVTITCKASQDVGTAVAWYQQKPGKAPKLLIYWASTRHTGVPDRF SGSGSGTDFTLTISSLQAEDFAVYFCHQHSSNPLTFGQGTKLEIKRTVAAPSVFIFPPSDEQLK SGTASVVCLLNNFYPREAKVQWKVDNALQSGNSQESVTEQDSKDSTYSLSSTLTLSKAD YEKHKVYACEVTHQGLSSPVTKSFNRGEC (SEQ ID NO: 35) |
| V$_H$6/Vκ7-IgG4v2 | EVQLVESGGGLVKPGGSLRLSCAASGFTFSNYAMSWVRQAPGKRLEWVATISNRGSYTYYPD SVKGRFTISRDNAKNSLYLQMNSLRAEDTALYYCARERPMDYWGQGTLVTVSSASTKGPSVFP LAPCSRSTSESTAALGCLVKDYFPEPVTVSWNSGALTSGVHTFPAVLQSSGLYSLSSVVT VPSSSLGTKTYTCNVDHKPSNTKVDKRVESKYGPPCPPCPAPEFEGGPSVFLFPPKPKDTL MISRTPEVTCVVVDVSQEDPEVQFNWYVDGVEVHNAKTKPREEQFNSTYRVVSVLTVL HQDWLNGKEYKCKVSNKGLPSSIEKTISKAKGQPREPQVYTLPPSQEEMTKNQVSLTCLV KGFYPSDIAVEWESNGQPENNYKTTPPVLDSDGSFFLYSRLTVDKSRWQEGNVFSCSVLH EALHSHYTQKSLSLSLGK (SEQ ID NO: 34)<br>Light Chain<br>DIQMTQSPSTLSASVGDRVTITCKASQDVGTAVAWYQQKPGKAPKLLIYWASTRHTGVPDRF SGSGSGTDFTLTISSLQAEDFAVYFCHQHSSNPLTFGQGTKLEIKRTVAAPSVFIFPPSDEQLK SGTASVVCLLNNFYPREAKVQWKVDNALQSGNSQESVTEQDSKDSTYSLSSTLTLSKAD YEKHKVYACEVTHQGLSSPVTKSFNRGEC (SEQ ID NO: 35) |
| V$_H$4/Vκ6-IgG4wt | Heavy Chain<br>EVQLVESGGGLVKPGGSLRLSCAASGFTFSNYAMSWVRQAPGKRLEWVATISNRGSYTYYPD SVKGRFTISRDNAKNSLYLQMSSLRSEDTALYYCARERPMDYWGQGTSVTVSSASTKGPSVFP LAPCSRSTSESTAALGCLVKDYFPEPVTVSWNSGALTSGVHTFPAVLQSSGLYSLSSVVT VPSSSLGTKTYTCNVDHKPSNTKVDKRVESKYGPPCPSCPAPEFLGGPSVFLFPPKPKDTL MISRTPEVTCVVVDVSQEDPEVQFNWYVDGVEVHNAKTKPREEQFNSTYRVVSVLTVL HQDWLNGKEYKCKVSNKGLPSSIEKTISKAKGQPREPQVYTLPPSQEEMTKNQVSLTCLV KGFYPSDIAVEWESNGQPENNYKTTPPVLDSDGSFFLYSRLTVDKSRWQEGNVFSCSVM HEALHNHYTQKSLSLSLGK (SEQ ID NO: 36)<br>Light Chain<br>DIVMTQSPSFLSASVGDRVTITCKASQDVGTAVAWYQQKPGKAPKLLIYWASTRHTGVPDRF TGSGSGTDFTLTISSLQSEDFAVYFCHQHSSNPLTFGQGTKLEIKRTVAAPSVFIFPPSDEQLK SGTASVVCLLNNFYPREAKVQWKVDNALQSGNSQESVTEQDSKDSTYSLSSTLTLSKAD YEKHKVYACEVTHQGLSSPVTKSFNRGEC (SEQ ID NO: 39) |
| V$_H$4/Vκ6-IgG4v1 | Heavy Chain<br>EVQLVESGGGLVKPGGSLRLSCAASGFTFSNYAMSWVRQAPGKRLEWVATISNRGSYTYYPD SVKGRFTISRDNAKNSLYLQMSSLRSEDTALYYCARERPMDYWGQGTSVTVSSASTKGPSVFP LAPCSRSTSESTAALGCLVKDYFPEPVTVSWNSGALTSGVHTFPAVLQSSGLYSLSSVVT VPSSSLGTKTYTCNVDHKPSNTKVDKRVESKYGPPCPPCPAPEFEGGPSVFLFPPKPKDTL MISRTPEVTCVVVDVSQEDPEVQFNWYVDGVEVHNAKTKPREEQFNSTYRVVSVLTVL HQDWLNGKEYKCKVSNKGLPSSIEKTISKAKGQPREPQVYTLPPSQEEMTKNQVSLTCLV KGFYPSDIAVEWESNGQPENNYKTTPPVLDSDGSFFLYSRLTVDKSRWQEGNVFSCSVM HEALHNHYTQKSLSLGK (SEQ ID NO: 37)<br>Light Chain<br>DIVMTQSPSFLSASVGDRVTITCKASQDVGTAVAWYQQKPGKAPKLLIYWASTRHTGVPDRF TGSGSGTDFTLTISSLQSEDFAVYFCHQHSSNPLTFGQGTKLEIKRTVAAPSVFIFPPSDEQLK SGTASVVCLLNNFYPREAKVQWKVDNALQSGNSQESVTEQDSKDSTYSLSSTLTLSKAD YEKHKVYACEVTHQGLSSPVTKSFNRGEC (SEQ ID NO: 39) |

TABLE 6-continued

Examples of the heavy chain and light chain of the humanized anti-factor Bb antibodies

| Antibody | Amino Acid Sequence |
|---|---|
| V$_H$4/Vκ6-IgG4v2 | Heavy Chain<br>EVQLVESGGGLVKPGGSLRLSCAASGFTFSNYAMSWVRQAPGKRLEWVATISNRGSYTYYPD<br>SVKGRFTISRDNAKNSLYLQMSSLRSEDTALYYCARERPMDYWGQGTSVTVSSASTKGPSVFP<br>LAPCSRSTSESTAALGCLVKDYFPEPVTVSWNSGALTSGVHTFPAVLQSSGLYSLSSVVT<br>VPSSSLGTKTYTCNVDHKPSNTKVDKRVESKYGPPCPPCPAPEFEGGPSVFLFPPKPKDTL<br>MISRTPEVTCVVVDVSQEDPEVQFNWYVDGVEVHNAKTKPREEQFNSTYRVVSVLTVL<br>HQDWLNGKEYKCKVSNKGLPSSIEKTISKAKGQPREPQVYTLPPSQEEMTKNQVSLTCLV<br>KGFYPSDIAVEWESNGQPENNYKTTPPVLDSDGSFFLYSRLTVDKSRWQEGNVFSCSVLH<br>EALHSHYTQKSLSLSLGK (SEQ ID NO: 38)<br>Light Chain<br>DIVMTQSPSFLSASVGDRVTITCKASQDVGTAVAWYQQKPGKAPKLLIYWASTRHTGVPDRF<br>TGSGSGTDFTLTISSLQSEDFAVYFCHQHSSNPLTFGQGTKLEIKRTVAAPSVFIFPPSDEQLK<br>SGTASVVCLLNNFYPREAKVQWKVDNALQSGNSQESVTEQDSKDSTYSLSSTLTLSKAD<br>YEKHKVYACEVTHQGLSSPVTKSFNRGEC (SEQ ID NO: 39) |

In Table 6:
bolded: CDRs accordingly to Kabat definition
Italic: V$_H$/V$_L$

In some embodiments, a humanized anti-factor Bb antibody comprises a heavy chain comprising the amino acid sequences of SEQ ID NO: 32 and a light chain comprising the amino acid sequence of SEQ ID NO: 35.

In some embodiments, a humanized anti-factor Bb antibody comprises a heavy chain comprising the amino acid sequences of SEQ ID NO: 33 and a light chain comprising the amino acid sequence of SEQ ID NO: 35.

In some embodiments, a humanized anti-factor Bb antibody comprises a heavy chain comprising the amino acid sequences of SEQ ID NO: 34 and a light chain comprising the amino acid sequence of SEQ ID NO: 35.

In some embodiments, a humanized anti-factor Bb antibody comprises a heavy chain comprising the amino acid sequences of SEQ ID NO: 36 and a light chain comprising the amino acid sequence of SEQ ID NO: 39.

In some embodiments, a humanized anti-factor Bb antibody comprises a heavy chain comprising the amino acid sequences of SEQ ID NO: 37 and a light chain comprising the amino acid sequence of SEQ ID NO: 39.

In some embodiments, a humanized anti-factor Bb antibody comprises a heavy chain comprising the amino acid sequences of SEQ ID NO: 38 and a light chain comprising the amino acid sequence of SEQ ID NO: 39.

In some embodiments, a humanized anti-factor Bb antibody of the present disclosure binds a factor Bb protein (e.g., a factor Bb protein from a mammal, fish, or invertebrate that has a complement system). In some embodiments, a humanized anti-factor Bb antibody of the present disclosure binds a mammalian factor Bb protein. In some embodiments, a humanized anti-factor Bb antibody of the present disclosure binds a human factor Bb protein. In some embodiments, a humanized anti-factor Bb antibody of the present disclosure binds a factor Bb protein having the amino acid sequence of SEQ ID NO: 40.

```
Homo sapiens factor Bb protein
                              (SEQ ID NO: 40)
KIVLDPSGSMNIYLVLDGSDSIGASNFTGAKKCLVN

LIEKVASYGVKPRYGLVTYATYPKIWVKVSEADSS

NADWVTKQLNEINYEDHKLKSGTNTKKALQAVYSM

MSWPDDVPPEGWNRTRHVIILMTDGLHNMGGDPIT
```

-continued
```
VIDEIRDLLYIGKDRKNPREDYLDVYVFGVGPLVN

QVNINALASKKDNEQHVFKVKDMENLEDVFYQMID

ESQSLSLCGMVWEHRKGTDYHKQPWQAKISVIRPS

KGHESCMGAVVSEYFVLTAAHCFTVDDKEHSIKVS

VGGEKRDLEIEVVLFHPNYNINGKKEAGIPEFYDY

DVALIKLKNKLKYGQTIRPICLPCTEGTTRALRLP

PTTTCQQQKEELLPAQDIKALFVSEEEKKLTRKEV

YIKNGDKKGSCERDAQYAPGYDKVKDISEVVTPRF

LCTGGVSPYADPNTCRGDSGGPLIVHKRSRFIQVG

VISWGVVDVCKNQKRQKQVPAHARDFHINLFQVLP

WLKEKLQDEDLGFL
```

In some embodiments, a humanized anti-factor Bb antibody of the present disclosure binds a complement Bb protein with an affinity of about $10^{-6}$ to $10^{-11}$ nM, e.g., from about $10^{-6}$ M to about $10^{-7}$ M, about $10^{-7}$ M to about $10^{-8}$ M, about $10^{-8}$ M to about $10^{-9}$ M, from about $10^{-9}$ M to about $10^{-10}$ M, or from about $10^{-10}$ M to about $10^{-11}$ M. The terms "about" preceding a numerical value mean±10% of the recited numerical value.

In some embodiments, a humanized anti-factor Bb antibody of the present disclosure exhibits preferential binding for factor Bb, compared with binding for factor B. In some embodiments, a humanized anti-factor Bb antibody of the present disclosure binds to factor Bb, but does not substantially bind to soluble Factor B. In some embodiments, a humanized anti-factor Bb antibody of the present disclosure binds to factor Bb with an affinity that is at least 2-fold, at least 2.5-fold, at least 3-fold, at least 4-fold, at least 5-fold, at least 7.5-fold, at least 10-fold, at least 15-fold, at least 20-fold, at least 25-fold, at least 50-fold, at least 75-fold, or at least 100-fold, higher than the affinity of the antibody for factor B. In some embodiments, a humanized anti-factor Bb antibody of the present disclosure binds to factor Bb with an affinity that is 2-fold to 2.5-fold, 2.5-fold to 5-fold, 5-fold to 10-fold, 10-fold to 15-fold, 15-fold to 20-fold, 20-fold to 25-fold, 25-fold to 50-fold, 50-fold to 75-fold, or 75-fold to 100-fold, higher than the affinity of the antibody for factor B.

In some embodiments, a humanized anti-factor Bb antibody of the present disclosure inhibits the complement pathway activity by at least 10%, at least 20%, at least 30%, at least 40%, at least 50%, at least 60%, at least 65%, at least 70%, at least 75%, at least 80%, at least 85%, at least 90%, at least 95%, or 100%, compared to the level of complement activity in the absence of a humanized anti-factor Bb antibody.

In some embodiments, a humanized anti-factor Bb antibody of the present disclosure inhibits alternative pathway (AP) activity by at least 10%, at least 20%, at least 30%, at least 40%, at least 50%, at least 60%, at least 65%, at least 70%, at least 75%, at least 80%, at least 85%, at least 90%, at least 95%, or 100%, compared to the level of AP activity in the absence of a humanized anti-factor Bb antibody. In some embodiments, a humanized anti-factor Bb antibody of the present disclosure inhibits AP activity with an $IC_{50}$ of $10^{-7}$ M to $10^{-9}$ M, e.g., an $IC_{50}$ of $10^{-7}$ M to $5 \times 10^{-7}$ M, $5 \times 10^{-7}$ M to $10^{-8}$ M, $10^{-8}$ M to $5 \times 10^{-8}$ M, or $5 \times 10^{-8}$ M to $10^{-9}$ M. In some embodiments, the complement AP activity is selected the group consisting of AP-mediated terminal membrane attack complex (MAC) deposition, AP-mediated hemolysis, C3 fragment deposition on red blood cells or other cell types, C3b/Bb-mediated cleavage of C3, and C3bBb3b-mediated cleavage of C5. In some embodiments, inhibition of complement AP activity by the humanized anti-factor Bb antibodies can be measured using the Complement System Alternative Pathway WIESLAB® kit.

In some embodiments, a humanized anti-factor Bb antibody of the present disclosure inhibits formation of membrane attack complex (MAC) by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of MAC formed in the absence of the anti-factor Bb antibody.

In some embodiments, a humanized anti-factor Bb antibody of the present disclosure inhibits C3b/Bb-mediated cleavage of C3. C3b/Bb is also known as "C3 convertase." In some embodiments, a humanized anti-factor Bb antibody of the present disclosure inhibits C3b/Bb-mediated cleavage of C3 by at least 10%, at least 20%, at least 30%, at least 40%, at least 50%, at least 60%, at least 65%, at least 70%, at least 75%, at least 80%, at least 85%, at least 90%, at least 95%, or 100%, compared to the cleavage of C3 in the absence of the anti-factor Bb antibody. In some embodiments, a humanized anti-factor Bb antibody of the present disclosure inhibits C3b/Bb-mediated cleavage of C3 with an $IC_{50}$ of from $10^{-7}$ M to $10^{-9}$ M, e.g., an $IC_{50}$ of from $10^{-7}$ M to $5 \times 10^{-7}$ M, from $5 \times 10^{-7}$ M to $10^{-8}$ M, from $10^{-8}$ M to $5 \times 10^{-8}$ M, or from $5 \times 10^{-8}$ M to $10^{-9}$ M.

In some embodiments, a humanized anti-factor Bb antibody of the present disclosure inhibits C3b/Bb-mediated cleavage of C3, thereby reducing production of a C3 cleavage product. For example, a humanized anti-factor Bb antibody of the present disclosure may inhibit C3b/Bb-mediated cleavage of C3, thereby reducing production of a C3 cleavage product (e.g., C3a and/or C3b) by at least 10%, at least 20%, at least 30%, at least 40%, at least 50%, at least 60%, at least 65%, at least 70%, at least 75%, at least 80%, at least 85%, at least 90%, at least 95%, or 100%, compared to the production of the C3 cleavage product in the absence of the anti-factor Bb antibody.

In some embodiments, a humanized anti-factor Bb antibody of the present disclosure inhibits complement AP-mediated cell lysis by at least 10%, at least 20%, at least 30%, at least 40%, at least 50%, at least 60%, at least 65%, at least 70%, at least 75%, at least 80%, at least 85%, at least 90%, at least 95%, or 100%, compared to the degree of cell lysis in the absence of the anti-factor Bb antibody. A cell lysis assay can be used to determine the degree of inhibition of AP-mediated cell lysis. In some embodiments, a humanized anti-factor Bb antibody of the present disclosure inhibits its AP-mediated cell lysis with an $IC_{50}$ of from $10^{-7}$ M to $10^{-9}$ M, e.g., an $IC_{50}$ of from $10^{-7}$ M to $5 \times 10^{-7}$ M, from $5 \times 10^{-7}$ M to $10^{-8}$ M, from $10^{-8}$ M to $5 \times 10^{-8}$ M, or from $5 \times 10^{-8}$ M to $10^{-9}$ M.

In some embodiments, a humanized anti-factor Bb antibody of the present disclosure inhibits complement AP-mediated hemolysis by at least 10%, at least 20%, at least 30%, at least 40%, at least 50%, at least 60%, at least 65%, at least 70%, at least 75%, at least 80%, at least 85%, at least 90%, at least 95%, or 100%, compared to the degree of hemolysis in the absence of the anti-factor Bb antibody. A rabbit red blood cell (RBC) hemolysis assay can be used to determine the degree of inhibition of AP-mediated hemolysis. In some embodiments, a humanized anti-factor Bb antibody of the present disclosure inhibits AP-mediated hemolysis with an $IC_{50}$ of from $10^{-7}$ M to $10^{-9}$ M, e.g., an $IC_{50}$ of from $10^{-7}$ M to $5 \times 10^{-7}$ M, from $5 \times 10^{-7}$ M to $10^{-8}$ M, from $10^{-8}$ M to $5 \times 10^{-8}$ M, or from $5 \times 10^{-8}$ M to $10^{-9}$ M.

In some embodiments, a humanized anti-factor Bb antibody of the present disclosure inhibits AP-mediated deposition of C3b, C3d, or other C3 split product on a cell or tissue. For example, a humanized anti-factor Bb antibody of the present disclosure may inhibit AP-mediated deposition of C3b, C3d, or other C3 split product on a cell or tissue by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of deposition of C3b, C3d, or other C3 split product on the cell or tissue in the absence of administration of the anti-factor Bb antibody, or before administration of the anti-factor Bb antibody. In some embodiments, a humanized anti-factor Bb antibody of the present disclosure inhibits AP-mediated deposition of C3b, C3d, or other C3 split product on a cell or tissue with an $IC_{50}$ of from $10^{-7}$ M to $10^{-9}$ M, e.g., an $IC_{50}$ of from $10^{-7}$ M to $5 \times 10^{-7}$ M, from $5 \times 10^{-7}$ M to $10^{-8}$ M, from $10^{-8}$ M to $5 \times 10^{-8}$ M, or from $5 \times 10^{-8}$ M to $10^{-9}$ M.

In some embodiments, a humanized anti-factor Bb antibody of the present disclosure inhibits AP-mediated C3b deposition on a cell or tissue by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of C3b deposition on the cell or tissue in the absence of the humanized anti-factor Bb antibody. In some embodiments, a humanized anti-factor Bb antibody of the present disclosure inhibits AP-mediated C3b deposition on a cell or tissue with an $IC_{50}$ of from $10^{-7}$ M to $10^{-9}$ M, e.g., an $IC_{50}$ of from $10^{-7}$ M to $5 \times 10^{-7}$ M, from $5 \times 10^{-7}$ M to $10^{-8}$ M, from $10^{-8}$ M to $5 \times 10^{-8}$ M, or from $5 \times 10^{-8}$ M to $10^{-9}$ M.

In some embodiments, a humanized anti-factor Bb antibody of the present disclosure inhibits AP-mediated C3b deposition on red blood cells (RBCs) or other cell types by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of C3b deposition on RBCs in the absence of the humanized anti-factor Bb antibody. In some embodiments, a humanized anti-factor Bb antibody of the present disclosure inhibits AP-mediated C3b deposition on RBCs with an $IC_{50}$ of from $10^{-7}$ M to $10^{-9}$ M, e.g., an $IC_{50}$ of from $10^{-7}$ M to $5\times10^{-7}$ M, from $5\times10^{-7}$ M to $10^{-8}$ M, from $10^{-8}$ M to $5\times10^{-8}$ M, or from $5\times10^{-8}$ M to $10^{-9}$ M.

In some embodiments, a humanized anti-factor Bb antibody of the present disclosure, when administered to a subject in need thereof, reduces the amount of factor Bb in circulation in the subject. For example, a humanized anti-factor Bb antibody of the present disclosure, when administered to a subject in need thereof, may reduce the amount of factor Bb in circulation in the subject by at least 10%, at least 20%, at least 30%, at least 40%, at least 50%, at least 60%, at least 65%, at least 70%, at least 75%, at least 80%, at least 85%, at least 90%, or at least 95%, compared to the amount of factor Bb in circulation in the subject in the absence of administering the humanized anti-factor Bb antibody, or compared to the amount of factor Bb in circulation in the subject before administration of the humanized anti-factor Bb antibody.

In some embodiments, a humanized anti-factor Bb antibody of the present disclosure inhibits C3bBb3b-mediated cleavage of C5. In some embodiments, a humanized anti-factor Bb antibody of the present disclosure inhibits C3bBb3b-mediated cleavage of C5 by at least 10%, at least 20%, at least 30%, at least 40%, at least 50%, at least 60%, at least 65%, at least 70%, at least 75%, at least 80%, at least 85%, at least 90%, or at least 95%, compared to C3bBb3b-mediated cleavage of C5 in the absence of a humanized anti-factor Bb antibody.

In some embodiments, a humanized anti-factor Bb antibody of the present disclosure is a bispecific or multispecific antibody. For example, a humanized anti-factor Bb antibody can be a bispecific antibody comprising a first antigen-binding portion that specifically binds an epitope in a complement Bb protein, and a second antigen-binding portion that binds a second antigen.

Immunoconjugates

In some embodiments, a humanized anti-factor Bb antibody of the present disclosure is conjugated with another agent to form an immunoconjugate. For example, a humanized anti-factor Bb antibody may comprise a free thiol (—SH) group at the carboxyl terminus, where the free thiol group can be used to attach the antibody to a second polypeptide (e.g., another antibody, including a humanized anti-factor Bb antibody), a scaffold, a carrier, etc. In some embodiments, a humanized anti-factor Bb antibody comprises at least one non-naturally occurring amino acids. In some embodiments, the non-naturally encoded amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for suitable non-naturally occurring amino acids. Inclusion of a non-naturally occurring amino acid can provide for linkage to a polymer, a second polypeptide, a scaffold, etc. For example, a humanized anti-factor Bb antibody linked to a water-soluble polymer can be made by reacting a water-soluble polymer (e.g., PEG) that comprises a carbonyl group to the antibody, where the antibody comprises a non-naturally encoded amino acid that comprises an aminooxy, hydrazine, hydrazide or semicarbazide group. In some embodiments, a humanized anti-factor Bb antibody linked to a water-soluble polymer can be made by reacting the antibody that comprises an alkyne-containing amino acid with a water-soluble polymer (e.g., PEG) that comprises an azide moiety. In some embodiments, the azide or alkyne group is linked to the PEG molecule through an amide linkage.

In some embodiments, a humanized anti-factor Bb antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers can have an average molecular weight in a range of from 500 Da to 50,000 Da, e.g., from 5,000 Da to 40,000 Da, or from 25,000 to 40,000 Da.

In some embodiments, a humanized anti-factor Bb antibody comprises a "radiopaque" label, e.g., a label that can be easily visualized using for example x-rays. Radiopaque materials are well known to those of skill in the art. The most common radiopaque materials include iodide, bromide or barium salts. Other radiopaque materials are also known and include but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), and/or radiopaque barium multimer complexes (see, e.g., U.S. Pat. No. 4,866,132).

In some embodiments, a humanized anti-factor Bb antibody is covalently linked to a second moiety (e.g., a lipid, a polypeptide other than a humanized anti-factor Bb antibody, a synthetic polymer, and/or a carbohydrate) using for example, glutaraldehyde, a homobifunctional cross-linker, or a heterobifunctional cross-linker.

In some embodiments, a humanized anti-factor Bb antibody is immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a humanized anti-factor Bb antibody onto a solid support are well known and include, but are not limited to ionic, hydrophobic, and/or covalent interactions. Solid supports can be soluble or insoluble, e.g., in aqueous solution. In some embodiments, a suitable solid support is generally insoluble in an aqueous solution.

In some embodiments, a humanized anti-factor Bb antibody comprises a detectable label. Suitable detectable labels include any composition detectable by spectroscopic, photochemical, biochemical, immunochemical, electrical, optical or chemical means. Suitable include, but are not limited to, magnetic beads (e.g. DYNABEADS™), fluorescent dyes (e.g., fluorescein isothiocyanate, Texas Red, rhodamine, a green fluorescent protein, a red fluorescent protein, , and/or a yellow fluorescent protein), radiolabels (e.g., $^3$H $^{125}$I, $^{35}$s $^{14}$C, or $^{32}$P), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a humanized anti-factor Bb antibody comprises a contrast agent or a radioisotope, where the contrast agent or radioisotope is one that is suitable for use in imaging, e.g., imaging procedures carried out on humans. Non-limiting examples of labels include radioisotope such as $^{123}$I (iodine), $^{18}$F (fluorine), $^{99}$Tc (technetium), $^{111}$in (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. A humanized anti-factor Bb antibody can be labeled using standard techniques. For example, a humanized anti-factor Bb antibody can be iodinated using chloramine T or 1,3,4,6-tetrachloro-3α,6α-diphenylglycouril. For fluorination, fluorine is added to a humanized anti-factor Bb antibody during the synthesis by a fluoride ion displacement reaction. See, Muller-Gartner, H., TIB Tech., 16:122-130 (1998) and Saji, H., *Crit. Rev. Ther. Drug Carrier Syst.*, 16(2):209-244 (1999) for a review of synthesis of proteins with such radioisotopes. A humanized anti-factor Bb antibody can also be labeled with a contrast agent through standard techniques. For example, a humanized anti-factor Bb antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., *Chem. Rev.* 99:2293-2352 (1999) and Lauffer et al., *J. Magn. Reson. Imaging,* 3:11-16 (1985). A humanized anti-factor Bb antibody can be labeled with Gd by, for example, conjugating polylysine-Gd chelates to the antibody. See, for example, Curtet et al., *Invest. Radiol.*, 33(10):752-761 (1998). Alternatively, in some embodiments, a humanized anti-factor Bb antibody can be labeled with Gd by incubating paramagnetic polymerized liposomes that include Gd chelator lipid with avidin and biotinylated antibody. See, for example, Sipkins et al., *Nature Med.,* 4:623-626 (1998).

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, and/or mPlum (Shaner et al. (2005) *Nat. Methods* 2:905-909). Any of a variety of fluorescent and colored proteins from Anthozoan species, as described in, e.g., Matz et al. (1999) *Nature Biotechnol.* 17:969-973, is suitable for use.

In some embodiments, a humanized anti-factor Bb antibody is conjugated to a therapeutic agent. Any of the humanized anti-factor Bb antibodies disclosed herein can be used to form an antibody-agent conjugate. The agent can be attached to the N terminus of the light chain, the C terminus of the light chain, the N terminus of the heavy chain, or the C terminus of the heavy chain. In some embodiments, the agent is attached to the hinge of the antibody or to at least one other sites on the antibody. For a single chain antibody, the agent can be attached to the N or C terminus of the single chain antibody. The agent can be conjugated to the antibody directly or via a linker using techniques known to those skilled in the art. The linker can be cleavable or non-cleavable. Examples of such therapeutic agents (e.g., for use in therapy) are known to those skilled in the art.

In some embodiments, a humanized anti-factor Bb antibody is linked to (e.g., covalently or non-covalently linked) a fusion partner, e.g., a ligand; an epitope tag; a peptide; and/or a protein other than an antibody. Suitable fusion partners include peptides and polypeptides that confer enhanced stability in vivo (e.g., enhanced serum half-life); provide ease of purification, e.g., (His)n, e.g., 6His; provide for secretion of the fusion protein from a cell; provide an epitope tag, e.g., GST, hemagglutinin (HA; e.g., YPYDVPDYA; SEQ ID NO: 55), FLAG (e.g., DYKDDDDK; SEQ ID NO: 56), and/or c-myc (e.g., EQKLISEEDL; SEQ ID NO: 57); provide a detectable signal, e.g., an enzyme that generates a detectable product (e.g., (3-galactosidase, luciferase), or a protein that is itself detectable, e.g., a green fluorescent protein, a red fluorescent protein, a yellow fluorescent protein, etc.; and/or provides for multimerization, e.g., a multimerization domain such as an Fc portion of an immunoglobulin. The fusion can also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Exemplary affinity domains include His5 (HHHHH) (SEQ ID NO: 58), HisX6 (HHHHHH) (SEQ ID NO:59), C-myc (EQKLISEEDL) (SEQ ID NO:60), Flag (DYKDDDDK) (SEQ ID NO:61), StrepTag (WSHPQFEK) (SEQ ID NO:62), hemagglutinin, e.g., HA Tag (YPYDVPDYA; SEQ ID NO:63), glutathione-S-transferase (GST), thioredoxin, cellulose binding domain, RYIRS (SEQ ID NO:66), Phe-His-His-Thr (SEQ ID NO:64), chitin binding domain, S-peptide, T7 peptide, SH2 domain, C-end RNA tag, WEAAAREACCRECCARA (SEQ ID NO:65), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

Methods of Producing Humanized Anti-Factor Bb Antibodies

In some embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are XENOMOUSE® from AMGEN® (Amgen, Inc. (Fremont, CA)) and HUMAB-MOUSE® and TC MOUSE™ from MEDAREX® (Medarex, Inc. (Princeton, NJ)) or H2L2 mice from Harbour Antibodies BV (Holland). In another alternative, antibodies may be made recombinantly by phage display or yeast technology. See, for example, U.S. Pat. Nos. 5,565,332; 5,580,717; 5,733,743; and 6,265,150; and Winter et al., (1994) *Annu. Rev. Immunol.* 12:433-455. Alternatively, the phage display technology (McCafferty et al., (1990) *Nature* 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments. Genetically engineered antibodies, such as humanized antibodies, chimeric antibodies, single-chain antibodies, and bispecific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into at least one expression vector, which is then transfected into host cells such as *Escherichia coli* (*E. coli*) cells, simian COS cells, Chinese hamster ovary (CHO) cells, human HEK293 cells, or myeloma cells that do not otherwise produce immunoglobulin protein, to obtain the synthesis of monoclonal antibodies in recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) *Proc. Nat. Acad. Sci.* 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

A single-chain antibody can be prepared via recombinant technology, for example, by linking a nucleotide sequence coding for a heavy chain variable region and a nucleotide sequence coding for a light chain variable region. In some embodiments, a flexible linker is incorporated between the two variable regions.

Alternatively, techniques described for the production of single chain antibodies (U.S. Pat. Nos. 4,946,778 and 4,704, 692) can be adapted, for example, to produce a phage or yeast scFv library and scFv clones specific to factor Bb can be identified from the library following routine procedures. Positive clones can be subjected to further screening to identify those that has high factor Bb binding affinity.

In some embodiments, a humanized anti-factor Bb antibody is prepared by recombinant technology as exemplified below. Nucleic acids encoding the heavy and light chain of an anti-factor Bb antibody as described herein can be cloned into one expression vector, each nucleotide sequence being in operable linkage to a suitable promoter. In one example, each of the nucleotide sequences encoding the heavy chain and light chain is in operable linkage to a distinct promoter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoters would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV promoter, and the herpes simplex tk virus promoter.

Regulatable promoters can also be used. Such regulatable promoters include those using the lac repressor from *E. coli* as a transcription modulator to regulate transcription from lac operator bearing mammalian cell promoters [Brown, M. et al., *Cell,* 49:603-612 (1987)], those using the tetracycline repressor (tetR) [Gossen, M., and Bujard, H., *Proc. Natl. Acad. Sci. USA* 89:5547-555115 (1992); Yao, F. et al., *Human Gene Therapy,* 9:1939-1950 (1998); Shockelt, P., et al., *Proc. Natl. Acad. Sci. USA,* 92:6522-6526 (1995)]. Other systems include FK506 dimer, VP16 or p65 using astradiol, RU486, diphenol murislerone, or rapamycin. Inducible systems are available from INVITROGEN®, CLONTECH® and ARIAD®, among others.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., *Cell,* 49:603-612 (1987)]; Gossen and Bujard (1992); [M. Gossen et al., *Natl. Acad. Sci. USA,* 89:5547-5551(1992)] combined the tetracycline repressor (tetR) with the transcription activator (VP 16) to create a tetR-mammalian cell transcription activator fusion protein, tTa (tetR-VP16), with the tetO bearing minimal promoter derived from the human cytomegalovirus (hCMV) promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells transactivator or repressor fusion protein, which in some instances can be toxic to cells (Gossen 5 et al., *Natl. Acad. Sci. USA,* 89:5547-5551 (1992); Shockett et al., *Proc. Natl. Acad. Sci. USA,* 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art. Examples of polyadenylation signals useful to practice the methods described herein include, but are not limited to, human collagen I polyadenylation signal, human collagen II polyadenylation signal, and SV40 polyadenylation signal.

At least one vector (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-factor Bb antibody, as also described herein. The recombinant expression vector can be introduced into a suitable host cell (e.g., a dihydrofolate reductase (DHFR)-CHO cell) by a conventional method, e.g., calcium phosphate mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In some embodiments, two recombinant expression vectors are provided, one encoding the heavy chain of the anti-factor Bb antibody and the other encoding the light chain of the anti-factor Bb antibody. Both of the two recombinant expression vectors can be introduced into a suitable host cell (e.g., DHFR-CHO cell) by a conventional method, e.g., calcium phosphate-mediated transfection.

Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-factor Bb antibody as described herein (e.g., as provided in Tables 2 and 3), vectors (e.g., expression vectors) containing such; and host cells comprising the vectors are within the scope of the present disclosure.

Pharmaceutical Compositions and Therapeutic Methods

Other aspects of the present disclosure provide compositions, including pharmaceutical compositions comprising any one of the humanized anti-factor Bb antibodies described herein. In general, a pharmaceutical composition, also referred to herein as a formulation, comprises an effective amount of any one of the humanized anti-factor Bb antibodies described herein. An "effective amount" means a dosage sufficient to produce a desired result, e.g., reduction in an adverse symptom associated with a complement-mediated disease or disorder, amelioration of a symptom of a complement-mediated disease or disorder, slowing progression of a complement-mediated disease or disorder, etc. Generally, the desired result is at least a reduction in a symptom of a complement-mediated disease or disorder, as compared to a control.

In a method of the present disclosure, a humanized anti-factor Bb antibody can be administered to a subject using a convenient means capable of resulting in the desired therapeutic effect or diagnostic effect. Thus, a humanized anti-factor Bb antibody can be incorporated into a variety of formulations for therapeutic administration. More particularly, a humanized anti-factor Bb antibody can be formulated into pharmaceutical compositions by combination with appropriate, pharmaceutically acceptable carriers, pharmaceutically acceptable diluents, or other pharmaceutically acceptable excipients. In some embodiments, a pharmaceutical composition comprises a humanized anti-factor Bb antibody and a pharmaceutically acceptable excipient.

In pharmaceutical dosage forms, a humanized anti-factor Bb antibody can be administered in the form of their pharmaceutically acceptable salts, or they can also be used alone or in appropriate association, as well as in combination, with other pharmaceutically active compounds. The following methods and excipients are merely exemplary and are in no way limiting.

For oral preparations, a humanized anti-factor Bb antibody can be used alone or in combination with appropriate additives to make tablets, powders, granules or capsules.

A humanized anti-factor Bb antibody can be formulated into preparations for injection by dissolving, suspending or emulsifying the antibody in an aqueous or nonaqueous solvent; and if desired, with conventional additives such as solubilizers, isotonic agents, suspending agents, emulsifying agents, stabilizers and preservatives.

Pharmaceutical compositions comprising a humanized anti-factor Bb antibody are prepared by mixing a humanized anti-factor Bb antibody having the desired degree of purity with optional physiologically acceptable carriers, other excipients, stabilizers, surfactants, buffers and/or tonicity agents. Acceptable carriers, other excipients and/or stabilizers are nontoxic to recipients at the dosages and concentrations employed. In some embodiments, the compositions comprise a buffer, an antioxidant, an amino acid or a combination thereof.

The pharmaceutical composition can be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however, solutions comprising antibacterial agents can be used for the production of pharmaceutical compositions for parenteral administration; see also Chen (1992) *Drug Dev Ind Pharm* 18, 1311-54.

A tonicity agent can be included in the antibody formulation to modulate the tonicity of the formulation. In some embodiments, the aqueous formulation is isotonic, although hypertonic or hypotonic solutions can be suitable. The term "isotonic" denotes a solution having the same tonicity as some other solution with which it is compared, such as a physiological salt solution or serum.

A surfactant can also be added to the antibody formulation to reduce aggregation of the formulated antibody and/or minimize the formation of particulates in the formulation and/or reduce adsorption.

A lyoprotectant can also be added in order to protect the labile active ingredient (e.g., a protein) against destabilizing conditions during the lyophilization process.

In some embodiments, a subject formulation includes a humanized anti-factor Bb antibody, and at least one of the above-identified agents (e.g., a surfactant, a buffer, a stabilizer, a tonicity agent) and is essentially free of at least one preservative.

A humanized anti-factor Bb antibody can be utilized in aerosol formulation to be administered via inhalation. A humanized anti-factor Bb antibody can be formulated into pressurized acceptable propellants.

Furthermore, a humanized anti-factor Bb antibody can be made into suppositories by mixing with a variety of bases such as emulsifying bases or water-soluble bases. A humanized anti-factor Bb antibody can be administered rectally via a suppository.

Other modes of administration will also find use with a method of the present disclosure.

For instance, a humanized anti-factor Bb antibody can be formulated in suppositories and, in some embodiments, aerosol and intranasal compositions. For suppositories, the vehicle composition may include traditional binders and carriers.

Intranasal formulations will usually include vehicles that neither cause irritation to the nasal mucosa nor significantly disturb ciliary function. Diluents such as water, aqueous saline or other known substances can be employed. The nasal formulations can also contain a preservative. A surfactant can be present to enhance absorption of a humanized anti-factor Bb antibody by the nasal mucosa.

A humanized anti-factor Bb antibody can be administered as an injectable formulation. Typically, injectable compositions are prepared as liquid solutions or suspensions; solid forms suitable for solution in, or suspension in, liquid vehicles prior to injection can also be prepared. The preparation can also be emulsified, or the antibody encapsulated in liposome vehicles.

In some embodiments, a humanized anti-factor Bb antibody is formulated in a controlled release formulation. Controlled release within the scope of the present disclosure can be taken to mean any one of a number of extended-release dosage forms.

A humanized anti-factor Bb antibody is administered to a subject using a method and route suitable for drug delivery, including in vivo and ex vivo methods, as well as systemic and localized routes of administration.

Conventional and pharmaceutically acceptable routes of administration include, but are not limited to, intranasal, intramuscular, intratracheal, intrathecal, intracranial, subcutaneous, intradermal, topical, intravenous, intraperitoneal, intraarterial (e.g., via the carotid artery), spinal or brain delivery, rectal, nasal, oral, and other enteral and parenteral routes of administration.

An antibody of the present disclosure can be administered to a subject using any available conventional methods and routes suitable for delivery of conventional drugs, including systemic or localized routes. In general, routes of administration contemplated by the present disclosure include, but are not necessarily limited to, enteral, parenteral, or inhalational routes.

In some embodiments, a humanized anti-factor Bb antibody is administered by injection and/or delivery, e.g., to a site in a brain artery or directly into brain tissue. A humanized anti-factor Bb antibody can also be administered directly to a target site e.g., by biolistic delivery to the target site.

A variety of subjects may be treated in accordance with the methods provided herein. Generally, such subjects are "mammals" or "mammalian," where these terms are used broadly to describe organisms which are within the class Mammalia, including the orders carnivores (e.g., cats), herbivores (e.g., cattle, horses, and sheep), omnivores (e.g., dogs, goats, and pigs), rodentia (e.g., mice, guinea pigs, and rats), and primates (e.g., humans, chimpanzees, and monkeys). In some embodiments, a subject has a complement system, such as a mammal, fish, or invertebrate. In some embodiments, a subject is a complement system-containing mammal, fish, or invertebrate companion animal, agricultural animal, work animal, zoo animal, or lab animal. In some embodiments, a subject is a human.

"Treatment" refers to at least an amelioration of the symptoms associated with pathological condition afflicting a subject, where amelioration is used in a broad sense to refer to at least a reduction in the magnitude of a parameter, e.g., symptom, associated with the pathological condition being treated, such as a complement-mediated disease or disorder. As such, treatment also includes situations where the pathological condition, or at least symptoms and/or secondary effects associated therewith, are completely inhibited, e.g., prevented from happening, or stopped, e.g., terminated, such that subject no longer suffers from the pathological condition, or at least the symptoms that characterize the pathological condition.

In some embodiments, a "subject" is a mammal, including, but not limited to, murines (rats, mice), non-human primates, humans, canines, felines, ungulates (e.g., equines, bovines, ovines, porcines, caprines), etc. Also encompassed by these terms are any animal that has a complement system, such as mammals, fish, and some invertebrates. As such these terms include complement system-containing mammal, fish, and invertebrate companion animals, agricultural animals, work animals, zoo animals, and lab animals.

A "biological sample" encompasses a variety of sample types obtained from a subject and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, and/or blood fractions such as plasma and serum. The term "biological sample" also includes solid tissue samples, tissue culture samples, and cellular samples.

The present disclosure provides a device or container suitable for containing a composition comprising a humanized anti-factor Bb antibody for administration to a subject. For example, a humanized anti-factor Bb antibody can be disposed within a container suitable for containing a pharmaceutical composition. The container can be, for example, a bottle (e.g., with a closure device, such as a cap), a blister pack (e.g., which can provide for enclosure of at least one doses per blister), a vial, flexible packaging (e.g., sealed Mylar or plastic bags), an ampule (for single doses in solution), a dropper, a syringe, thin film, and/or a tube. In some embodiments, a container, such as a sterile container, comprises a subject pharmaceutical composition. In some embodiments, the container is a bottle or a syringe. In some embodiments, the container is a bottle. In some embodiments, the container is a syringe. In some embodiments, the device is an injectable device, such as a syringe (e.g., a pre-filled syringe), a pen (e.g., a pre-filled pen), or an electronic injection device (e-Devices).

The present disclosure provides methods of treating a complement-mediated disease or disorder. The methods generally involve administering an effective amount of a humanized anti-factor Bb antibody of the present disclosure to a subject in need thereof. In some embodiments, administration of a humanized anti-factor Bb antibody modulates the activity of the complement pathway activity in a cell, a tissue, or a fluid of a subject, and treats the complement-mediated disease or disorder.

An "effective amount" refers to the amount of an anti-complement factor Bb antibody that, when administered to a mammal or other subject for treating a disease, is sufficient to effect such treatment for the disease. The "therapeutically effective amount" will vary depending on the anti-complement Bb antibody, the disease and its severity and the age, weight, etc., of the subject to be treated.

In some embodiments, an effective amount of a humanized anti-factor Bb antibody of the present disclosure is an amount that is effective to reduce or inhibit complement pathway activity in a cell, tissue, or fluid of the subject.

In some embodiments, an effective amount of a humanized anti-factor Bb antibody of the present disclosure is an amount that is effective to reduce or inhibit formation of MAC in a cell, tissue, or fluid of the subject.

In some embodiments, an effective amount of a humanized anti-factor Bb antibody of the present disclosure is an amount that is effective to reduce or inhibit C3b/Bb-mediated cleavage of C3 in a cell, tissue, or fluid of the subject.

In some embodiments, an effective amount of a humanized anti-factor Bb antibody of the present disclosure is an amount that is effective to reduce or inhibit C3b/Bb-mediated cleavage of C3, and thereby to reduce production of a C3 cleavage product.

In some embodiments, an effective amount of a humanized anti-factor Bb antibody of the present disclosure is an amount that is effective to reduce or inhibit complement AP-mediated lysis of a cell in the subject.

In some embodiments, an effective amount of the humanized anti-factor Bb antibody of the present disclosure is an amount that is effective to reduce or inhibit complement AP-mediated hemolysis in a cell, tissue, or fluid (e.g., RBC-containing fluid) of the subject.

In some embodiments, an effective amount of a humanized anti-factor Bb antibody of the present disclosure is an amount that is effective to reduce or inhibit production of an anaphylatoxin.

In some embodiments, an effective amount of a humanized anti-factor Bb antibody of the present disclosure is an amount that is effective to reduce or inhibit AP-mediated deposition of C3b, C3d, or other C3 split product on a cell or tissue in the subject.

In some embodiments, an effective amount of a humanized anti-factor Bb antibody of the present disclosure is an amount that is effective to reduce or inhibit AP-mediated C3b deposition on a cell or tissue in the subject.

In some embodiments, an effective amount of a humanized anti-factor Bb antibody of the present disclosure is an amount that is effective to reduce or inhibit AP-mediated deposition of C3b, C3d, or other C3 split product on RBCs in the subject.

In some embodiments, an effective amount of a humanized anti-factor Bb antibody of the present disclosure is an amount that is effective to reduce or inhibit AP-mediated C3b deposition on RBCs in the subject.

In some embodiments, a humanized anti-factor Bb antibody of the present disclosure, when administered in at least one doses to a subject in need thereof, reduces the amount of factor Bb in circulation in the subject. For example, a humanized anti-factor Bb antibody of the present disclosure, when administered in at least one doses to a subject in need thereof, may reduce the amount of factor Bb in circulation in the subject by at least 10%, at least 20%, at least 30%, at least 40%, at least 50%, at least 60%, at least 65%, at least 70%, at least 75%, at least 80%, at least 85%, at least 90%, or at least 95%, compared to the amount of factor Bb in circulation in the subject in the absence of administering the humanized anti-factor Bb antibody, or compared to the amount of factor Bb in circulation in the subject before administration of the humanized anti-factor Bb antibody.

In some embodiments, a humanized anti-factor Bb antibody of the present disclosure, when administered in at least one doses to a subject in need thereof, reduces the amount of factor Bb in plasma in the subject. For example, a humanized anti-factor Bb antibody of the present disclosure, when administered in at least one doses to a subject in need thereof, may reduce the amount of factor Bb in plasma in the subject by at least 10%, at least 20%, at least 30%, at least 40%, at least 50%, at least 60%, at least 65%, at least 70%, at least 75%, at least 80%, at least 85%, at least 90%, or at least 95%, compared to the amount of factor Bb in plasma in the subject in the absence of administering the humanized anti-factor Bb antibody, or compared to the amount of factor Bb in plasma in the subject before administration of the humanized anti-factor Bb antibody.

In some embodiments, a method of the present disclosure to treat a subject having a complement-mediated disease or disorder comprises administering to the subject a humanized anti-factor Bb antibody of the present disclosure or a pharmaceutical composition comprising: a) a humanized anti-factor Bb antibody of the present disclosure; and b) a pharmaceutically acceptable excipient suitable for administration to such subject. In some embodiments, the subject is a mammal. In some embodiments, the subject is a human. Administering can be by any route known to those skilled in the art, including those disclosed herein. In some embodiments, administering is intravenous. In some embodiments, administering is intrathecal. In some embodiments, administering is intramuscular. In some embodiments, administering is subcutaneous.

Complement-mediated diseases and disorders that are suitable for treatment with a humanized anti-factor Bb antibody of the present disclosure include diseases and disorders associated with the alternative complement pathway. Studies in preclinical animal models and clinical trials indicate alternative pathway plays an important role in the development of tissue injury and pathogenesis of several conditions (Holers et al., *Immunological Reviews* 223: 300-316; Cao et al., (2016) *Haematologica* 101(11): 1319-1326;

Schubart et al., (2019) *PNAS* 116(16): 7926-7931; Thurman, (2015) *Am J Kidney Dis* 65(1): 156-168; Vriese et al., (2015) *Am J Kidney Dis* 65(1): 156-168; and Gold et al., (2006) *Nat. Genet.* 38(4): 458-462). In some embodiments, complement-mediated diseases that are suitable for treatment with a humanized anti-factor Bb antibody of the present disclosure include, but are not limited to, IgA nephropathy (Berger's disease), atypical hemolytic uremic syndrome (aHUS), paroxysmal nocturnal hemoglobinuria (PNH), idiopathic thrombocytopenic purpura (ITP), thrombotic thrombocytopenic purpura (TTP), lupus nephritis, ANCA vasculitis, membranous nephropathy, C3 glomerulonephritis (C3GN), focal segmental glomerulosclerosis (FSGS), multiple sclerosis, macular degeneration, age-related macular degeneration (AMD), rheumatoid arthritis, antiphospholipid antibody syndrome, asthma, ischemia-reperfusion injury, Type II membranoproliferative GN, spontaneous fetal loss, Pauci-immune vasculitis, epidermolysis bullosa, recurrent fetal loss, and traumatic brain injury.

A humanized anti-factor Bb antibody of the present disclosure can be administered to a subject in need thereof alone (e.g., as monotherapy); or in combination therapy with at least one additional therapeutic agents.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds that can be administered in the same or different formulations, by the same of different routes, and in the same or different dosage form type.

Subjects suitable for treatment with a humanized anti-factor Bb antibody include subjects who have been diagnosed as having a complement-mediated disease or disorder; subjects at greater risk than the general population for developing a complement-mediated disease or disorder (e.g., subjects having a genetic predisposition to developing a complement-mediated disease or disorder). Also included are subjects having any one of the complement-mediated diseases or disorders listed hereinabove. In some embodiments, the subject is an adult human. In some embodiments, the subject is a human child.

EXAMPLES

Example 1: Humanization of a Mouse Monoclonal Anti-Factor Bb Antibody

Variable region genes from the parent anti-factor Bb antibody (see Table 1) hybridoma were amplified, cloned and sequenced, resulting in the identification of a single unique VH domain and a single unique Vκ domain.

Initially, three humanized $V_H$ regions and five humanized Vκ regions designed using COMPOSITE HUMAN ANTIBODY™ technology were cloned into IgG4v1 heavy chain and kappa light chain vectors. The parent antibody, two control antibodies and all 15 humanized antibody combinations were expressed transiently in HEK EBNA cells.

In order to assess the binding of all humanized variants, single cycle kinetic analysis was performed on supernatants from transfected cell cultures. Kinetic experiments were performed on a BIACORE™ T200 (Ser. No. 1909913) running BIACORE™ T200 Control software V2. 0. 1 and Evaluation software V3.0 (GE® Healthcare, Uppsala, Sweden). All single cycle kinetic experiments were run at 25° C. with HBS-P+ running buffer (pH 7.4) (GE® Healthcare, Little Chalfont, UK).

Antibodies were diluted in running buffer to a final concentration of 1 μg/ml, based on concentrations assessed by ELISA titer. At the start of each cycle, antibodies were loaded onto Fc2, Fc3 and Fc4 of the Protein A chip (GE® Healthcare, Little Chalfont, UK). IgGs were captured at a flow rate of 10 μl/min to give an immobilization level (RL) of ~63 RU, the theoretical value to obtain an Rmax of ~50 RU. The surface was then allowed to stabilize. Single cycle kinetic data was obtained with factor Bb (CompTech, Tyler, USA) as the analyte at a flow rate of 30 μl/min to minimize any potential mass transport limitations. Multiple repeats with the reference chimeric antibody were performed to check the stability of the surface and analyte over the kinetic cycles. The signal from the reference channel Fc1 (no antibody) was subtracted from that of Fc2, Fc3 and Fc4 to correct for differences in non-specific binding to a reference surface. A four point, two-fold dilution range from 0.78 nM to 6.25 nM factor Bb without regeneration between each concentration was used. The association phase for the four injections of increasing concentrations of factor Bb was monitored for 200 seconds each time and a single dissociation phase was measured for 200 seconds following the last injection of factor Bb. Regeneration of the Protein A surface was conducted using two injections of 10 mM glycine-HCL pH 1.5.

The sensorgrams and fitted data for the single cycle kinetics are shown in FIGS. 1A-1D and the kinetic parameters measured for the interaction of factor Bb with each antibody are shown in Table 7. The relative $K_D$ was calculated by dividing the $K_D$ of the VH0/Vκ0 reference antibody by that of the humanized variant assayed in the same experiment.

TABLE 7

Single Cycle Kinetic Parameters of the Humanized Variants and Reference Antibodies Binding to Factor Bb.

| Antibody | ka (1/Ms) | kd (1/s) | KD (M) | Chi$^2$ (RU$^2$) | Relative KD |
|---|---|---|---|---|---|
| VH0/Vκ0 (Chimeric) | 5.85 × 10$^5$ | 1.03 × 10$^{-3}$ | 1.76 × 10$^{-9}$ | 0.0134 | 1.00 |
| VH0/Vκ1 (control) | 5.86 × 10$^5$ | 1.57 × 10$^{-3}$ | 2.68 × 10$^{-9}$ | 0.00688 | 1.52 |
| VH1/Vκ0 (control) | 3.76 × 10$^5$ | 1.16 × 10$^{-3}$ | 3.09 × 10$^{-9}$ | 0.00605 | 1.76 |
| VH1/Vκ1 | 5.74 × 10$^5$ | 2.87 × 10$^{-3}$ | 5.01 × 10$^{-9}$ | 0.00228 | 2.85 |
| VH1/Vκ2 | 4.81 × 10$^5$ | 2.51 × 10$^{-3}$ | 5.22 × 10$^{-9}$ | 0.00381 | 2.97 |
| VH1/Vκ3 | 6.75 × 10$^5$ | 2.63 × 10$^{-3}$ | 3.90 × 10$^{-9}$ | 0.00488 | 2.22 |
| VH1/Vκ4 | 4.51 × 10$^5$ | 2.94 × 10$^{-3}$ | 6.52 × 10$^{-9}$ | 0.0029 | 3.70 |
| VH1/Vκ5 | 2.25 × 10$^5$ | 2.01 × 10$^{-3}$ | 8.96 × 10$^{-9}$ | 0.00803 | 5.09 |

TABLE 7-continued

Single Cycle Kinetic Parameters of the Humanized Variants
and Reference Antibodies Binding to Factor Bb.

| Antibody | ka (1/Ms) | kd (1/s) | KD (M) | Chi² (RU²) | Relative KD |
|---|---|---|---|---|---|
| VH2/Vκ1 | $1.80 \times 10^5$ | $3.73 \times 10^{-3}$ | $2.07 \times 10^{-8}$ | 0.00991 | 11.78 |
| VH2/Vκ2 | $2.34 \times 10^5$ | $3.26 \times 10^{-3}$ | $1.39 \times 10^{-8}$ | 0.00327 | 7.90 |
| VH2/Vκ3 | $2.52 \times 10^5$ | $3.07 \times 10^{-3}$ | $1.22 \times 10^{-8}$ | 0.00259 | 6.93 |
| VH2/Vκ4 | $3.39 \times 10^5$ | $3.68 \times 10^{-3}$ | $1.09 \times 10^{-8}$ | 0.00377 | 6.19 |
| VH2/Vκ5 | $2.25 \times 10^5$ | $3.75 \times 10^{-3}$ | $1.66 \times 10^{-8}$ | 0.00241 | 9.43 |
| VH3/Vκ1 | $2.91 \times 10^5$ | $4.04 \times 10^{-3}$ | $1.39 \times 10^{-8}$ | 0.00393 | 7.90 |
| VH3/Vκ2 | $2.36 \times 10^5$ | $3.77 \times 10^{-3}$ | $1.60 \times 10^{-8}$ | 0.0019 | 9.09 |
| VH3/Vκ3 | $2.20 \times 10^5$ | $3.29 \times 10^{-3}$ | $1.49 \times 10^{-8}$ | 0.00359 | 8.47 |
| VH3/Vκ4 | $2.67 \times 10^5$ | $4.60 \times 10^{-3}$ | $1.73 \times 10^{-8}$ | 0.00332 | 9.83 |
| VH3/Vκ5 | $2.85 \times 10^5$ | $4.51 \times 10^{-3}$ | $1.58 \times 10^{-8}$ | 0.00257 | 8.98 |

BIACORE™ analysis showed that all humanized variants bound to factor Bb, however, in all cases the relative $K_D$ was greater than two-fold different than the chimeric suggesting that some binding affinity had been lost. In order to address this, an additional four heavy chain (VH4 to VH7) and two light chain (Wκ6 to Vκ7) sequences were designed and cloned into the appropriate expression vector. Variant sequences are shown in Tables 2 and 3.

Expression and Single Cycle Kinetic Analysis of Redesigned Variants

Five control antibodies (VH0/Vκ6, VH0/Vκ7, VH5/Vκ0, VH6/Vκ0, VH7/Vκ0) and combinations of humanized heavy and light chains (a total of eight humanized pairings, Table 8) were transiently transfected into HEK EBNA adherent cells (ATCC® Cat. No. CRL- 10852™) using a PEI transfection method. IgG supernatant titres were monitored by IgG ELISA (Table 9) and transfections were cultured for up to 10 days prior to harvesting supernatants.

TABLE 8

Antibody Titers of Variants Produced
by Transient Transfection (μg/mL).

| | Vκ0 | Vκ6 | Vκ7 |
|---|---|---|---|
| VH0 | — | 60.6 | 29.9 |
| VH4 | — | 4.71 | 4.75 |
| VH5 | 26.9 | 38.1 | 35.5 |
| VH6 | 5.8 | 8.5 | 9.7 |
| VH7 | 17.9 | 36.1 | 39.8 |

Figure 2A:
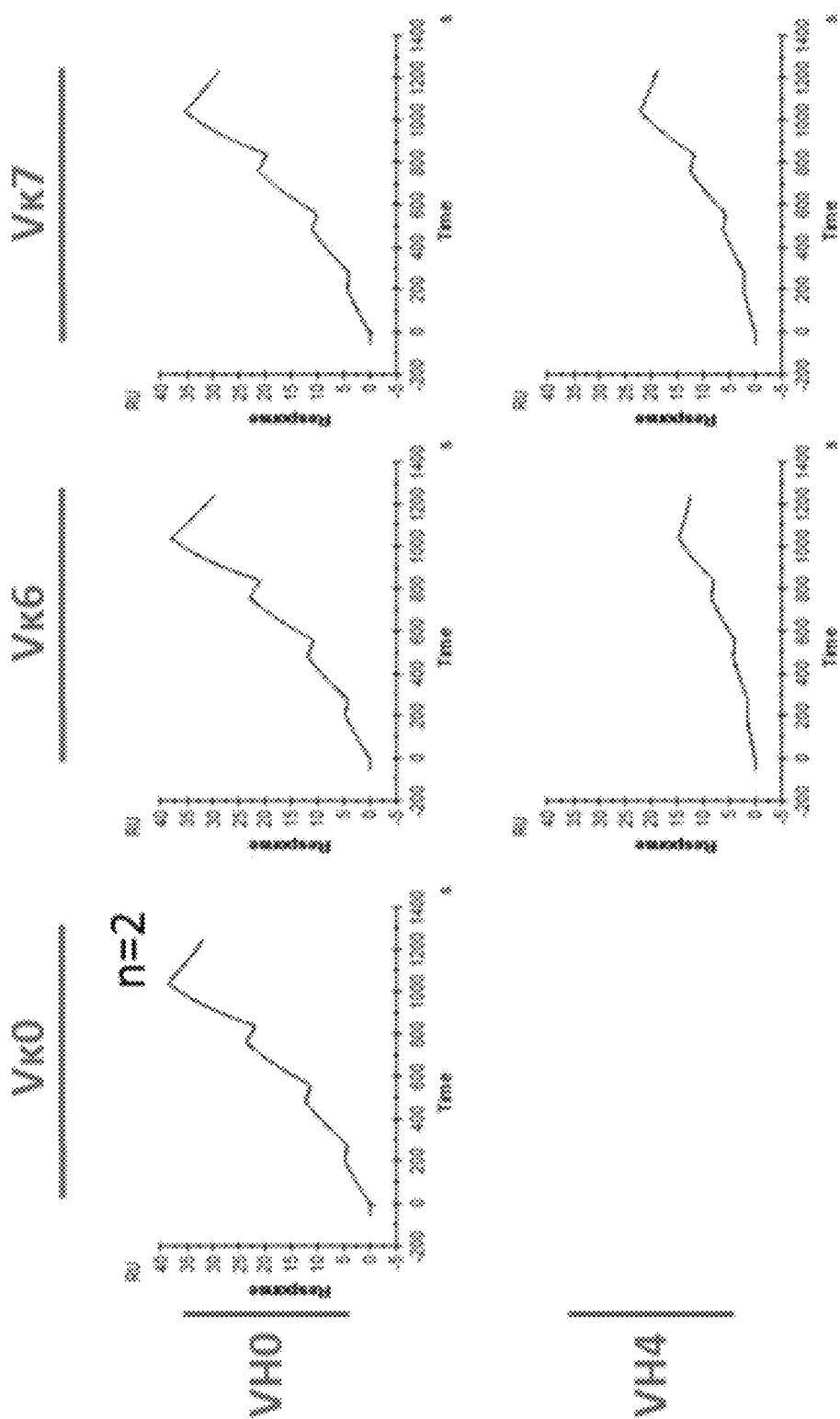
FIGS. 2A-2C show binding of humanized variants (Group 2) to factor Bb using single cycle kinetics. Raw sensorgrams and fitted curves (1:1 binding model) for redesigned variants and control antibodies binding to factor Bb are shown. Kinetic analysis was carried out on a BIACORE™ T200. Each antibody was captured on a Protein A CM5 chip before increasing concentrations of factor Bb were injected and a single off-rate was determined.
Figure 2B:
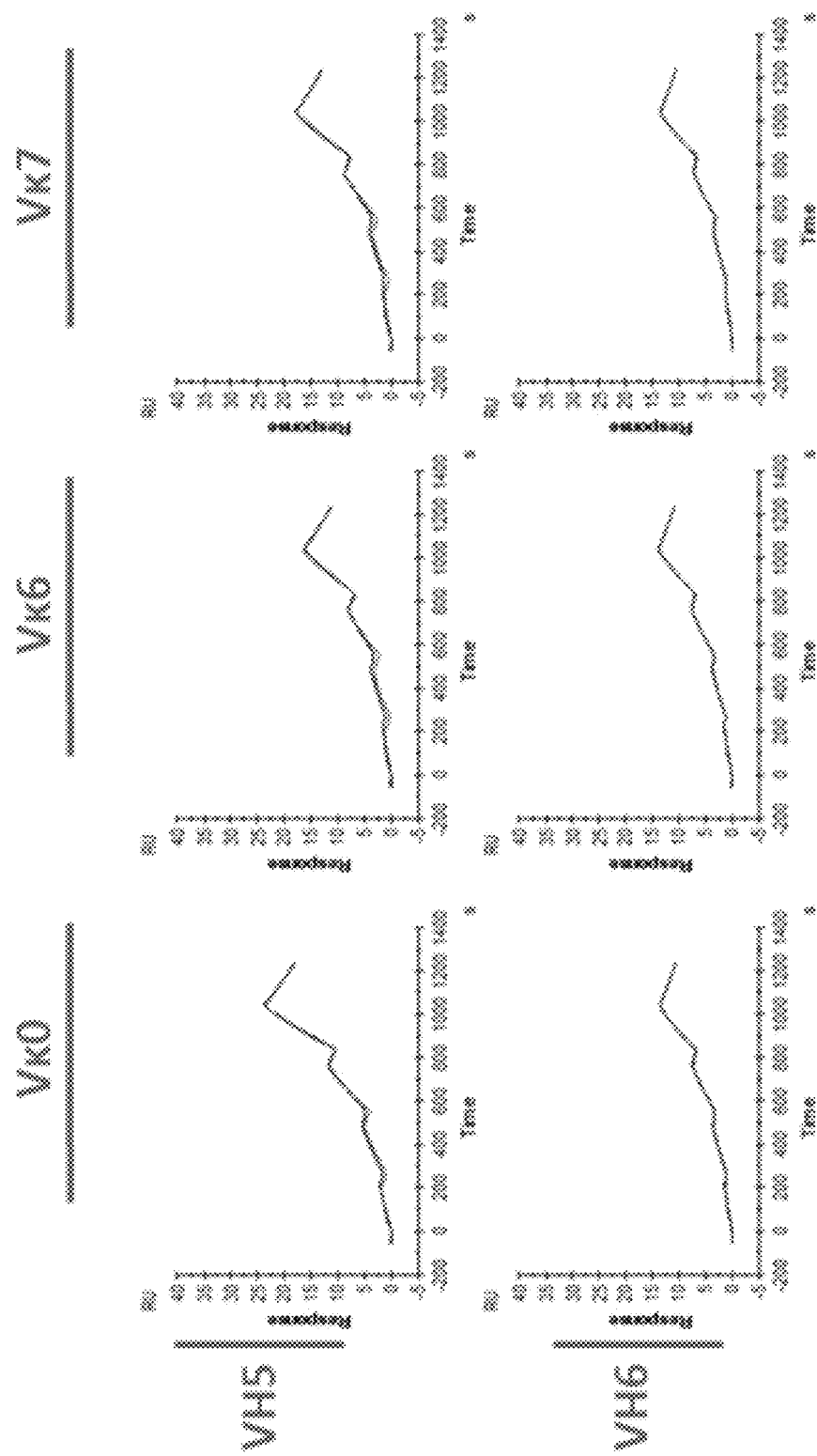
Figure 2C:
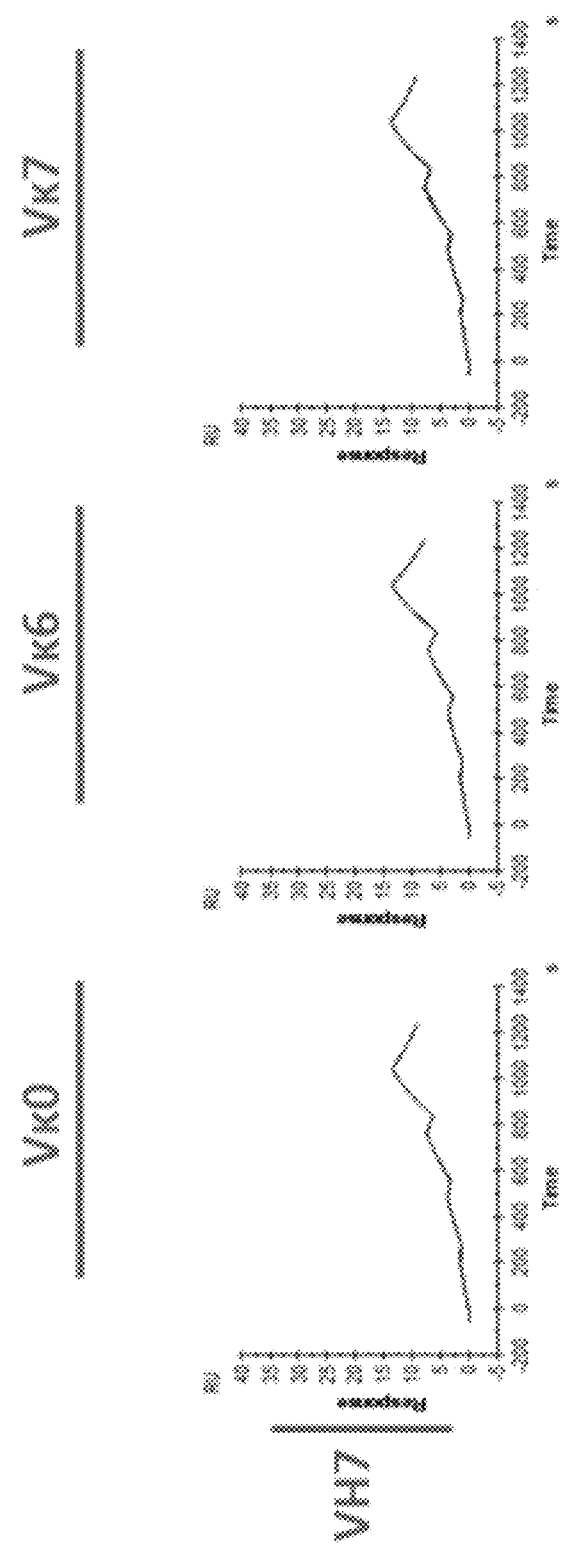

Single cycle kinetics using cell culture supernatants were performed as described above. The sensorgrams and fitted data for the single cycle kinetics are shown in FIGS. 2A-2C. All variants were shown to bind to factor Bb. Single cycle kinetics data (Table 9) demonstrated that five antibodies ($V_H4$/Vκ6, $V_H4$/Vκ7, $V_H6$/Vκ6 $V_H6$/Vκ7 and $V_H7$/Vκ7) bound to factor Bb within ~two-fold of the reference chimeric antibody. The relative $K_D$ was calculated by dividing the $K_D$ of the VH0/Vκ0 reference antibody by that of the humanized variant assayed in the same experiment.

TABLE 9

Single Cycle Kinetic Parameters of the Humanized Variants
and Reference Antibodies Binding to Factor Bb.

| Antibody | ka (1/Ms) | kd (1/s) | KD (M) | Chi² (RU²) | Relative KD |
|---|---|---|---|---|---|
| VH0/Vκ0 | $5.35 \times 10^5$ | $9.49 \times 10^{-4}$ | $1.77 \times 10^{-9}$ | 0.00854 | 1.00 |
| VH0/Vκ3 | $5.63 \times 10^5$ | $1.28 \times 10^{-3}$ | $2.27 \times 10^{-9}$ | 0.00587 | 1.28 |

TABLE 9-continued

Single Cycle Kinetic Parameters of the Humanized Variants
and Reference Antibodies Binding to Factor Bb.

| Antibody | ka (1/Ms) | kd (1/s) | KD (M) | Chi² (RU²) | Relative KD |
|---|---|---|---|---|---|
| VH0/Vκ6 | $5.34 \times 10^5$ | $1.26 \times 10^{-3}$ | $2.37 \times 10^{-9}$ | 0.00766 | 1.34 |
| VH0/Vκ7 | $4.96 \times 10^5$ | $1.05 \times 10^{-3}$ | $2.11 \times 10^{-9}$ | 0.00335 | 1.19 |
| VH4/Vκ6 | $3.87 \times 10^5$ | $8.59 \times 10^{-4}$ | $2.22 \times 10^{-9}$ | 0.00473 | 1.25 |
| VH4/Vκ7 | $3.86 \times 10^5$ | $9.03 \times 10^{-4}$ | $2.34 \times 10^{-9}$ | 0.00497 | 1.32 |
| VH5/Vκ0 | $3.49 \times 10^3$ | $1.45 \times 10^{-3}$ | $4.16 \times 10^{-7}$ | 0.11 | 235.03 |
| VH5/Vκ6 | $1.33 \times 10^5$ | $1.73 \times 10^{-2}$ | $1.30 \times 10^{-7}$ | 0.173 | 73.45 |
| VH5/Vκ7 | $3.20 \times 10^3$ | $1.66 \times 10^{-3}$ | $5.21 \times 10^{-7}$ | 0.153 | 294.35 |
| VH6/Vκ0 | $5.98 \times 10^5$ | $1.97 \times 10^{-3}$ | $3.29 \times 10^{-9}$ | 0.00485 | 1.86 |
| VH6/Vκ6 | $4.12 \times 10^5$ | $1.58 \times 10^{-3}$ | $3.84 \times 10^{-9}$ | 0.00588 | 2.17 |
| VH6/Vκ7 | $6.30 \times 10^5$ | $2.21 \times 10^{-3}$ | $3.51 \times 10^{-9}$ | 0.00377 | 1.98 |
| VH7/Vκ0 | $2.74 \times 10^5$ | $2.07 \times 10^{-3}$ | $7.53 \times 10^{-9}$ | 0.00634 | 4.25 |
| VH7/Vκ6 | $1.68 \times 10^5$ | $3.03 \times 10^{-3}$ | $1.80 \times 10^{-8}$ | 0.00587 | 10.17 |
| VH7/Vκ7 | $4.83 \times 10^6$ | $1.17 \times 10^{-2}$ | $2.42 \times 10^{-9}$ | 0.0384 | 1.37 |

Purification of Antibodies

Figure 3:
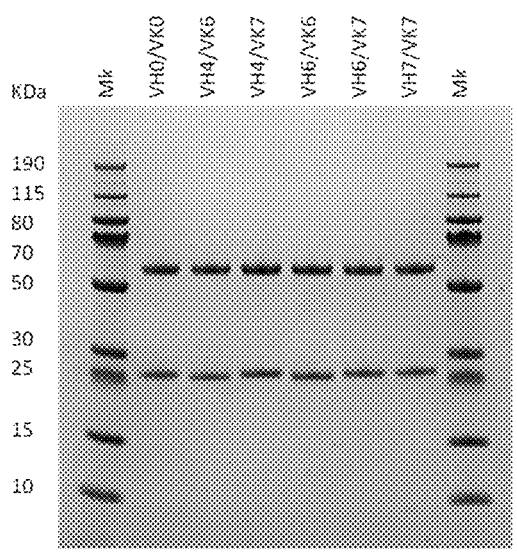
FIG. 3 shows SDS-PAGE gels of Protein A/Post-SEC-purified antibodies. 1 µg of each reduced antibody sample was loaded on a NuPage 4-12% Bis-Tris gel (THERMOFISHER®, Loughborough, UK) and run at 200 V for 35 minutes. Gels were stained with INSTANTBLUE® (Expedeon, Swavesey, UK). Mk: PAGERULER™ Plus pre-stained protein ladder (THERMOFISHER®, Loughborough, UK).

VH4/Vκ6, VH4/Vκ7, VH6/Vκ6 VH6/Vκ7 and VH7/Vκ7 as well as the chimeric antibody were purified from cell culture supernatants on Protein A sepharose columns (GE® Healthcare, Little Chalfont, UK), followed by size exclusion chromatography using a 16/60 Superdex 200 column (GE® Healthcare, Little Chalfont, UK) using PBS pH 7.4 as the mobile phase. Antibodies were quantified by OD280 nm using an extinction coefficient based on the predicted amino acid sequence. Reduced antibodies were analyzed using SDS-PAGE by loading 1 μg of each antibody on the gel (FIG. 3) and bands corresponding to the profile of a typical antibody were observed.

Multicycle Kinetics Analysis of Antibodies

Figure 4A:
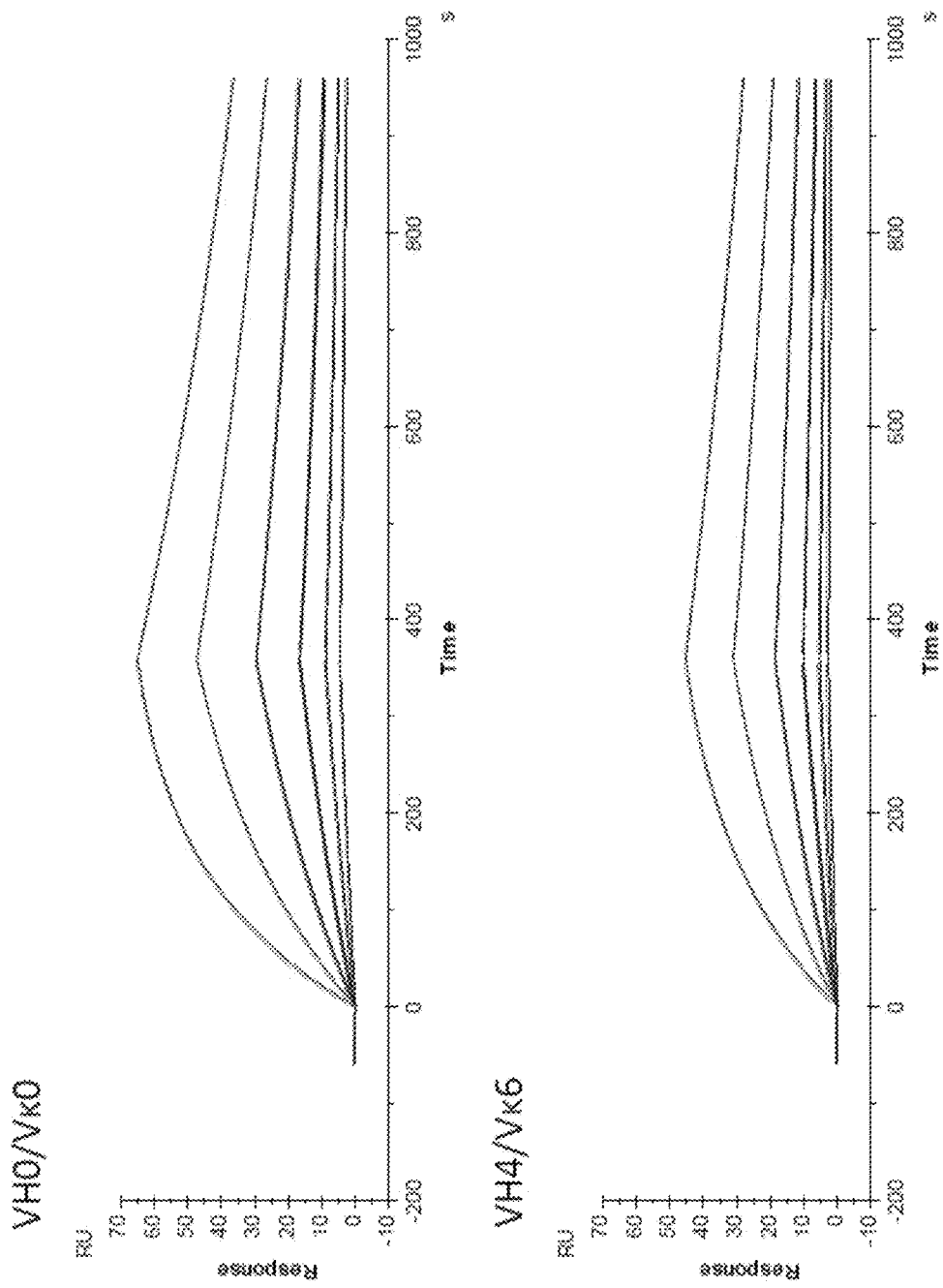
FIGS. 4A-4C show binding of lead antibodies (all from Group 2) to factor Bb using multi-cycle kinetics. Multiple cycle sensorgrams data and fitted curves (1:1 binding model) are shown for the humanized variants binding to factor Bb.
Figure 4B:
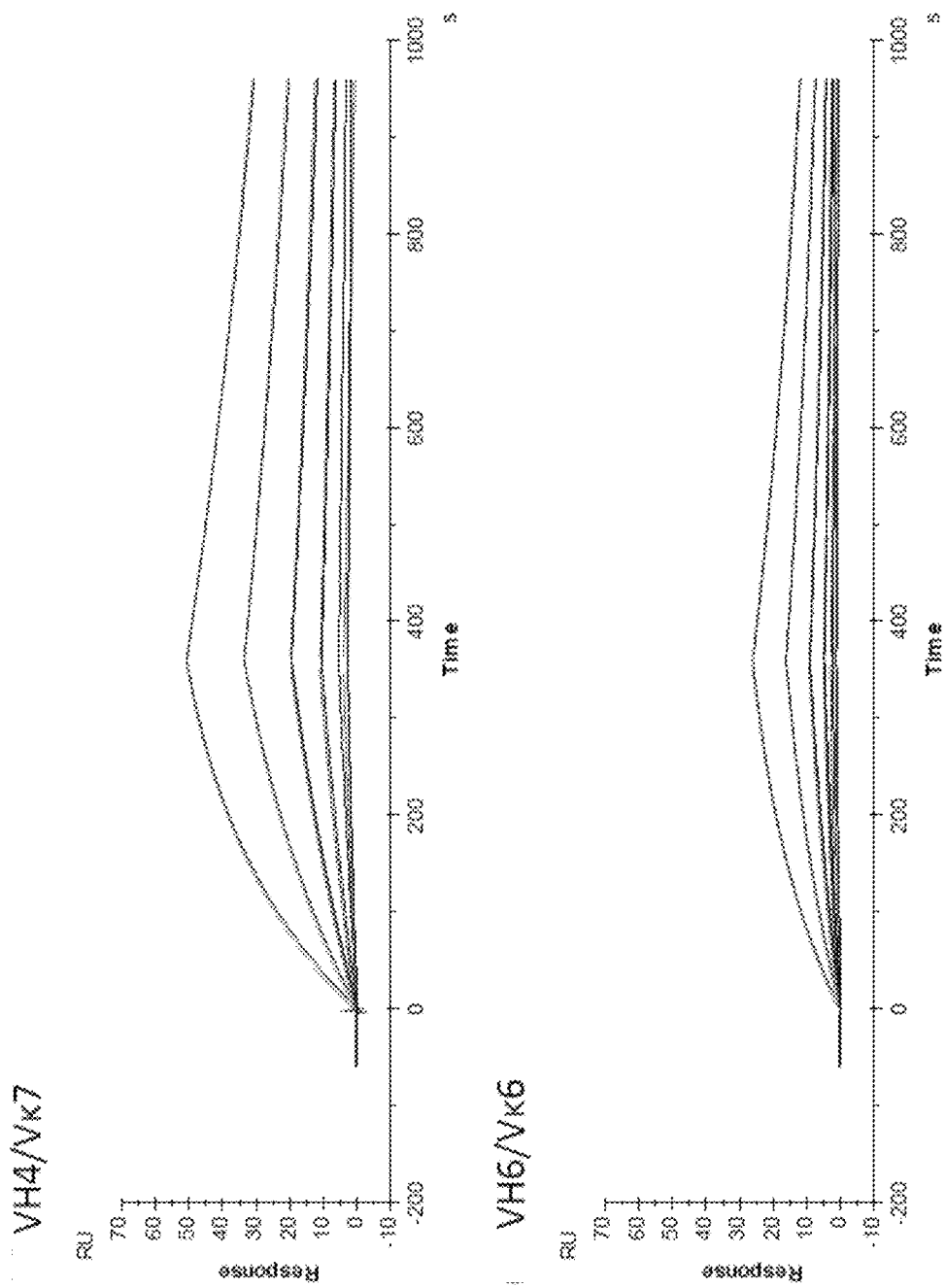
Figure 4C:
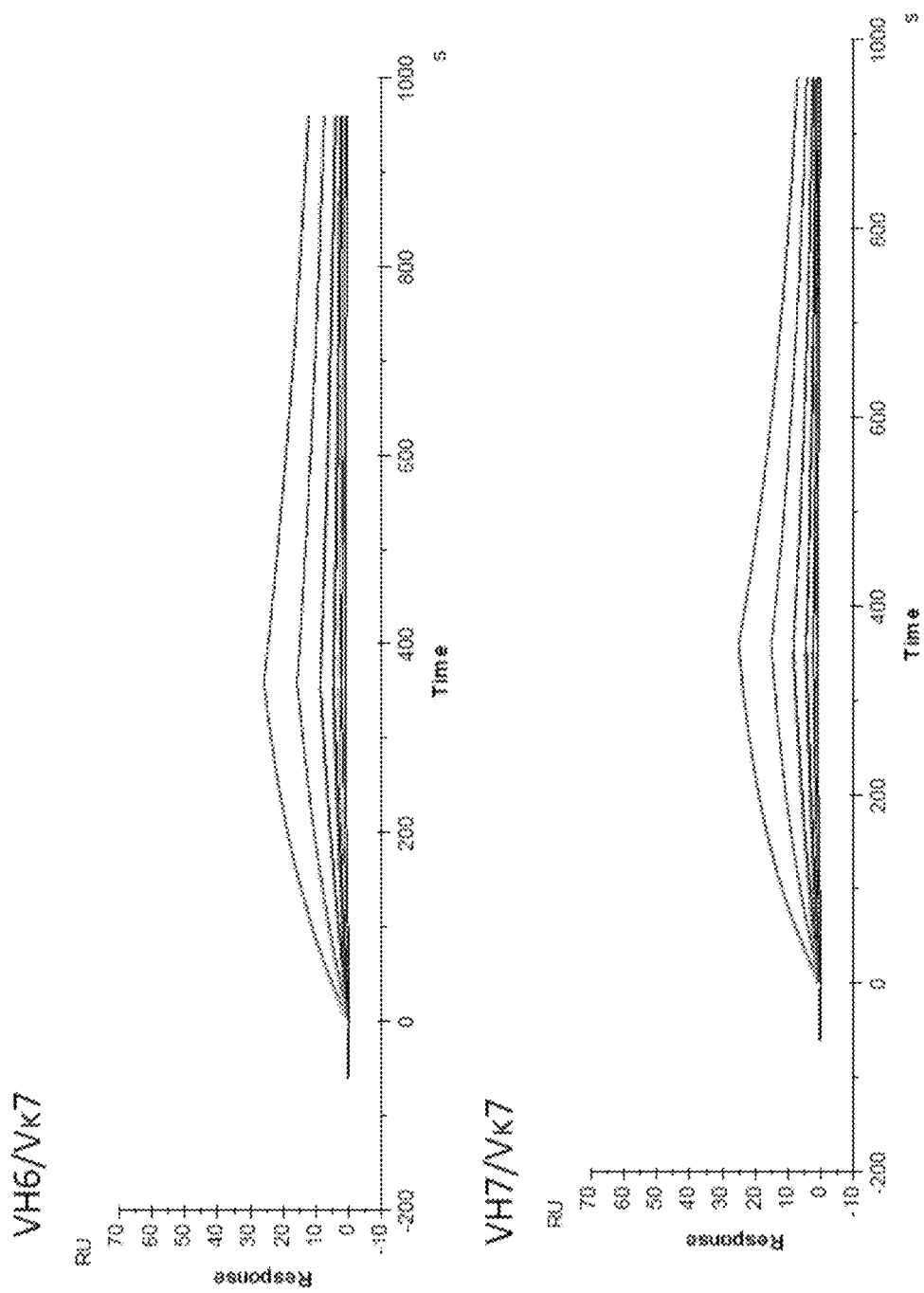

In order to establish an accurate affinity for factor Bb, multicycle kinetics analysis was performed on the purified chimeric antibody and the five lead antibodies using a BIACORE™ T200 (Ser. No. 1909913) instrument running BIACORE™ T200 Evaluation Software V3.0. 1 (Uppsala, Sweden). Antibodies were diluted in running buffer to a final concentration of 0.5 μg/ml. At the start of each cycle, antibodies were loaded onto Fc2, Fc3 and Fc4 of the Protein A chip (GE® Healthcare, Little Chalfont, UK). IgGs were captured at a flow rate of 10 μl/min to give an immobilisation level (RL) of ~63 RU, the theoretical value to obtain an Rmax of ~50 RU. The surface was then allowed to stabilize. Kinetic data was obtained with factor Bb as analyte and using a flow rate of 30 μl/min to minimize any potential mass transfer effects. Multiple repeats of a blank and a repeat of a single concentration of the analyte were programmed into the kinetic run in order to check the stability of both the surface and analyte over the kinetic cycles. For kinetic analysis, a two-fold dilution range was selected from 12.5 nM to 0.391 nM factor Bb. The association phase of factor Bb was monitored for 360 seconds and the dissociation phase was monitored for 600 seconds. Regeneration of the Protein A surface was conducted using two injections of 10 mM glycine-HCL pH 1.5. The signal from the reference channel Fc1 was subtracted from that of Fc2, Fc3 and Fc4 to correct for differences in non-specific binding to a reference surface, and a global Rmax parameter was used in the 1-to-1 binding model. The sensorgrams and fitted data for the binding of chimeric antibodies and humanized variants to factor Bb are shown in FIGS. 4A-4C. The relative $K_D$ was calculated by dividing the $K_D$ of the humanized variants by that of the chimeric antibody on the same chip. The kinetic parameters measured for the interaction of factor Bb with chimeric antibodies and humanized variants are shown in Table 10. Two humanized variants, VH4/Vκ6 and VH4/Vκ7 (bold), showed relative $K_D$s within two-fold of the reference chimeric antibody.

TABLE 10

Multiple Cycle Kinetic Parameters of the Humanized Variants and Reference Antibodies Binding to Factor Bb

| Antibody | ka (1/Ms) | kd (1/s) | KD (M) | Chi² (RU²) | Relative KD |
|---|---|---|---|---|---|
| VH0/Vκ0 | $4.87 \times 10^5$ | $9.69 \times 10^{-4}$ | $1.99 \times 10^{-9}$ | 0.0515 | 1.00 |
| VH4/Vκ6 | $3.76 \times 10^5$ | $8.05 \times 10^{-4}$ | $2.14 \times 10^{-9}$ | 0.0389 | 1.08 |
| VH4/Vκ7 | $3.22 \times 10^5$ | $8.41 \times 10^{-4}$ | $2.61 \times 10^{-9}$ | 0.645 | 1.31 |
| VH0/Vκ0 | $5.00 \times 10^5$ | $9.54 \times 10^{-4}$ | $1.91 \times 10^{-9}$ | 0.033 | 1.00 |
| VH6/Vκ6 | $2.51 \times 10^5$ | $1.30 \times 10^{-3}$ | $5.17 \times 10^{-9}$ | 0.0307 | 2.71 |
| VH6/Vκ7 | $2.18 \times 10^5$ | $1.24 \times 10^{-3}$ | $5.70 \times 10^{-9}$ | 0.0692 | 2.98 |
| VH0/Vκ0 | $4.95 \times 10^5$ | $9.40 \times 10^{-4}$ | $1.90 \times 10^{-9}$ | 0.0442 | 1.00 |
| VH7/Vκ7 | $2.22 \times 10^5$ | $2.11 \times 10^{-3}$ | $9.51 \times 10^{-9}$ | 0.0219 | 5.01 |

Factor Bb Competition ELISA

Lead purified variants and chimeric antibodies were tested for their binding to factor Bb using competition against murine parental antibody.

Factor Bb was diluted in 1x PBS to 1.0 µg/ml and 100 µl/well was coated overnight at 4° C. on a 96-well ELISA plate. The following day the plates were blocked for two hours at room temperature with 1% casein/PBS before washing 2x with PBS pH 7.4. In a 96-well dilution plate a fixed concentration of murine parental antibody (0.5 µg/ml, final concentration) was added in equal volume to a four-fold titration series of test antibody (starting from 45 µg/ml to 0.01 µg/ml, final concentration) diluted in blocking buffer. After washing the plate 3x with PBS-T, 100 µl of chimeric/test antibody mix was added to the ELISA plate. After incubating at room temperature for one hour, the plate was washed 3x with PBS-T and 100 µl of anti-mouse IgG Fc-Specific HRP (SIGMA®, Dorset, UK) diluted 1:1000 in PBS-T was applied for one hour at room temperature to detect bound mouse antibody. For color development, the plate was washed 3x with PBS-T following which 100 µl of TMB substrate was added and incubated for approximately five minutes at room temperature. The reaction was stopped with 50 µl of 3.0 M hydrochloric acid and absorbance was read immediately using a DYNEX® plate reader at 450 nm.

Figure 5:
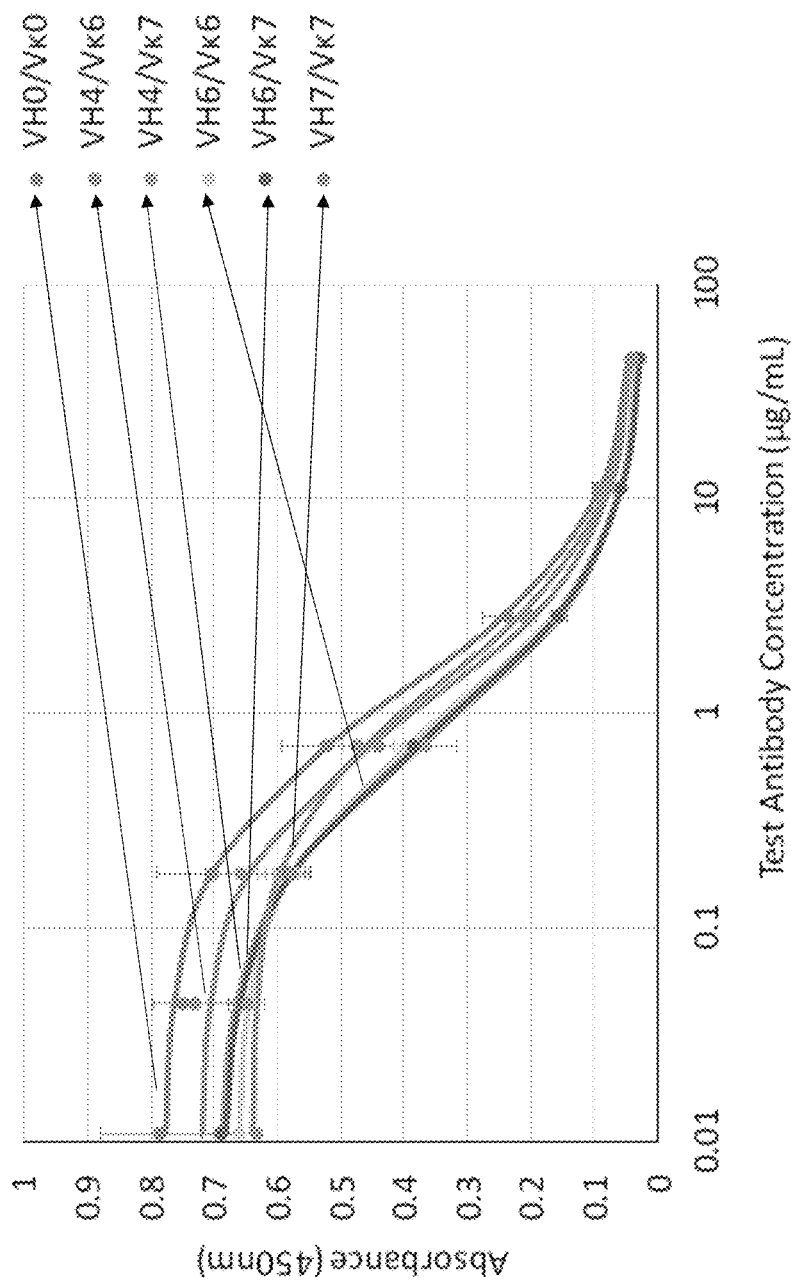
FIG. 5 shows factor Bb competition enzyme-linked immunosorbent assay (ELISA) of humanized variants against parental antibody. A dilution series of the anti-factor Bb variants was tested against a fixed concentration of murine parental antibody for binding to factor-Bb. Bound murine antibody was detected using anti-mouse peroxidase conjugate and tetramethylbenzidine (TMB) substrate.

The results were plotted and are shown in FIG. 5. $IC_{50}$ values were calculated for each variant and relative $IC_{50}$ values were calculated by dividing the $IC_{50}$ of the humanized variant by that of the chimeric antibody assayed on the same plate (Table 11). All lead variants demonstrated $IC_{50}$ values within two-fold of the parent antibody.

TABLE 11

Half Maximal Inhibitory Concentration (IC50) Values Obtained from Competition ELISA of Humanized Leads to Factor Bb.

| Variant | IC50 (nM) | Relative IC50 (nM) |
|---|---|---|
| VH0/Vκ0 | 1.23 | 1.00 |
| VH4/Vκ6 | 1.02 | 0.83 |
| VH4/Vκ7 | 0.75 | 0.61 |
| VH6/Vκ6 | 0.93 | 0.75 |
| VH6/Vκ7 | 0.82 | 0.66 |
| VH7/Vκ7 | 1.43 | 1.16 |

Example 2: Activity of Humanized Variants

Inhibition of WIESLAB® AP by Anti-Factor Bb Humanized Variants in Human Serum

Figure 6A:
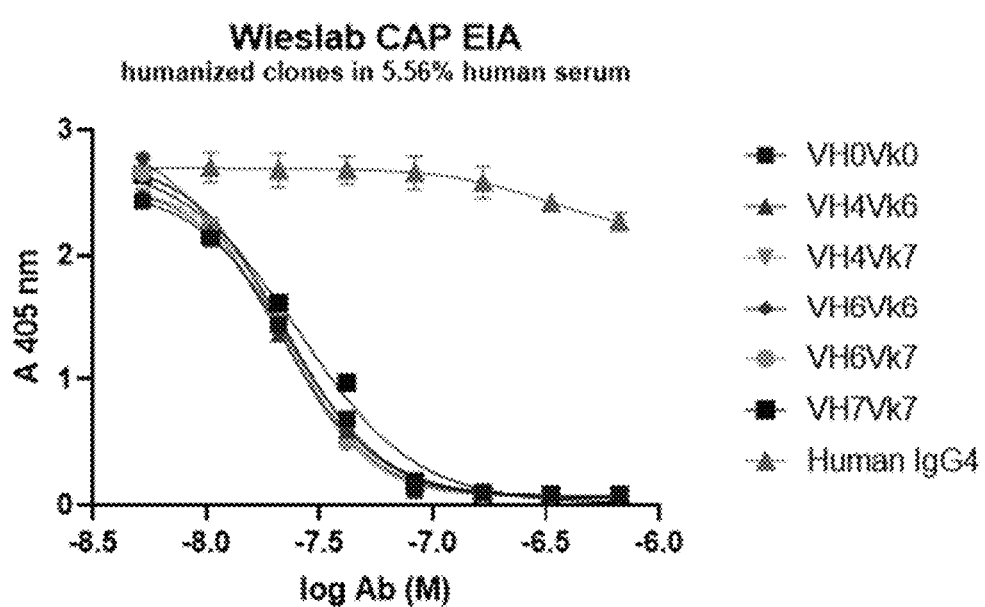
FIGS. 6A-6C show activity of humanized anti-factor Bb antibodies in WIESLAB® Complement Alternative Pathway (CAP) (FIGS. 6A) and AP-mediated hemolysis (FIGS. 6B-6C) using human serum.

The ability of the humanized variants to inhibit complement AP activity was measured using the Complement System Alternative Pathway WIESLAB® kit. In this plate-based assay, lipopolysaccharide (LPS) coated wells lead to specifically activation of the alternative pathway with detection of membrane attack complex (MAC) deposition serving as the readout. 5.56% normal human serum (NHS) was incubated with a dilution series of the parental antibody and humanized variants along with a human IgG4 control antibody starting at 100 µg/mL. OD 405 nm was measured and compared to the kit positive and negative controls. Data were plotted relative to the plate positive control (FIG. 6A). All humanized variants showed inhibition of AP-mediated MAC deposition similar to the parental antibody in human serum (Table 13).

TABLE 12

Activity of Humanized anti-factor Bb Antibodies in WIESLAB ® AP Assay.

| Variant | AP Assay IC50 (M) |
|---|---|
| VH0/Vk0 | $2.4 \times 10^{-8}$ |
| VH4/Vk6 | $2.2 \times 10^{-8}$ |
| VH4/Vk7 | $2.3 \times 10^{-8}$ |
| VH6/Vk6 | $1.9 \times 10^{-8}$ |
| VH6/Vk7 | $2.1 \times 10^{-8}$ |
| VH7/Vk7 | $2.5 \times 10^{-8}$ |

Figure 6B:
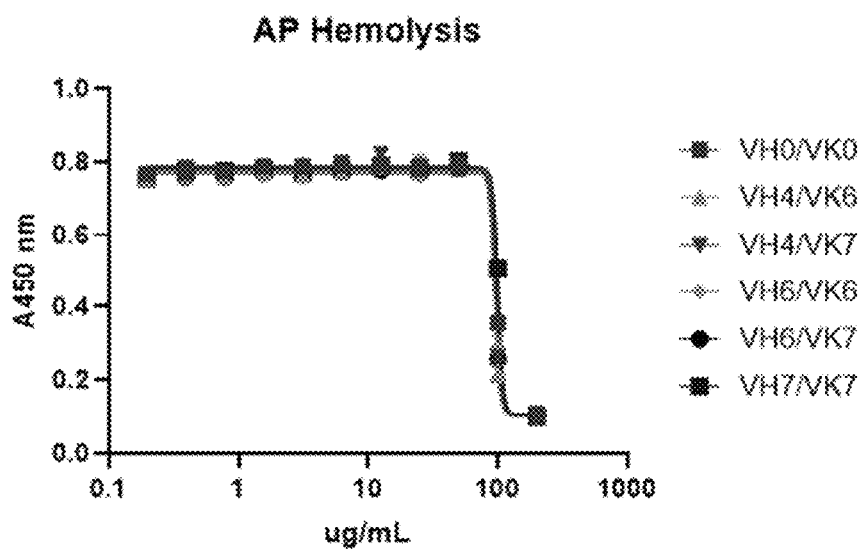
Figure 6C:
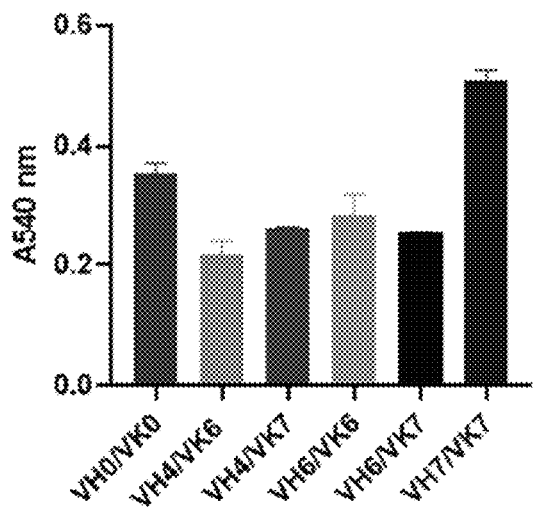
Figure 7A:
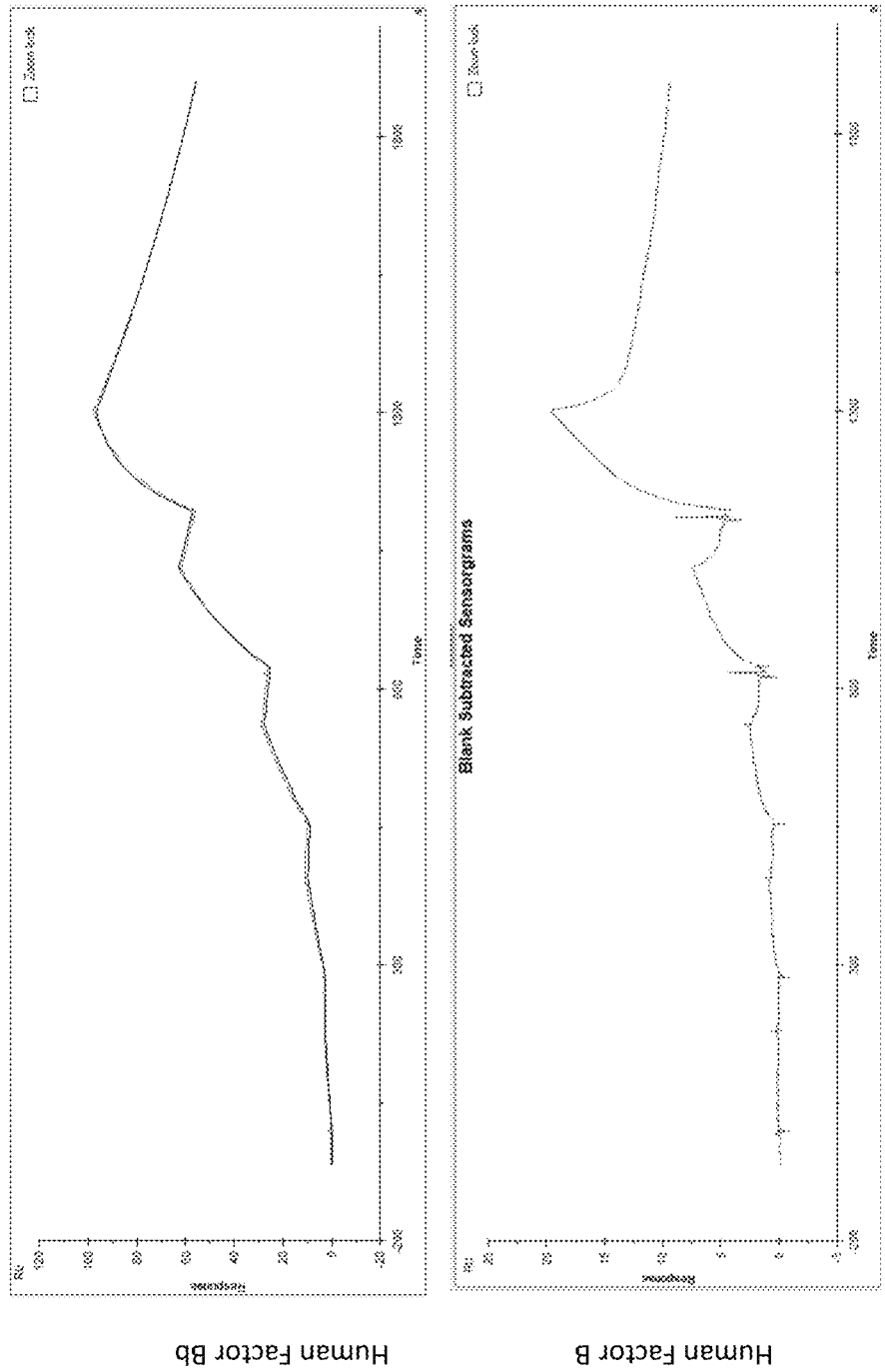
FIGS. 7A-7D show specificity of lead humanized variants to active form (factor Bb) of human factor B (FIGS. 7A and 7B) or cynomolgus monkey factor B (FIGS. 7C and 7D) by surface plasmon resonance.
Figure 7B:
Figure 7C:
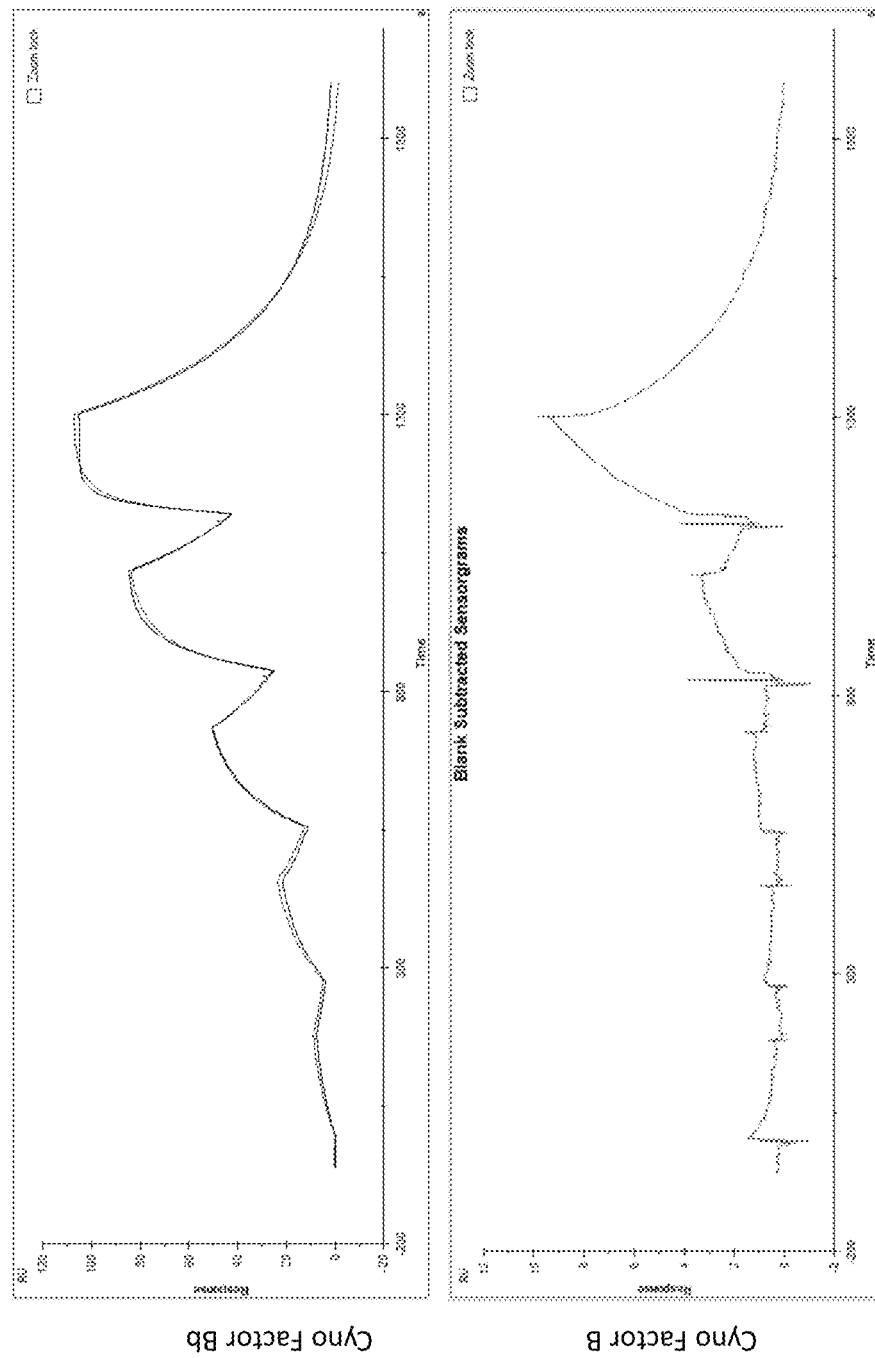
Figure 7D:
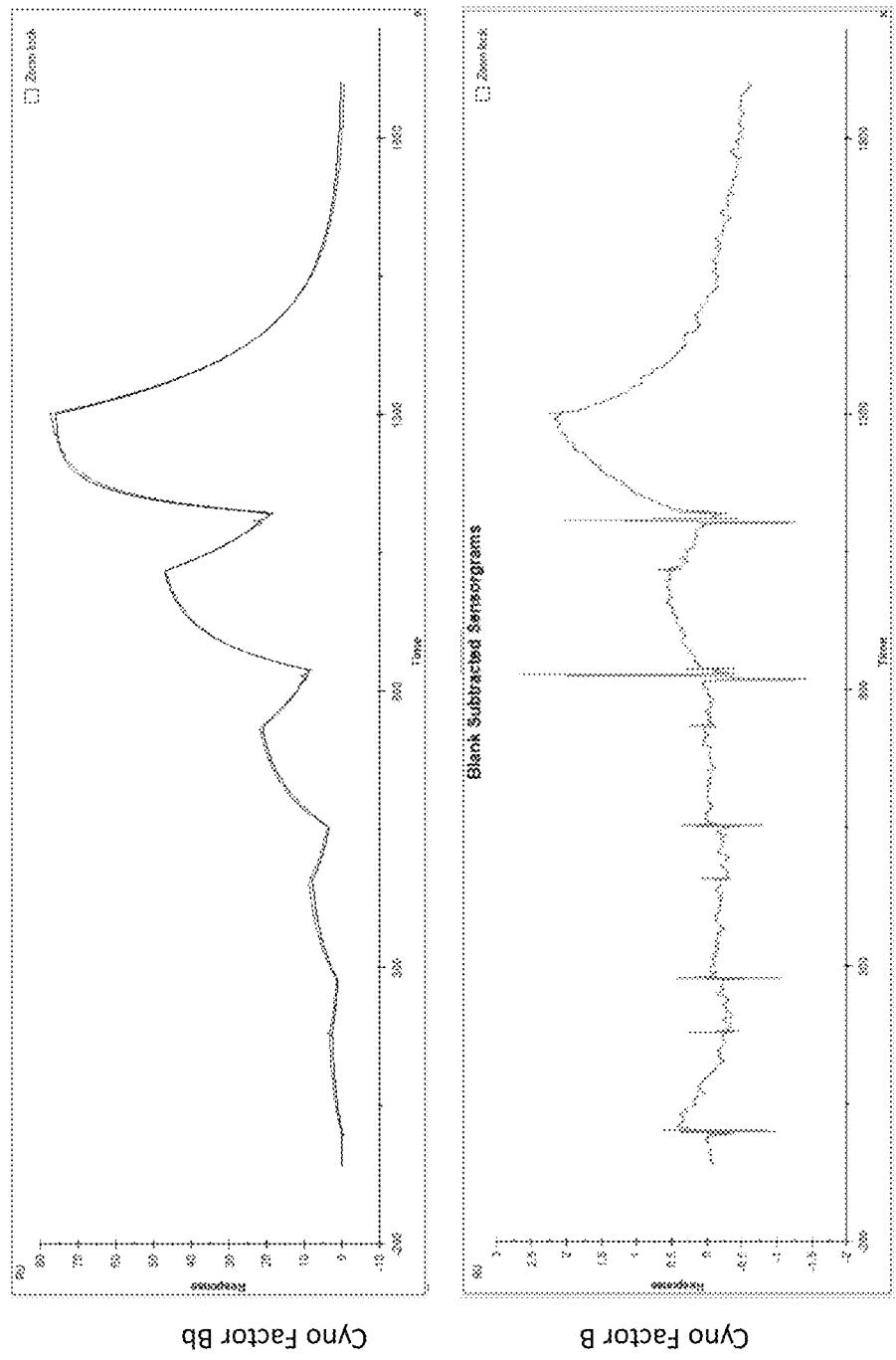

Inhibition of AP-mediated hemolysis by humanized variants in human serum Inhibition of AP pathway-mediated hemolysis was determined using human or cynomolgus monkey serum and rabbit erythrocytes in EGTA-containing buffer to inhibit the classical pathway. A dilution series of the parental antibody and humanized variants starting at 200 µg/mL were incubated with 20% human serum and $10 \times 10^6$ rabbit red blood cells (RBCs) for one hour at 37° C. The amount of lysis was determined by measuring the absorbance of the supernatant at 540 nm and subtracting the background absorbance in control wells containing ethylene diamine tetraacetic acid (EDTA). Results are shown in FIG. 6B. In FIG. 6C, the A540, representing the amount of hemolysis, is shown for each variant at 100 µg/mL. VH4/VK6 and VH6/VK7 show the greatest inhibition of hemolysis as reflected by the largest reduction in A540.

Binding of The Parent Antibody and Humanized Variants to Cynomolgus Monkey Factor Bb To ensure that the humanization process did not affect species cross-reactivity, the parental antibody and humanized derivatives were tested for binding to human and cynomolgus monkey factor Bb by Biolayer Interferometry (BLI) using an Octet Red. Briefly, biotinylated antibodies were loaded onto SA Biosensors equilibrated in PBS, 0.1% BSA, 0.02% Tween-20 (assay buffer). After a 60 second baseline in assay buffer, antibodies were loaded onto the probes for 180 seconds, followed by another 60 second baseline. Association to human (Comptech) or cynomolgus monkey factor Bb (purified in-house) was measured for 300 seconds, followed by a 300 second dissociation. Kinetic parameters were calculated by the Octet Analysis software using a 1:1 binding model. Data are summarized in Table 13 and show that the humanization did not affect cross-reactivity to factor Bb from cynomolgus monkey.

TABLE 13

Binding of Humanized Variants to
Human and Cynomolgus Bb by BLI.

| Antibody | KD (M) for Human Bb | KD (M) for Cyno Bb |
|---|---|---|
| Anti-factor Bb antibody in Table 1 | $1.9 \times 10^{-9}$ | $1.1 \times 10^{-8}$ |
| VH0/Vk0 | $2.0 \times 10^{-9}$ | $1.0 \times 10^{-8}$ |
| VH4/Vk6 | $1.6 \times 10^{-9}$ | $8.6 \times 10^{-9}$ |
| VH4/Vk7 | $1.9 \times 10^{-9}$ | $1.1 \times 10^{-8}$ |
| VH6/Vk6 | $1.9 \times 10^{-9}$ | $1.1 \times 10^{-8}$ |
| VH6/Vk7 | $1.9 \times 10^{-9}$ | $1.1 \times 10^{-8}$ |
| VH7/Vk7 | $2.9 \times 10^{-9}$ | $1.6 \times 10^{-8}$ |

Binding of $V_H4/V_K6$-IgG4v2 and $V_H6/V_K7$-IgG4v2 to human and cynomolgus monkey factor Bb To determine whether the modification of the Fc portion of the antibodies affected affinity and species cross-reactivity, $V_H4/V_K6$-IgG4v2 and $V_H6/V_K7$-IgG4v2 were tested alongside their parental antibodies, $V_H4/V_K6$ and $V_H6/V_K7$, respectively, for their ability to bind human and cynomolgus monkey factor Bb by BLI. VH4/VK6-IgG4v2 and VH6/VK7-IgG4v2 contain mutations in the Fc region that increase the affinity for an Fc receptor. The experiment was carried out as described in the example above and results are summarized in Table 14. As expected, modification of the Fc did not affect binding.

TABLE 14

Binding Humanized Anti-Factor Bb Antibodies
to Human and Cynomolgus Factor Bb by BLI.

| Antibody | KD (M) for Human Bb | KD (M) for Cyno Bb |
|---|---|---|
| $V_A6/V_K6$-IgG4v1 | $1.6 \times 10^{-9}$ | $1.1 \times 10^{-8}$ |
| $V_H4/V_K6$-IgG4v2 | $1.6 \times 10^{-9}$ | $1.1 \times 10^{-8}$ |
| $V_H6/V_K7$-IgG4v1 | $1.7 \times 10^{-9}$ | $1.0 \times 10^{-8}$ |
| $V_H6/V_K7$-IgG4v2 | $1.7 \times 10^{-9}$ | $1.0 \times 10^{-8}$ |

Specificity of $V_H4/V_K6$ and $V_H6/V_K7$ for Factor Bb (the Activated Form of Factor B)

The ability of $V_H4/V_K6$ and $V_H6/V_K7$ to bind to zymogen factor B and factor Bb from both human and cynomolgus monkey was determined by surface plasmon resonance using a BIACORE™ T200. Human factor B and factor Bb were purchased from Comptech and cynomolgus monkey factor B and factor Bb were purified in-house. Briefly, the monoclonal antibodies were captured on a BIACORE™ Series S Protein A chip in HBSP+(10 mM HEPES, 150 mM NaCl, 0.05% P20 pH 7.4) at a flow rate of 30 µL/min. A five-point concentration series of each analyte was tested for binding using single cycle kinetics with a contact time of 180 seconds per concentration followed by a 600 sec dissociation at 25° C. and a flow rate of 60 µL/sec. Both human and cynomolgus monkey factor B started at a concentration of 500 nM followed by 2-fold dilutions, while human and cynomolgus monkey factor Bb started at concentrations of 30 nM and 150 nM, respectively, followed by 2-fold dilutions. Data were analyzed using the BIACORE™ evaluation software using a 1:1 binding model. Sensorgrams are shown in FIGS. 7A-7D. Results are summarized in Table 15. Briefly, both humanized variants show roughly 10-fold higher affinities for human factor Bb compared to cynomolgus monkey factor Bb. Binding to human or cynomolgus monkey factor B was barely detectable and the small signal that was observed was dominated by non-specific binding.

TABLE 15

Specificity of Lead Humanized Variants to Human or Cynomolgus Monkey Factor Bb

| Antibody | Antigen | ka (1/Ms) | kd (1/s) | KD (M) | Rmax (RU) | Chi² (RU²) |
|---|---|---|---|---|---|---|
| $V_H4/V_K6$-IgG4v2 | Human Factor Bb | $4.10 \times 10^5$ | $9.25 \times 10^{-4}$ | $2.26 \times 10^{-9}$ | 108.2 | 0.636 |
| | Human Factor B | n/a | n/a | n/a | n/a | n/a |
| | Cyno Factor Bb | $3.49 \times 10^5$ | $6.83 \times 10^{-3}$ | $1.96 \times 10^{-8}$ | 118.7 | 2.42 |
| | Cyno Factor B | n/a | n/a | n/a | n/a | n/a |
| $V_H6/V_K7$-IgG4v2 | Human Factor Bb | $2.32 \times 10^5$ | $1.38 \times 10^{-3}$ | $5.92 \times 10^{-9}$ | 91.8 | 0.114 |
| | Human Factor B | n/a | n/a | n/a | n/a | n/a |
| | Cyno Factor Bb | $1.55 \times 10^5$ | $8.77 \times 10^{-3}$ | $5.65 \times 10^{-8}$ | 104.6 | 0.457 |
| | Cyno Factor B | n/a | n/a | n/a | n/a | n/a |

Figure 8A:
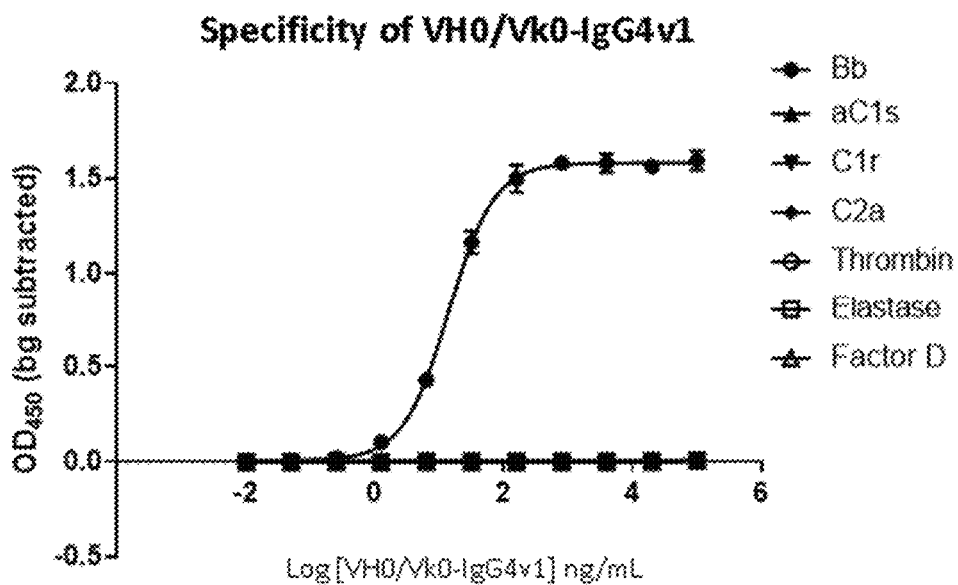
FIGS. 8A-8B show specificity of binding of chimeric parent antibody $V_H0/V_K0$-IgG4v1 (FIG. 8A) and representative humanized variant antibody $V_H6/V_K7$-IgG4v2 (FIG. 8B) to factor Bb only among various complement proteins.
Figure 8B:
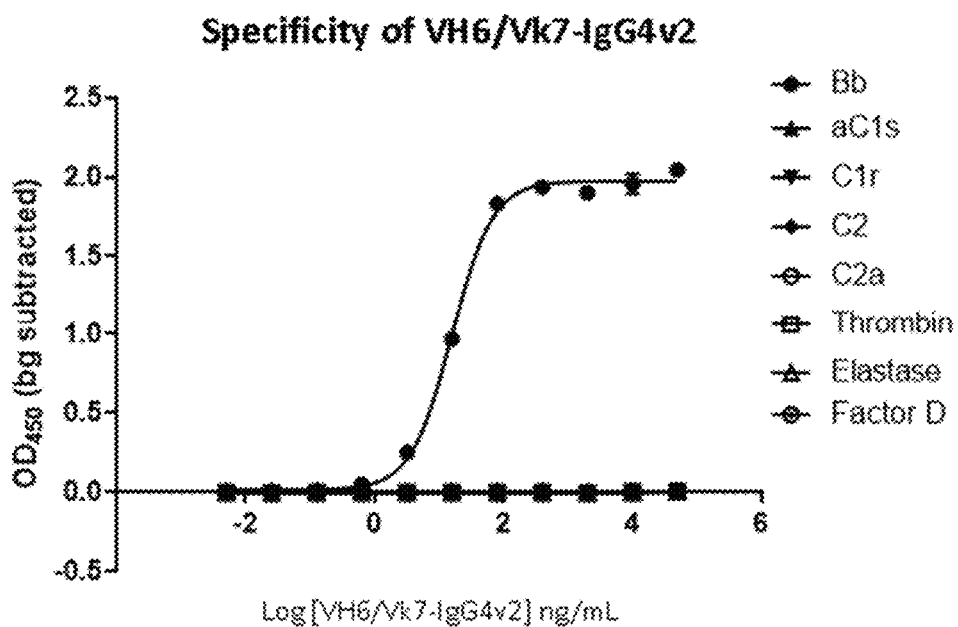

Binding of Chimeric Parent and Representative Humanized Variants to Various Complement Proteins To ensure that humanization did not introduce non-specific binding or cross-reactivity to other complement or plasma proteins, the chimeric parent antibody and a representative humanized variant, $V_H6/V_K7$-IgG4v2, were tested for binding to aC1s (Comptech A104), C1r (Comptech A102), C2 (Comptech A112), C2a (prepared from C2), thrombin (EMD MILLIPORE® 605195), elastase (EMD MILLIPORE® 324682), factor D (Comptech A136), and factor Bb (Comptech A155). Briefly, complement and plasma proteins were coated onto ELISA plates at 2.5 µg/mL in PBS overnight at 4° C. Plates were then blocked with Casein for 1 hour at room temperature and washed four times with 1X DPBS/0.05% Tween-20 followed by a single wash with 1X DPBS. Serial dilutions starting at 50 µg/ml of biotinylated chimeric parent or $V_H6/V_K7$-IgG4v2 were added to the plate in PBS/0.1% casein/0.1% Tween-20 and incubated for 2 hours at room temperature. Plates were washed as described and a 1:10,000 dilution of streptavidin-HRP (Southern Biotech 7100-05) in PBS/0.1% casein/0.1% Tween-20 was added to the plate and incubated for 30 minutes at room temperature. Plates were again washed and Ultra TMP ELISA (Thermo 34028) was added to the plate for 1 minute, followed by stop solution). OD 450 nm was read in a plate reader and background at 620 nm was subtracted. Both the chimeric parent (FIG. 8A) and the humanized variant (FIG. 8B) show complete specificity for factor Bb.

Example 3: $V_H6/V_K7$-IgG4v2 Produced from CHO Versus HEK Behave the Same

To determine whether $V_H6/V_K7$-IgG4v2 produced in HEK cells behaved the same when produced in CHO cells, V$_H$6/V$_K$7-IgG4v2 was generated by transient expression in HEK cells or by stable expression in CHO cells using standard methods.

Figure 9A:
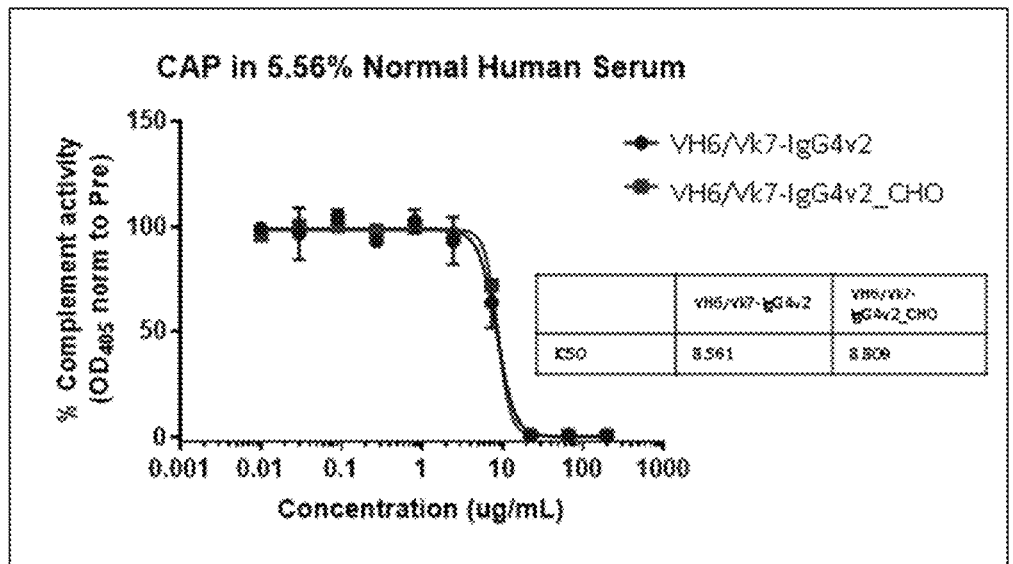
FIGS. 9A-9B show activity of $V_H6/V_K7$-IgG4v2 (produced from HEK cells) and $V_H6/V_K7$-IgG4v2_CHO (produced from CHO cells) in WIESLAB® Complement Alternative Pathway (CAP) assay using normal human (FIG. 9A) and Cyno (FIG. 9B) serum.
Figure 9B:
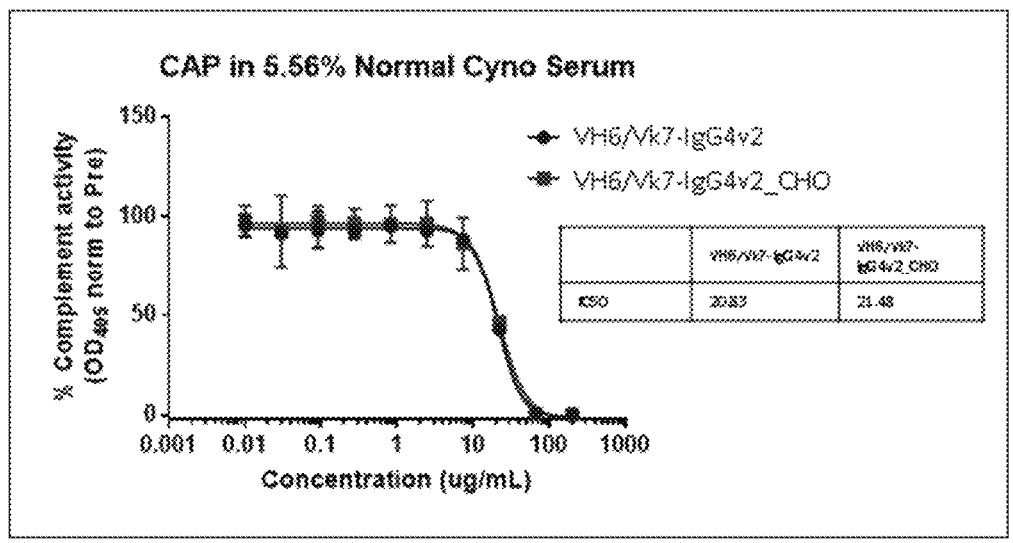
Figure 10A:
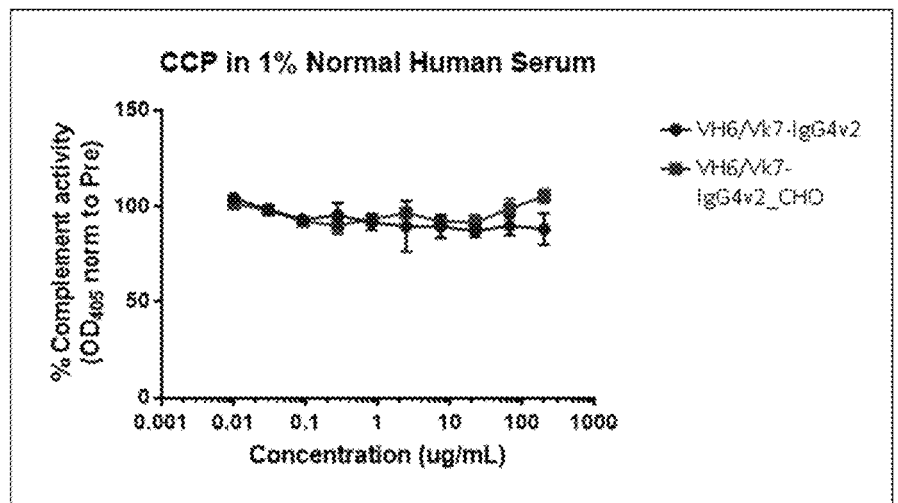
FIGS. 10A-10B show activity of $V_H6/V_K7$-IgG4v2 (produced from HEK) and $V_H6/V_K7$-IgG4v2_CHO in WIESLAB® Complement Classical Pathway (CCP) assay using normal human (FIG. 10A) and Cyno (FIG. 10B) serum.
Figure 10B:
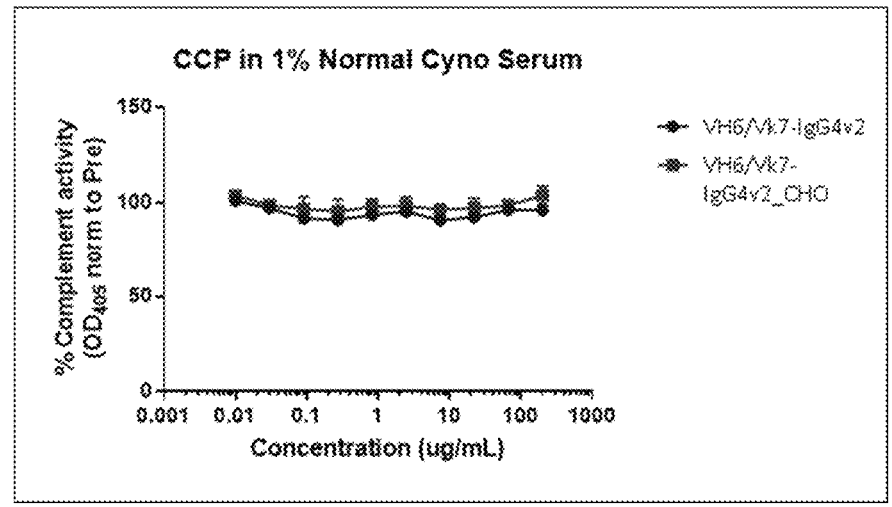
Figure 11:
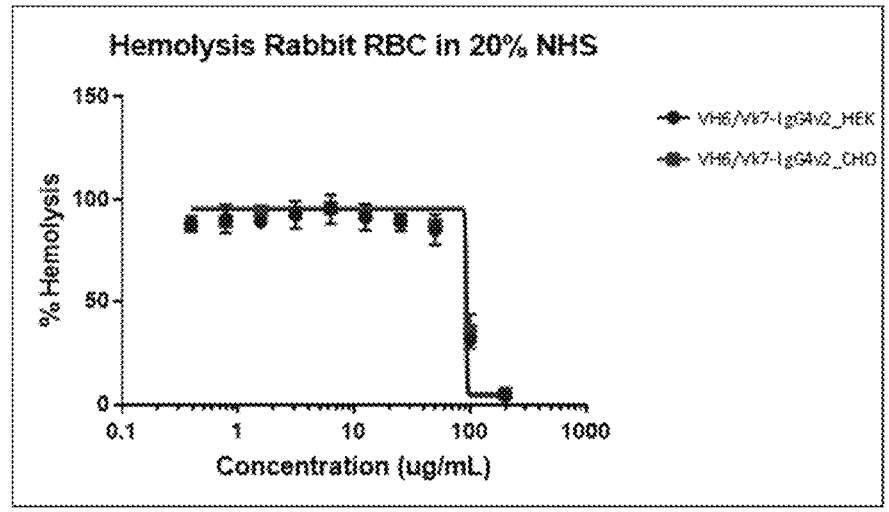
FIG. 11 show hemolysis of Rabbit RBC by $V_H6/V_K7$-IgG4v2_HEK and $V_H6/V_K7$-IgG4v2_CHO in normal human serum.

The complement alternative pathway (CAP) and classical pathway (CCP) activities of the antibodies were determined using the Complement System Alternative Pathway and Classical Pathway WIESLAB® Kits, respectively, in accordance with the manufacturer's instructions. To determine CAP activity, antibodies were tested in 5.56% normal human serum (FIG. 9A) and 5.56% normal cynomolgus monkey serum (FIG. 9B). To determine CCP activity, antibodies were tested in 1% normal human serum (FIG. 10A) and 1% normal cynomolgus monkey serum (FIG. 10B). OD405 nm was measured and results were normalized to serum activity prior to antibody injection. V$_H$6/V$_K$7-IgG4v2 produced in CHO and HEK showed similar activity. IC$_{50}$ values for both sets of antibodies were calculated and are shown in FIGS. 10A-10B. V$_H$6/V1(7-IgG4v2 produced in CHO showed similar potency to V$_H$6/V$_K$7-IgG4v2 produced in HEK. AP pathway-mediated hemolysis of V$_H$6/V$_K$7-IgG4v2 produced in CHO and HEK was also compared. Hemolysis was determined using 20% normal human serum and rabbit erythrocytes in buffer containing EGTA to inhibit the classical pathway. The amount of lysis was determined by measuring the of the supernatant and subtracting the background absorbance in control wells containing ethylene diamine tetraacetic acid (EDTA). V$_H$6/V$_K$7-IgG4v2 produced in CHO and HEK showed similar % hemolysis (FIG. 11).

Figure 12:
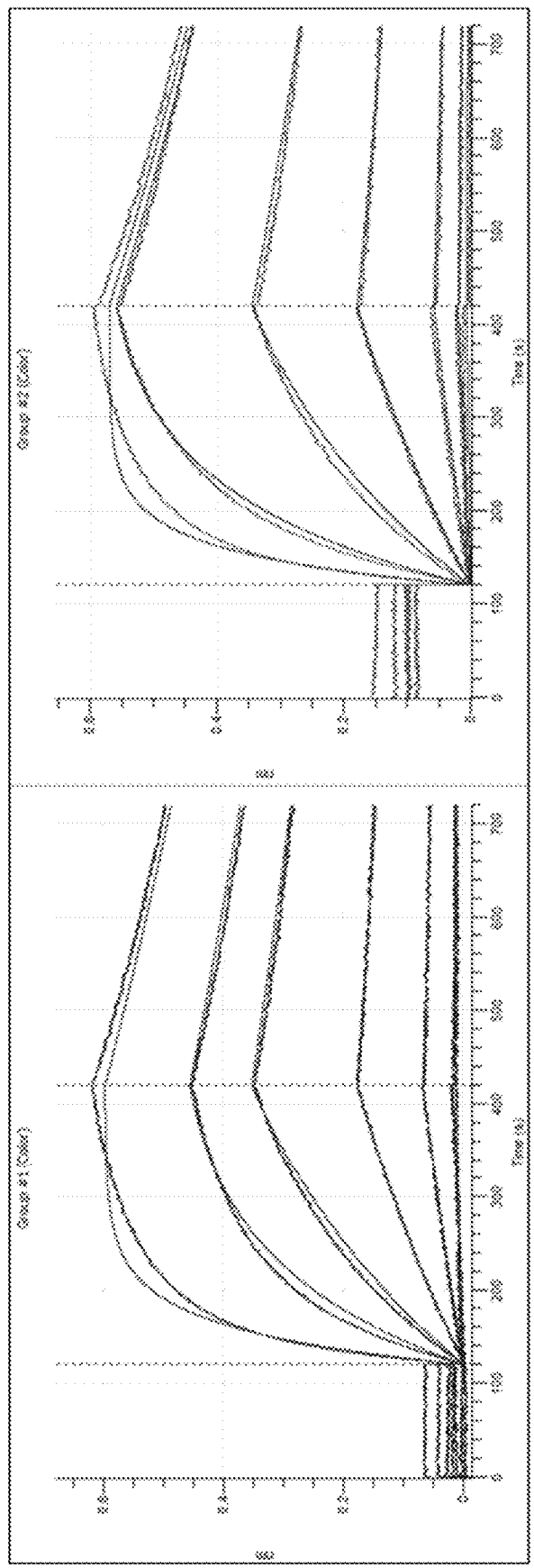
FIG. 12 show affinity and multiple cycle sensorgrams raw data with fitted curves for $V_H6/V_K7$-IgG4v2_CHO(left) and $V_H6/V_K7$-IgG4v2_HEK(right) binding to human Bb protein.

Multicycle kinetic analysis was performed on CHO and HEK-produced V$_H$6/V$_K$7-IgG4v2 antibodies using biolayer interferometry. Antibodies were diluted to 10 μg/mL in PBS+0.02%. Tween20, 0.1% BSA, 0.05% sodium azide and loaded onto anti-hIgG Fc sensors (pre-equilibrated in the same buffer) for 90 seconds followed by a 60-minute baseline in buffer. Binding of a concentration series of human factor Bb (Complement Technologies, #A155), ranging from 100 nM to 0.14 nM in 2-fold dilutions, was measured in a 300 second association in the same buffer, followed by a 300 second dissociation step. The binding curves and fitted data, as well as calculated K$_d$s for both antibodies are shown in FIG. 12.

REFERENCES

Cao et al. (2016) *Haematologica* 101(11): 1319-1326
Chothia et al. (1987) *J. Mol. Biol.* 196:901-917
Bryson et el. (2010). *Biodrugs* 24 (1):1-8
Dall'Acqua et al. (2006) *J Biol Chem* 281: 23514-24
De Vriese et al. (2015) *J Am Soc Nephrol* 26: 2917-2929
Holers (2008) *Immunological Reviews* 223: 300-316
Holt et al. (2003) *Trends Biotechnol.* 21:484
Gold et al. (2006) *Nat. Genet.* 38(4): 458-462
Kabat et al., *J. Biol. Chem.* 252:6609-6616 (1977)
Kabat et al. U. S. Dept. of Health and Human Services, "*Sequences of proteins of immunological interest*" (1991)
Lefranc et al. (2003) *Developmental and Comparative Immunology* 27:55
MacCallum et al. (1996) *J. Mol. Biol.* 262:732-745
Perry et al. (2008) *Drugs R D* 9 (6): 385-396
Schubart et al. (2019) *PNAS* 116(16): 7926-7931
Smith P et al. (2012) *PNAS* 109: 6181-6186
Shields et al. (2001) *J Biol Chem* 276: 6591-604
Shaner et al. (2005) *Nat. Methods* 2:905-909
Thurman (2015) *Am J Kidney Dis* 65(1): 156-168
U.S. Pat. No. 6,737,056
International Publication No. WO 02/060919
International Publication No. WO 98/23289;
International Publication No. WO 97/34631

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

OTHER EMBODIMENTS

In some embodiments, the present disclosure provides:

1. A humanized antibody that binds specifically to human complement factor Bb protein and comprises a heavy chain variable region (V$_H$) comprising the amino acid sequence of SEQ ID NO: 19 and a light chain variable region (V$_L$) comprising the amino acid sequence of SEQ ID NO: 27.

2. A humanized antibody that binds specifically to human complement factor Bb protein and comprises a heavy chain variable region (V$_H$) comprising the amino acid sequence of SEQ ID NO: 17 and a light chain variable region (V$_L$) comprising the amino acid sequence of SEQ ID NO: 26.

3. The humanized antibody of paragraph 1 or paragraph 2, wherein the humanized antibody binds specifically to the human complement factor Bb protein with an affinity of $10^{-6}$ to $10^{-9}$ M.

4. The humanized antibody of any one of paragraphs 1-3, wherein the humanized antibody inhibits a complement pathway activity.

5. The humanized antibody of paragraph 4, wherein the complement activity is selected from the group consisting of: AP-mediated terminal membrane attack complex (MAC) deposition, AP-mediated hemolysis, C3 fragment deposition on red blood cells or other cell types, C3b/Bb-mediated cleavage of C3, and C3bBb3b-mediated cleavage of C5.

6. The humanized antibody of any one of paragraphs 1-5, wherein the humanized antibody is a bispecific antibody or a multispecific antibody.

7. The humanized antibody of any one of paragraphs 1-6, wherein the humanized antibody is selected from the group consisting of an Ig monomer, a Fab fragment, a F(ab')2 fragment, a scFv, a scAb, and a Fv.

8. The humanized antibody of any one of paragraphs 1-6, wherein the humanized antibody comprises a heavy chain constant region of the isotype IgG1, IgG2, IgG3, or IgG4.

9. The humanized antibody of paragraph 8, wherein the humanized antibody comprises an IgG4 constant region or a variant thereof.

10. The humanized antibody of paragraph 9, wherein the heavy chain constant region comprises an amino acid sequence that is at least 90% identical to any one of SEQ ID NOs: 28-30.

11. The humanized antibody of any one of paragraphs 1 and 3-10, wherein the humanized antibody comprises a heavy chain comprising the amino acid sequence of any one of SEQ ID NOs: 32-34 and a light chain comprising the amino acid sequence of SEQ ID NO: 35.

12. The humanized antibody of any one of paragraphs 2-10, wherein the humanized antibody comprises a heavy chain comprising the amino acid sequence of any one of SEQ ID NOs: 36-38 and a light chain comprising the amino acid sequence of SEQ ID NO: 39.

13. A conjugate comprising the humanized antibody of any one of paragraphs 1-12.

14. A pharmaceutical composition comprising the humanized antibody of any one of paragraphs 1-12 or the conjugate of paragraph 13.

15. The pharmaceutical composition of paragraph 14, further comprising a pharmaceutically acceptable excipient.

16. A device comprising the humanized antibody of any one of paragraphs 1-12, the conjugate of paragraph 13, or the pharmaceutical composition of paragraph 14 or paragraph 15.

17. The device of paragraph 16, wherein the device is an injectable device.

18. The device of paragraph 17, wherein the injectable device is a syringe, a pen, or an electronic injection device (e-Device).

19. A method of treating a subject having a complement-mediated disease or disorder, the method comprising: administering to the subject an effective amount of the humanized antibody of any one of paragraphs 1-13, the conjugate of paragraph 14, or the pharmaceutical composition of paragraph 15 or 16 to treat the complement-mediated disease.

20. The method of paragraph 19, wherein the complement-mediated disease is selected from the group consisting of: IgA nephropathy (Berger's disease), atypical hemolytic uremic syndrome (aHUS), paroxysmal nocturnal hemoglobinuria (PNH), idiopathic thrombocytopenic purpura (ITP), thrombotic thrombocytopenic purpura (TTP), lupus nephritis, ANCA vasculitis, membranous nephropathy, C3 glomerulonephritis (C3GN), focal segmental glomerulosclerosis (FSGS), multiple sclerosis, macular degeneration, age-related macular degeneration (AMD), rheumatoid arthritis, antiphospholipid antibody syndrome, asthma, ischemia-reperfusion injury, Type II membrano-proliferative GN, spontaneous fetal loss, Pauci-immune vasculitis, epidermolysis bullosa, recurrent fetal loss, and traumatic brain injury.

21. A method of inhibiting a complement pathway activity in a subject, the method comprising administering to the subject an effective amount of the humanized antibody of any one of paragraphs 1-13, the conjugate of paragraph 14, or the pharmaceutical composition of paragraph 15 or 16 to inhibit the complement activity.

22. The method of paragraph 21, wherein the subject has a complement-mediated disease or disorder.

23. The method of paragraph 22, wherein the complement-mediated disease is selected from the group consisting of: IgA nephropathy (Berger's disease), atypical hemolytic uremic syndrome (aHUS), paroxysmal nocturnal hemoglobinuria (PNH), idiopathic thrombocytopenic purpura (ITP), thrombotic thrombocytopenic purpura (TTP), lupus nephritis, ANCA vasculitis, membranous nephropathy, C3 glomerulonephritis (C3GN), focal segmental glomerulosclerosis (FSGS), multiple sclerosis, macular degeneration, age-related macular degeneration (AMD), rheumatoid arthritis, antiphospholipid antibody syndrome, asthma, ischemia-reperfusion injury, Type II membrano-proliferative GN, spontaneous fetal loss, Pauci-immune vasculitis, epidermolysis bullosa, recurrent fetal loss, and traumatic brain injury.

24. The method of any one of paragraphs 21-23, wherein the complement activity is selected from the group consisting of: AP-mediated terminal membrane attack complex (MAC) deposition, AP-mediated hemolysis, C3 fragment deposition on red blood cells or other cell types, C3b/Bb-mediated cleavage of C3, and C3bBb3b-mediated cleavage of C5.

25. The method of any one of paragraphs 19-24, further comprising administering to the subject a therapeutic agent.

26. The method of any one of paragraphs 19-25, wherein the administering is intravenous, subcutaneous, or intramuscular.

27. A nucleic acid or nucleic acid set encoding or collectively encoding the humanized antibody of any one of paragraphs 1-12.

28. A vector or vector set comprising the nucleic acid or nucleic acid set of paragraph 27.

29. A cell expressing the humanized antibody of any one of paragraphs 1-3, the nucleic acid or nucleic acid set of paragraph 27, or the vector or vector set of paragraph 28.

30. The cell of paragraph 29, wherein the cell is a mammalian cell.

31. The cell of paragraph 30, wherein the mammalian cell is selected from the group consisting of: human embryonic kidney (HEK) cells, Chinese hamster ovary (CHO) cells, NS0 myeloma cells, SP2 cells, COS cells, and mammary epithelial cells.

32. A method of producing the humanized antibody, comprising culturing the cell of any one of paragraphs 29-31 to produce the humanized antibody.

33. The method of paragraph 32, further comprising isolating the humanized antibody.

EQUIVALENTS AND SCOPE

Those skilled in the art will recognize or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean at least one than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which at least one limitation, element, clause, or descriptive term, from at least one of the claims or from at least one relevant portion of the description, is introduced into another claim. For example, a claim that is dependent on another claim can be modified to include at least one of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

In the claims, as well as in the specification above, all transitional phrases such as "comprising," "including," "carrying," "having," "containing," "involving," "holding," "composed of," are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any at least one of the claims. Where ranges are given, any value within the range may explicitly be excluded from any at least one of the claims. Any embodiment, element, feature, application, or aspect of the compositions and/or methods of the disclosure, can be excluded from any at least one claims. For purposes of brevity, all of the embodiments in which at least one elements, features, purposes, or aspects is excluded are not set forth explicitly herein. The terms "about" and "substantially" preceding a numerical value mean±10% of the recited numerical value.

What is claimed is:

1. A nucleic acid or nucleic acid set encoding a humanized antibody that binds specifically to human complement factor Bb protein, wherein the humanized antibody comprises: a heavy chain variable region (VH) comprising the amino acid sequence of SEQ ID NO: 19 and a light chain variable region (VL) comprising the amino acid sequence of SEQ ID NO: 27.

2. A vector or vector set comprising the nucleic acid or nucleic acid set of claim 1.

3. An isolated cell comprising the nucleic acid or nucleic acid set of claim 1.

4. The isolated cell of claim 3, wherein the cell is a mammalian cell.

5. The isolated cell of claim 4, wherein the mammalian cell is selected from human embryonic kidney (HEK) cells, Chinese hamster ovary (CHO) cells, NS0 myeloma cells, SP2 cells, COS cells, and mammary epithelial cells.

6. The nucleic acid or nucleic acid set of claim 1, wherein the humanized antibody comprises a heavy chain constant region comprising the amino acid sequence of any one of SEQ ID NOsi[H] 28-30.

7. The nucleic acid or nucleic acid set of claim 1, wherein the humanized antibody comprises a light chain constant region comprising the amino acid sequence of SEQ ID NO: 31.

8. The nucleic acid or nucleic acid set of claim 6, wherein the humanized antibody comprises a heavy chain comprising the amino acid sequence of SEQ ID NO: 32 and a light chain comprising the amino acid sequence of SEQ ID NO: 35.

9. The nucleic acid or nucleic acid set of claim 6, wherein the humanized antibody comprises a heavy chain comprising the amino acid sequence of SEQ ID NO: 33 and a light chain comprising the amino acid sequence of SEQ ID NO: 35.

10. The nucleic acid or nucleic acid set of claim 6, wherein the humanized antibody comprises a heavy chain comprising the amino acid sequence of SEQ ID NO: 34 and a light chain comprising the amino acid sequence of SEQ ID NO: 35.

11. The nucleic acid or nucleic acid set of claim 1, wherein the humanized antibody is selected from the group consisting of an Ig monomer, a Fab fragment, a F(ab')2 fragment, a scFv, a scAb, and a Fv.

12. The nucleic acid or nucleic acid set of claim 1, wherein the humanized antibody comprises a heavy chain constant region of the isotype IgG1, IgG2, IgG3, or IgG4.

13. A method of producing a humanized antibody that binds specifically to human complement factor Bb protein, the method comprising culturing the isolated cell of claim 3 to produce the humanized antibody.

14. The method of claim 13, further comprising isolating the humanized antibody.

15. A composition comprising: a nucleic acid or nucleic acid set encoding a humanized antibody that binds specifically to human complement factor Bb protein, wherein the humanized antibody comprises: a heavy chain variable region (VH) comprising the amino acid sequence of SEQ ID NO: 19 and a light chain variable region (VL) comprising the amino acid sequence of SEQ ID NO: 27, and a buffer.

16. A composition comprising: a vector or vector set comprising a nucleic acid or nucleic acid set encoding a humanized antibody that binds specifically to human complement factor Bb protein, wherein the humanized antibody comprises: a heavy chain variable region (VH) comprising the amino acid sequence of SEQ ID NO: 19 and a light chain variable region (VL) comprising the amino acid sequence of SEQ ID NO: 27, and a buffer.

17. A composition comprising: an isolated cell comprising a nucleic acid or nucleic acid set encoding a humanized antibody that binds specifically to human complement factor Bb protein, wherein the humanized antibody comprises: a heavy chain variable region (VH) comprising the amino acid sequence of SEQ ID NO: 19 and a light chain variable region (VL) comprising the amino acid sequence of SEQ ID NO: 27, and a buffer.

\* \* \* \* \*

SEQUENCE LISTING

```
<160> NUMBER OF SEQ ID NOS: 66

<210> SEQ ID NO 1
<211> LENGTH: 5
<212> TYPE: PRT
<213> ORGANISM: Mus musculus

<400> SEQUENCE: 1

Asn Tyr Ala Met Ser
1               5

<210> SEQ ID NO 2
<211> LENGTH: 17
<212> TYPE: PRT
<213> ORGANISM: Mus musculus

<400> SEQUENCE: 2

Thr Ile Ser Asn Arg Gly Ser Tyr Thr Tyr Tyr Pro Asp Ser Val Lys
1               5                   10                  15

Gly

<210> SEQ ID NO 3
<211> LENGTH: 6
<212> TYPE: PRT
<213> ORGANISM: Mus musculus

<400> SEQUENCE: 3

Glu Arg Pro Met Asp Tyr
1               5

<210> SEQ ID NO 4
<211> LENGTH: 11
<212> TYPE: PRT
<213> ORGANISM: Mus musculus
```

<400> SEQUENCE: 4

Lys Ala Ser Gln Asp Val Gly Thr Ala Val Ala
1               5                   10

<210> SEQ ID NO 5
<211> LENGTH: 7
<212> TYPE: PRT
<213> ORGANISM: Mus musculus

<400> SEQUENCE: 5

Trp Ala Ser Thr Arg His Thr
1               5

<210> SEQ ID NO 6
<211> LENGTH: 9
<212> TYPE: PRT
<213> ORGANISM: Mus musculus

<400> SEQUENCE: 6

His Gln His Ser Ser Asn Pro Leu Thr
1               5

<210> SEQ ID NO 7
<211> LENGTH: 8
<212> TYPE: PRT
<213> ORGANISM: Mus musculus

<400> SEQUENCE: 7

Gly Phe Thr Phe Ser Asn Tyr Ala
1               5

<210> SEQ ID NO 8
<211> LENGTH: 8
<212> TYPE: PRT
<213> ORGANISM: Mus musculus

<400> SEQUENCE: 8

Ile Ser Asn Arg Gly Ser Tyr Thr
1               5

<210> SEQ ID NO 9
<211> LENGTH: 8
<212> TYPE: PRT
<213> ORGANISM: Mus musculus

<400> SEQUENCE: 9

Ala Arg Glu Arg Pro Met Asp Tyr
1               5

<210> SEQ ID NO 10
<211> LENGTH: 6
<212> TYPE: PRT
<213> ORGANISM: Mus musculus

<400> SEQUENCE: 10

Gln Asp Val Gly Thr Ala
1               5

<210> SEQ ID NO 11
<211> LENGTH: 3
<212> TYPE: PRT
<213> ORGANISM: Mus musculus

<400> SEQUENCE: 11

Trp Ala Ser
1

<210> SEQ ID NO 12
<211> LENGTH: 115
<212> TYPE: PRT
<213> ORGANISM: Mus musculus

<400> SEQUENCE: 12

Glu Val Gln Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Asn Arg Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Glu Arg Pro Met Asp Tyr Trp Gly Gln Gly Thr Ser Val Thr
            100                 105                 110

Val Ser Ser
        115

<210> SEQ ID NO 13
<211> LENGTH: 107
<212> TYPE: PRT
<213> ORGANISM: Mus musculus

<400> SEQUENCE: 13

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Val Tyr Phe Cys His Gln His Ser Ser Asn Pro Leu
                85                  90                  95

Thr Phe Gly Ala Gly Thr Lys Leu Glu Leu Lys
            100                 105

<210> SEQ ID NO 14
<211> LENGTH: 115
<212> TYPE: PRT
<213> ORGANISM: Artificial Sequence
<220> FEATURE:
<223> OTHER INFORMATION: Synthetic

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

```
Ala Met Ser Trp Val Arg Gln Ala Pro Gly Lys Gly Leu Glu Trp Val
            35                  40                  45

Ala Thr Ile Ser Asn Arg Gly Ser Tyr Thr Tyr Tyr Pro Asp Ser Val
        50                  55                  60

Lys Gly Arg Phe Thr Ile Ser Arg Asp Asn Ala Lys Asn Ser Leu Tyr
 65                  70                  75                  80

Leu Gln Met Ser Ser Leu Arg Ser Glu Asp Thr Ala Leu Tyr Tyr Cys
                85                  90                  95

Ala Arg Glu Arg Pro Met Asp Tyr Trp Gly Gln Gly Thr Ser Val Thr
            100                 105                 110

Val Ser Ser
        115

<210> SEQ ID NO 15
<211> LENGTH: 115
<212> TYPE: PRT
<213> ORGANISM: Artificial Sequence
<220> FEATURE:
<223> OTHER INFORMATION: Synthetic

<400> SEQUENCE: 15

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
            35                  40                  45

Ala Thr Ile Ser Asn Arg Gly Ser Tyr Thr Tyr Tyr Pro Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Arg Glu Arg Pro Met Asp Tyr Trp Gly Gln Gly Thr Leu Val Thr
            100                 105                 110

Val Ser Ser
        115

<210> SEQ ID NO 16
<211> LENGTH: 115
<212> TYPE: PRT
<213> ORGANISM: Artificial Sequence
<220> FEATURE:
<223> OTHER INFORMATION: Synthetic

<400> SEQUENCE: 16

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
            35                  40                  45

Ala Thr Ile Ser Asn Arg Gly Ser Tyr Thr Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
```

85                  90                  95

Ala Arg Glu Arg Pro Met Asp Tyr Trp Gly Gln Gly Thr Leu Val Thr
                100                 105                 110

Val Ser Ser
        115

<210> SEQ ID NO 17
<211> LENGTH: 115
<212> TYPE: PRT
<213> ORGANISM: Artificial Sequence
<220> FEATURE:
<223> OTHER INFORMATION: Synthetic

<400> SEQUENCE: 17

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Arg Leu Glu Trp Val
        35                  40                  45

Ala Thr Ile Ser Asn Arg Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ser Glu Asp Thr Ala Leu Tyr Tyr Cys
                85                  90                  95

Ala Arg Glu Arg Pro Met Asp Tyr Trp Gly Gln Gly Thr Ser Val Thr
                100                 105                 110

Val Ser Ser
        115

<210> SEQ ID NO 18
<211> LENGTH: 115
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Asn Arg Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ser Glu Asp Thr Ala Leu Tyr Tyr Cys
                85                  90                  95

Ala Arg Glu Arg Pro Met Asp Tyr Trp Gly Gln Gly Thr Ser Val Thr
                100                 105                 110

Val Ser Ser
        115

<210> SEQ ID NO 19
<211> LENGTH: 115

<212> TYPE: PRT
<213> ORGANISM: Artificial Sequence
<220> FEATURE:
<223> OTHER INFORMATION: Synthetic

<400> SEQUENCE: 19

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Arg Leu Glu Trp Val
        35                  40                  45

Ala Thr Ile Ser Asn Arg Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Glu Arg Pro Met Asp Tyr Trp Gly Gln Gly Thr Leu Val Thr
            100                 105                 110

Val Ser Ser
        115
```

<210> SEQ ID NO 20
<211> LENGTH: 115
<212> TYPE: PRT
<213> ORGANISM: Artificial Sequence
<220> FEATURE:
<223> OTHER INFORMATION: Synthetic

<400> SEQUENCE: 20

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Asn Arg Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Glu Arg Pro Met Asp Tyr Trp Gly Gln Gly Thr Leu Val Thr
            100                 105                 110

Val Ser Ser
        115
```

<210> SEQ ID NO 21
<211> LENGTH: 107
<212> TYPE: PRT
<213> ORGANISM: Artificial Sequence
<220> FEATURE:
<223> OTHER INFORMATION: Synthetic

<400> SEQUENCE: 21

```
Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
```

```
                    20                  25                  30

Val Ala Trp Tyr Gln Gln Lys Pro Gly Gln Pro Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Ser Ser Leu Gln Ser
65                  70                  75                  80

Glu Asp Phe Ala Val Tyr Phe Cys His Gln His Ser Ser Asn Pro Leu
                85                  90                  95

Thr Phe Gly Gln Gly Thr Lys Leu Glu Ile Lys
                100                 105

<210> SEQ ID NO 22
<211> LENGTH: 107
<212> TYPE: PRT
<213> ORGANISM: Artificial Sequence
<220> FEATURE:
<223> OTHER INFORMATION: Synthetic

<400> SEQUENCE: 22

Asp Ile Val Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
                20                  25                  30

Val Ala Trp Tyr Gln Gln Lys Pro Gly Gln Pro Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Ser Ser Leu Gln Ala
65                  70                  75                  80

Glu Asp Phe Ala Val Tyr Phe Cys His Gln His Ser Ser Asn Pro Leu
                85                  90                  95

Thr Phe Gly Gln Gly Thr Lys Leu Glu Ile Lys
                100                 105

<210> SEQ ID NO 23
<211> LENGTH: 107
<212> TYPE: PRT
<213> ORGANISM: Artificial Sequence
<220> FEATURE:
<223> OTHER INFORMATION: Synthetic

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
                20                  25                  30

Val Ala Trp Tyr Gln Gln Lys Pro Gly Gln Pro Pro Lys Leu Leu Ile
            35                  40                  45

Tyr Trp Ala Ser Thr Arg His Thr Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Phe Ala Val Tyr Phe Cys His Gln His Ser Ser Asn Pro Leu
                85                  90                  95

Thr Phe Gly Gln Gly Thr Lys Leu Glu Ile Lys
                100                 105
```

<210> SEQ ID NO 24
<211> LENGTH: 107
<212> TYPE: PRT
<213> ORGANISM: Artificial Sequence
<220> FEATURE:
<223> OTHER INFORMATION: Synthetic

<400> SEQUENCE: 24

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asp Val Gly Thr Ala
            20                  25                  30

Val Ala Trp Tyr Gln Gln Lys Pro Gly Gln Pro Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Phe Ala Val Tyr Tyr Cys His Gln His Ser Ser Asn Pro Leu
                85                  90                  95

Thr Phe Gly Gln Gly Thr Lys Leu Glu Ile Lys
            100                 105
```

<210> SEQ ID NO 25
<211> LENGTH: 107
<212> TYPE: PRT
<213> ORGANISM: Artificial Sequence
<220> FEATURE:
<223> OTHER INFORMATION: Synthetic

<400> SEQUENCE: 25

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asp Val Gly Thr Ala
            20                  25                  30

Val Ala Trp Tyr Gln Gln Lys Pro Gly Gln Pro Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Phe Ala Thr Tyr Tyr Cys His Gln His Ser Ser Asn Pro Leu
                85                  90                  95

Thr Phe Gly Gln Gly Thr Lys Leu Glu Ile Lys
            100                 105
```

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

```
Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
```

```
                35                  40                  45
Tyr Trp Ala Ser Thr Arg His Thr Gly Val Pro Asp Arg Phe Thr Gly
    50                  55                  60
Ser Gly Ser Gly Thr Asp Phe Thr Leu Thr Ile Ser Ser Leu Gln Ser
65                  70                  75                  80
Glu Asp Phe Ala Val Tyr Phe Cys His Gln His Ser Ser Asn Pro Leu
                85                  90                  95
Thr Phe Gly Gln Gly Thr Lys Leu Glu Ile Lys
            100                 105

<210> SEQ ID NO 27
<211> LENGTH: 107
<212> TYPE: PRT
<213> ORGANISM: Artificial Sequence
<220> FEATURE:
<223> OTHER INFORMATION: Synthetic

<400> SEQUENCE: 27

Asp Ile Gln Met Thr Gln Ser Pro Ser Thr Leu Ser Ala Ser Val Gly
1               5                   10                  15
Asp Arg Val Thr Ile Thr Cys Lys Ala Ser Gln Asp Val Gly Thr Ala
            20                  25                  30
Val Ala Trp Tyr Gln Gln Lys Pro Gly Lys Ala Pro Lys Leu Leu Ile
        35                  40                  45
Tyr Trp Ala Ser Thr Arg His Thr Gly Val Pro Asp Arg Phe Ser Gly
    50                  55                  60
Ser Gly Ser Gly Thr Asp Phe Thr Leu Thr Ile Ser Ser Leu Gln Ala
65                  70                  75                  80
Glu Asp Phe Ala Val Tyr Phe Cys His Gln His Ser Ser Asn Pro Leu
                85                  90                  95
Thr Phe Gly Gln Gly Thr Lys Leu Glu Ile Lys
            100                 105

<210> SEQ ID NO 28
<211> LENGTH: 327
<212> TYPE: PRT
<213> ORGANISM: Artificial Sequence
<220> FEATURE:
<223> OTHER INFORMATION: Synthetic

<400> SEQUENCE: 28

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
```

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 29
<211> LENGTH: 327
<212> TYPE: PRT
<213> ORGANISM: Artificial Sequence
<220> FEATURE:
<223> OTHER INFORMATION: Synthetic

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

```
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Gln Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 30
<211> LENGTH: 327
<212> TYPE: PRT
<213> ORGANISM: Artificial Sequence
<220> FEATURE:
<223> OTHER INFORMATION: Synthetic

<400> SEQUENCE: 30

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Glu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Leu His Glu Ala Leu His Ser His Tyr Thr Gln Lys Ser
305                 310                 315                 320

Leu Ser Leu Ser Leu Gly Lys
                325

<210> SEQ ID NO 31
<211> LENGTH: 107
<212> TYPE: PRT
<213> ORGANISM: Artificial Sequence
<220> FEATURE:
<223> OTHER INFORMATION: Synthetic

<400> SEQUENCE: 31

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 32
<211> LENGTH: 442
<212> TYPE: PRT
<213> ORGANISM: Artificial Sequence
<220> FEATURE:
<223> OTHER INFORMATION: Synthetic

<400> SEQUENCE: 32

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Arg Leu Glu Trp Val
        35                  40                  45

Ala Thr Ile Ser Asn Arg Gly Ser Tyr Thr Tyr Tyr Pro Asp Ser Val
    50                  55                  60
```

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Arg Glu Arg Pro Met Asp Tyr Trp Gly Gln Gly Thr Leu Val Thr
        100                 105                 110

Val Ser Ser Ala Ser Thr Lys Gly Pro Ser Val Phe Pro Leu Ala Pro
    115                 120                 125

Cys Ser Arg Ser Thr Ser Glu Ser Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Ser Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 33
<211> LENGTH: 442
<212> TYPE: PRT
<213> ORGANISM: Artificial Sequence
<220> FEATURE:

<223> OTHER INFORMATION: Synthetic

<400> SEQUENCE: 33

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Arg Leu Glu Trp Val
        35                  40                  45

Ala Thr Ile Ser Asn Arg Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Glu Arg Pro Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Glu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 34
<211> LENGTH: 442
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Arg Leu Glu Trp Val
        35                  40                  45

Ala Thr Ile Ser Asn Arg Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Glu Arg Pro Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Glu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

```
Lys Gly Leu Pro Ser Ser Ile Glu Lys Thr Ile Ser Lys Ala Lys Gly
            325                 330                 335

Gln Pro Arg Glu Pro Gln Val Tyr Thr Leu Pro Pro Ser Gln Glu Glu
        340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
            405                 410                 415

Val Phe Ser Cys Ser Val Leu His Glu Ala Leu His Ser His Tyr Thr
        420                 425                 430

Gln Lys Ser Leu Ser Leu Ser Leu Gly Lys
        435                 440
```

<210> SEQ ID NO 35
<211> LENGTH: 214
<212> TYPE: PRT
<213> ORGANISM: Artificial Sequence
<220> FEATURE:
<223> OTHER INFORMATION: Synthetic

<400> SEQUENCE: 35

```
Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Phe Ala Val Tyr Phe Cys His Gln His Ser Ser Asn Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 36
<211> LENGTH: 442

<212> TYPE: PRT
<213> ORGANISM: Artificial Sequence
<220> FEATURE:
<223> OTHER INFORMATION: Synthetic

<400> SEQUENCE: 36

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Arg Leu Glu Trp Val
        35                  40                  45

Ala Thr Ile Ser Asn Arg Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ser Glu Asp Thr Ala Leu Tyr Tyr Cys
                85                  90                  95

Ala Arg Glu Arg Pro Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Ser Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380
```

```
Asn Tyr Lys Thr Thr Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 37
<211> LENGTH: 442
<212> TYPE: PRT
<213> ORGANISM: Artificial Sequence
<220> FEATURE:
<223> OTHER INFORMATION: Synthetic

<400> SEQUENCE: 37

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Arg Leu Glu Trp Val
        35                  40                  45

Ala Thr Ile Ser Asn Arg Gly Ser Tyr Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ser Glu Asp Thr Ala Leu Tyr Tyr Cys
                85                  90                  95

Ala Arg Glu Arg Pro Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
210                 215                 220

Pro Ala Pro Glu Phe Glu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
290                 295                 300
```

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
            325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
            405                 410                 415

Val Phe Ser Cys Ser Val Met His Glu Ala Leu His Asn His Tyr Thr
            420                 425                 430

Gln Lys Ser Leu Ser Leu Ser Leu Gly Lys
            435                 440

<210> SEQ ID NO 38
<211> LENGTH: 442
<212> TYPE: PRT
<213> ORGANISM: Artificial Sequence
<220> FEATURE:
<223> OTHER INFORMATION: Synthetic

<400> SEQUENCE: 38

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Arg Leu Glu Trp Val
        35                  40                  45

Ala Thr Ile Ser Asn Arg Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ser Glu Asp Thr Ala Leu Tyr Tyr Cys
                85                  90                  95

Ala Arg Glu Arg Pro Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Glu Gly Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser Gln Glu Asp Pro Glu Val Gln Phe Asn Trp
        260                 265                 270

Tyr Val Asp Gly Val Glu Val His Asn Ala Lys Thr Lys Pro Arg Glu
    275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
            325                 330                 335

Gln Pro Arg Glu Pro Gln Val Tyr Thr Leu Pro Pro Ser Gln Glu Glu
        340                 345                 350

Met Thr Lys Asn Gln Val Ser Leu Thr Cys Leu Val Lys Gly Phe Tyr
    355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
            405                 410                 415

Val Phe Ser Cys Ser Val Leu His Glu Ala Leu His Ser His Tyr Thr
        420                 425                 430

Gln Lys Ser Leu Ser Leu Ser Leu Gly Lys
    435                 440

<210> SEQ ID NO 39
<211> LENGTH: 214
<212> TYPE: PRT
<213> ORGANISM: Artificial Sequence
<220> FEATURE:
<223> OTHER INFORMATION: Synthetic

<400> SEQUENCE: 39

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Phe Cys His Gln His Ser Ser Asn Pro Leu
            85                  90                  95

Thr Phe Gly Gln Gly Thr Lys Leu Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
    130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 40
<211> LENGTH: 505
<212> TYPE: PRT
<213> ORGANISM: Homo sapiens

<400> SEQUENCE: 40

Lys Ile Val Leu Asp Pro Ser Gly Ser Met Asn Ile Tyr Leu Val Leu
1               5                   10                  15

Asp Gly Ser Asp Ser Ile Gly Ala Ser Asn Phe Thr Gly Ala Lys Lys
            20                  25                  30

Cys Leu Val Asn Leu Ile Glu Lys Val Ala Ser Tyr Gly Val Lys Pro
            35                  40                  45

Arg Tyr Gly Leu Val Thr Tyr Ala Thr Tyr Pro Lys Ile Trp Val Lys
50                  55                  60

Val Ser Glu Ala Asp Ser Ser Asn Ala Asp Trp Val Thr Lys Gln Leu
65                  70                  75                  80

Asn Glu Ile Asn Tyr Glu Asp His Lys Leu Lys Ser Gly Thr Asn Thr
                85                  90                  95

Lys Lys Ala Leu Gln Ala Val Tyr Ser Met Met Ser Trp Pro Asp Asp
            100                 105                 110

Val Pro Pro Glu Gly Trp Asn Arg Thr Arg His Val Ile Ile Leu Met
            115                 120                 125

Thr Asp Gly Leu His Asn Met Gly Gly Asp Pro Ile Thr Val Ile Asp
130                 135                 140

Glu Ile Arg Asp Leu Leu Tyr Ile Gly Lys Asp Arg Lys Asn Pro Arg
145                 150                 155                 160

Glu Asp Tyr Leu Asp Val Tyr Val Phe Gly Val Gly Pro Leu Val Asn
                165                 170                 175

Gln Val Asn Ile Asn Ala Leu Ala Ser Lys Lys Asp Asn Glu Gln His
            180                 185                 190

Val Phe Lys Val Lys Asp Met Glu Asn Leu Glu Asp Val Phe Tyr Gln
            195                 200                 205

Met Ile Asp Glu Ser Gln Ser Leu Ser Leu Cys Gly Met Val Trp Glu
210                 215                 220

His Arg Lys Gly Thr Asp Tyr His Lys Gln Pro Trp Gln Ala Lys Ile
225                 230                 235                 240

Ser Val Ile Arg Pro Ser Lys Gly His Glu Ser Cys Met Gly Ala Val
                245                 250                 255

Val Ser Glu Tyr Phe Val Leu Thr Ala Ala His Cys Phe Thr Val Asp
            260                 265                 270

Asp Lys Glu His Ser Ile Lys Val Ser Val Gly Gly Glu Lys Arg Asp
            275                 280                 285

Leu Glu Ile Glu Val Val Leu Phe His Pro Asn Tyr Asn Ile Asn Gly
            290                 295                 300
```

Lys Lys Glu Ala Gly Ile Pro Glu Phe Tyr Asp Tyr Asp Val Ala Leu
305                 310                 315                 320

Ile Lys Leu Lys Asn Lys Leu Lys Tyr Gly Gln Thr Ile Arg Pro Ile
                325                 330                 335

Cys Leu Pro Cys Thr Glu Gly Thr Thr Arg Ala Leu Arg Leu Pro Pro
            340                 345                 350

Thr Thr Thr Cys Gln Gln Gln Lys Glu Glu Leu Leu Pro Ala Gln Asp
        355                 360                 365

Ile Lys Ala Leu Phe Val Ser Glu Glu Lys Lys Leu Thr Arg Lys
    370                 375                 380

Glu Val Tyr Ile Lys Asn Gly Asp Lys Gly Ser Cys Glu Arg Asp
385                 390                 395                 400

Ala Gln Tyr Ala Pro Gly Tyr Asp Lys Val Lys Asp Ile Ser Glu Val
                405                 410                 415

Val Thr Pro Arg Phe Leu Cys Thr Gly Gly Val Ser Pro Tyr Ala Asp
            420                 425                 430

Pro Asn Thr Cys Arg Gly Asp Ser Gly Gly Pro Leu Ile Val His Lys
        435                 440                 445

Arg Ser Arg Phe Ile Gln Val Gly Val Ile Ser Trp Gly Val Val Asp
    450                 455                 460

Val Cys Lys Asn Gln Lys Arg Gln Lys Gln Val Pro Ala His Ala Arg
465                 470                 475                 480

Asp Phe His Ile Asn Leu Phe Gln Val Leu Pro Trp Leu Lys Glu Lys
                485                 490                 495

Leu Gln Asp Glu Asp Leu Gly Phe Leu
                500             505

<210> SEQ ID NO 41
<211> LENGTH: 345
<212> TYPE: DNA
<213> ORGANISM: Artificial Sequence
<220> FEATURE:
<223> OTHER INFORMATION: Synthetic

<400> SEQUENCE: 41
gaggtgcagc tggtggagtc tgggggaggc ctggtcaagc ctgggggtc cctgagactc      60 tcctgtgcag cctctggatt caccttcagt aactatgcca tgtcttgggt ccgccaggct    120
ccagggaagg gctggagtg gtcgcaacc attagtaatc gtggtagtta cacctactac    180
ccagactcag tgaagggccg attcaccatc tccagagaca acgccaagaa ctcactgtat    240
ctgcaaatga gcagcctgag atctgaggac acggctttgt attactgtgc gagagagagg    300
cctatggact actggggcca aggaacctca gtcaccgtct cctca                     345

<210> SEQ ID NO 42
<211> LENGTH: 345
<212> TYPE: DNA
<213> ORGANISM: Artificial Sequence
<220> FEATURE:
<223> OTHER INFORMATION: Synthetic

<400> SEQUENCE: 42
gaggtgcagc tggtggagtc tgggggaggc ctggtcaagc ctgggggtc cctgagactc      60 tcctgtgcag cctctggatt caccttcagt aactatgcca tgtcttgggt ccgccaggct    120
ccagggaagg gctggagtg gtcgcaacc attagtaatc gtggtagtta cacctactac    180
ccagactcag tgaagggccg attcaccatc tccagagaca acgccaagaa ctcactgtat    240

```
ctgcaaatga acagcctgag agccgaggac acggctttgt attactgtgc gagagagagg    300
cctatggact actggggcca aggaaccctg gtcaccgtct cctca                   345
```

<210> SEQ ID NO 43
<211> LENGTH: 345
<212> TYPE: DNA
<213> ORGANISM: Artificial Sequence
<220> FEATURE:
<223> OTHER INFORMATION: Synthetic

<400> SEQUENCE: 43

```
gaggtgcagc tggtggagtc tgggggaggc ctggtcaagc ctgggggtc  cctgagactc    60 tcctgtgcag cctctggatt caccttcagt aactatgcca tgtcttgggt ccgccaggct   120
ccagggaagg gctggagtg gtcgcaacc attagtaatc gtggtagtta cacctactac    180
gcagactcag tgaagggccg attcaccatc tccagagaca acgccaagaa ctcactgtat   240
ctgcaaatga acagcctgag agccgaggac acggctttgt attactgtgc gagagagagg   300
cctatggact actggggcca aggaaccctg gtcaccgtct cctca                   345
```

<210> SEQ ID NO 44
<211> LENGTH: 345
<212> TYPE: DNA
<213> ORGANISM: Artificial Sequence
<220> FEATURE:
<223> OTHER INFORMATION: Synthetic

<400> SEQUENCE: 44

```
gaggtgcagc tggtggagtc tgggggaggc ctggtcaagc ctgggggtc  cctgagactc    60 tcctgtgcag cctctggatt caccttcagt aactatgcca tgtcttgggt ccgccaggct   120
ccagggaaga ggctggagtg gtcgcaacc attagtaatc gtggtagtta cacctactac    180
ccagactcag tgaagggccg attcaccatc tccagagaca acgccaagaa ctcactgtat   240
ctgcaaatga gcagcctgag atctgaggac acggctttgt attactgtgc gagagagagg   300
cctatggact actggggcca aggaacctca gtcaccgtct cctca                   345
```

<210> SEQ ID NO 45
<211> LENGTH: 345
<212> TYPE: DNA
<213> ORGANISM: Artificial Sequence
<220> FEATURE:
<223> OTHER INFORMATION: Synthetic

<400> SEQUENCE: 45

```
gaggtgcagc tggtggagtc tgggggaggc ctggtcaagc ctgggggtc  cctgagactc    60 tcctgtgcag cctctggatt caccttcagt aactatgcca tgtcttgggt ccgccagact   120
ccagagaaga ggctggagtg gtcgcaacc attagtaatc gtggtagtta cacctactac    180
ccagactcag tgaagggccg attcaccatc tccagagaca acgccaagaa ctcactgtat   240
ctgcaaatga gcagcctgag atctgaggac acggctttgt attactgtgc gagagagagg   300
cctatggact actggggcca aggaacctca gtcaccgtct cctca                   345
```

<210> SEQ ID NO 46
<211> LENGTH: 345
<212> TYPE: DNA
<213> ORGANISM: Artificial Sequence
<220> FEATURE:
<223> OTHER INFORMATION: Synthetic

<400> SEQUENCE: 46

```
gaggtgcagc tggtggagtc tgggggaggc ctggtcaagc ctgggggtc cctgagactc        60
tcctgtgcag cctctggatt caccttcagt aactatgcca tgtcttgggt ccgccaggct      120
ccagggaaga ggctggagtg gtcgcaacc attagtaatc gtggtagtta cacctactac      180
ccagactcag tgaagggccg attcaccatc tccagagaca cgccaagaa ctcactgtat      240
ctgcaaatga acagcctgag agccgaggac acggctttgt attactgtgc gagagagagg      300
cctatggact actggggcca aggaaccctg gtcaccgtct cctca                      345
```

<210> SEQ ID NO 47
<211> LENGTH: 345
<212> TYPE: DNA
<213> ORGANISM: Artificial Sequence
<220> FEATURE:
<223> OTHER INFORMATION: Synthetic

<400> SEQUENCE: 47

```
gaggtgcagc tggtggagtc tgggggaggc ctggtcaagc ctgggggtc cctgagactc        60
tcctgtgcag cctctggatt caccttcagt aactatgcca tgtcttgggt ccgccagact      120
ccagagaaga ggctggagtg gtcgcaacc attagtaatc gtggtagtta cacctactac      180
ccagactcag tgaagggccg attcaccatc tccagagaca cgccaagaa ctcactgtat      240
ctgcaaatga acagcctgag agccgaggac acggctttgt attactgtgc gagagagagg      300
cctatggact actggggcca aggaaccctg gtcaccgtct cctca                      345
```

<210> SEQ ID NO 48
<211> LENGTH: 321
<212> TYPE: DNA
<213> ORGANISM: Artificial Sequence
<220> FEATURE:
<223> OTHER INFORMATION: Synthetic

<400> SEQUENCE: 48

```
gacatcgtga tgacccagtc tccatccttc ctgtctgcat ctgtaggaga cagagtcacc        60
atcacttgca aggccagtca ggatgtgggt actgctgtag cctggtatca gcaaaaacca      120
gggcaacctc ctaagctcct gatctattgg gcatccactc ggcacactgg ggtcccagat      180
aggttcacag gcagtggatc tgggacagat ttcactctca caatcagcag cctgcagtct      240
gaagattttg cagtttattt ctgtcaccaa catagcagca atcctctcac gtttggccag      300
gggaccaagc tggagatcaa a                                                 321
```

<210> SEQ ID NO 49
<211> LENGTH: 321
<212> TYPE: DNA
<213> ORGANISM: Artificial Sequence
<220> FEATURE:
<223> OTHER INFORMATION: Synthetic

<400> SEQUENCE: 49

```
gacatcgtga tgacccagtc tccatccacc ctgtctgcat ctgtaggaga cagagtcacc        60
atcacttgca aggccagtca ggatgtgggt actgctgtag cctggtatca gcaaaaacca      120
gggcaacctc ctaagctcct gatctattgg gcatccactc ggcacactgg ggtcccagat      180
aggttcacag gcagtggatc tgggacagat ttcactctca caatcagcag cctgcaggct      240
gaagattttg cagtttattt ctgtcaccaa catagcagca atcctctcac gtttggccag      300
gggaccaagc tggagatcaa a                                                 321
```

<210> SEQ ID NO 50
<211> LENGTH: 321
<212> TYPE: DNA
<213> ORGANISM: Artificial Sequence
<220> FEATURE:
<223> OTHER INFORMATION: Synthetic

<400> SEQUENCE: 50

```
gacatccaga tgacccagtc tccatccacc ctgtctgcat ctgtaggaga cagagtcacc    60
atcacttgca aggccagtca ggatgtgggt actgctgtag cctggtatca gcaaaaacca   120
gggcaacctc ctaagctcct gatctattgg gcatccactc ggcacactgg ggtcccagat   180
aggttcagcg gcagtggatc tgggacagat ttcactctca caatcagcag cctgcaggct   240
gaagattttg cagtttattt ctgtcaccaa catagcagca atcctctcac gtttggccag   300
gggaccaagc tggagatcaa a                                             321
```

<210> SEQ ID NO 51
<211> LENGTH: 321
<212> TYPE: DNA
<213> ORGANISM: Artificial Sequence
<220> FEATURE:
<223> OTHER INFORMATION: Synthetic

<400> SEQUENCE: 51

```
gacatccaga tgacccagtc tccatccacc ctgtctgcat ctgtaggaga cagagtcacc    60
atcacttgcc gggccagtca ggatgtgggt actgctgtag cctggtatca gcaaaaacca   120
gggcaacctc ctaagctcct gatctattgg gcatccactc ggcacactgg ggtcccagat   180
aggttcagcg gcagtggatc tgggacagat ttcactctca caatcagcag cctgcaggct   240
gaagattttg cagtttatta ctgtcaccaa catagcagca atcctctcac gtttggccag   300
gggaccaagc tggagatcaa a                                             321
```

<210> SEQ ID NO 52
<211> LENGTH: 321
<212> TYPE: DNA
<213> ORGANISM: Artificial Sequence
<220> FEATURE:
<223> OTHER INFORMATION: Synthetic

<400> SEQUENCE: 52

```
gacatccaga tgacccagtc tccatccacc ctgtctgcat ctgtaggaga cagagtcacc    60
atcacttgcc gggccagtca ggatgtgggt actgctgtag cctggtatca gcaaaaacca   120
gggcaacctc ctaagctcct gatctattgg gcatccactc ggcacactgg ggtcccagat   180
aggttcagcg gcagtggatc tgggacagat ttcactctca caatcagcag cctgcaggct   240
gaagattttg caacttatta ctgtcaccaa catagcagca atcctctcac gtttggccag   300
gggaccaagc tggagatcaa a                                             321
```

<210> SEQ ID NO 53
<211> LENGTH: 322
<212> TYPE: DNA
<213> ORGANISM: Artificial Sequence
<220> FEATURE:
<223> OTHER INFORMATION: Synthetic

<400> SEQUENCE: 53

```
gacatcgtga tgacccagtc tccatccttc ctgtctgcat ctgtaggaga cagagtcacc    60
```

```
atcacttgca aggccagtca ggatgtgggt actgctgtag cctggtatca gcaaaaacca    120
gggaaagccc ctaagctcct gatctattgg gcatccactc ggcacactgg ggtcccagat    180
aggttcacag gcagtggatc atgggacaga tttcactctc acaatcagca gcctgcagtc    240
tgaagatttt gcagtttatt tctgtcacca acatagcagc aatcctctca cgtttggcca    300
ggggaccaag ctggagatca aa                                             322
```

<210> SEQ ID NO 54
<211> LENGTH: 321
<212> TYPE: DNA
<213> ORGANISM: Artificial Sequence
<220> FEATURE:
<223> OTHER INFORMATION: Synthetic

<400> SEQUENCE: 54

```
gacatccaga tgacccagtc tccatccacc ctgtctgcat ctgtaggaga cagagtcacc     60
atcacttgca aggccagtca ggatgtgggt actgctgtag cctggtatca gcaaaaacca    120
gggaaagccc ctaagctcct gatctattgg gcatccactc ggcacactgg ggtcccagat    180
aggttcagcg gcagtggatc tgggacagat ttcactctca caatcagcag cctgcaggct    240
gaagattttg cagtttattt ctgtcaccaa catagcagca atcctctcac gtttggccag    300
gggaccaagc tggagatcaa a                                              321
```

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Tyr Pro Tyr Asp Val Pro Asp Tyr Ala
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic

<400> SEQUENCE: 56

Asp Tyr Lys Asp Asp Asp Asp Lys
1               5

<210> SEQ ID NO 57
<211> LENGTH: 10
<212> TYPE: PRT
<213> ORGANISM: Artificial Sequence
<220> FEATURE:
<223> OTHER INFORMATION: Synthetic

<400> SEQUENCE: 57

Glu Gln Lys Leu Ile Ser Glu Glu Asp Leu
1               5                   10

<210> SEQ ID NO 58
<211> LENGTH: 5
<212> TYPE: PRT
<213> ORGANISM: Artificial Sequence
<220> FEATURE:
<223> OTHER INFORMATION: Synthetic

```
<400> SEQUENCE: 58

His His His His His
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic

<400> SEQUENCE: 59

His His His His His His
1               5

<210> SEQ ID NO 60
<211> LENGTH: 10
<212> TYPE: PRT
<213> ORGANISM: Artificial Sequence
<220> FEATURE:
<223> OTHER INFORMATION: Synthetic

<400> SEQUENCE: 60

Glu Gln Lys Leu Ile Ser Glu Glu Asp Leu
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Synthetic

<400> SEQUENCE: 61

Asp Tyr Lys Asp Asp Asp Asp Lys
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic

<400> SEQUENCE: 62

Trp Ser His Pro Gln Phe Glu Lys
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic

<400> SEQUENCE: 63

Tyr Pro Tyr Asp Val Pro Asp Tyr Ala
1               5

<210> SEQ ID NO 64
<211> LENGTH: 4
<212> TYPE: PRT
<213> ORGANISM: Artificial Sequence
<220> FEATURE:
<223> OTHER INFORMATION: Synthetic

<400> SEQUENCE: 64
```

```
Phe His His Thr
1

<210> SEQ ID NO 65
<211> LENGTH: 17
<212> TYPE: PRT
<213> ORGANISM: Artificial Sequence
<220> FEATURE:
<223> OTHER INFORMATION: Synthetic

<400> SEQUENCE: 65

Trp Glu Ala Ala Ala Arg Glu Ala Cys Cys Arg Glu Cys Cys Ala Arg
1               5                   10                  15

Ala

<210> SEQ ID NO 66
<211> LENGTH: 5
<212> TYPE: PRT
<213> ORGANISM: Artificial Sequence
<220> FEATURE:
<223> OTHER INFORMATION: Synthetic

<400> SEQUENCE: 66

Arg Tyr Ile Arg Ser
1               5
```

UNITED STATES PATENT AND TRADEMARK OFFICE
CERTIFICATE OF CORRECTION

| | | |
|---|---|---|
| PATENT NO. | : 11,999,780 B2 | Page 1 of 1 |
| APPLICATION NO. | : 17/557318 | |
| DATED | : June 4, 2024 | |
| INVENTOR(S) | : Graham Parry et al. | |

It is certified that error appears in the above-identified patent and that said Letters Patent is hereby corrected as shown below:

In the Claims

At Column 119, Claim 6, Line 51, the text:
"SEQ ID NOsi[H] 28-30"
Should read:
--SEQ ID NOs: 28-30--

Signed and Sealed this
Sixteenth Day of July, 2024

Katherine Kelly Vidal
*Director of the United States Patent and Trademark Office*